US008486621B2

(12) United States Patent
Luo et al.

(10) Patent No.: US 8,486,621 B2
(45) Date of Patent: Jul. 16, 2013

(54) NUCLEIC ACID-BASED MATRIXES

(75) Inventors: Dan Luo, Ithaca, NY (US); Soong Ho Um, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 808 days.

(21) Appl. No.: 11/464,184

(22) Filed: Aug. 11, 2006

(65) Prior Publication Data

US 2007/0117177 A1 May 24, 2007

Related U.S. Application Data

(60) Provisional application No. 60/722,032, filed on Sep. 29, 2005, provisional application No. 60/783,422, filed on Mar. 17, 2006, provisional application No. 60/783,426, filed on Mar. 17, 2006, provisional application No. 60/707,431, filed on Aug. 11, 2005, provisional application No. 60/745,383, filed on Apr. 21, 2006, provisional application No. 60/756,453, filed on Jan. 5, 2006.

(51) Int. Cl.
*C12Q 1/68* (2006.01)
*C70H 19/00* (2006.01)

(52) U.S. Cl.
USPC .......................................... 435/6.1; 536/22.1

(58) Field of Classification Search
None
See application file for complete search history.

(56) References Cited

U.S. PATENT DOCUMENTS

| | | | |
|---|---|---|---|
| 4,716,106 A | 12/1987 | Chiswell | |
| 5,278,051 A * | 1/1994 | Seeman et al. | 435/91.52 |
| 5,288,609 A | 2/1994 | Engelhardt et al. | |
| 5,359,100 A | 10/1994 | Urdea et al. | |
| 5,386,020 A | 1/1995 | Seeman et al. | |
| 5,449,602 A | 9/1995 | Royer et al. | |
| 5,563,056 A | 10/1996 | Swan et al. | |
| 6,197,556 B1 | 3/2001 | Ulanovsky et al. | |
| 6,221,581 B1 | 4/2001 | Engelhardt et al. | |
| 6,261,779 B1 | 7/2001 | Barbera-guillem et al. | |
| 6,265,021 B1 * | 7/2001 | Black et al. | 427/131 |
| 6,361,944 B1 | 3/2002 | Mirkin et al. | |
| 6,495,324 B1 | 12/2002 | Mirkin et al. | |
| 6,534,266 B1 | 3/2003 | Singer | |
| 6,664,061 B2 | 12/2003 | Elghanian et al. | |
| 6,689,374 B2 | 2/2004 | Chu et al. | |
| 6,787,357 B2 | 9/2004 | Bowlin et al. | |
| 6,893,822 B2 | 5/2005 | Schweitzer et al. | |
| 6,974,669 B2 | 12/2005 | Mirkin et al. | |
| 7,052,650 B2 | 5/2006 | Strick et al. | |
| 2002/0086989 A1 | 7/2002 | Guire et al. | |
| 2002/0123609 A1 | 9/2002 | Frechet et al. | |
| 2003/0036065 A1 | 2/2003 | Gellibolian | |
| 2004/0023391 A1 | 2/2004 | Fang et al. | |
| 2005/0019369 A1 * | 1/2005 | Lyles | 424/426 |
| 2005/0112578 A1 * | 5/2005 | Matsuura et al. | 435/6 |
| 2005/0130180 A1 | 6/2005 | Luo et al. | |
| 2006/0084607 A1 | 4/2006 | Spirio et al. | |
| 2007/0048759 A1 | 3/2007 | Luo et al. | |
| 2007/0148246 A1 | 6/2007 | Luo et al. | |
| 2008/0167454 A1 | 7/2008 | Luo et al. | |
| 2010/0136614 A1 | 6/2010 | Luo et al. | |
| 2012/0022244 A1 | 1/2012 | Yin | |

FOREIGN PATENT DOCUMENTS

WO   WO 2004/057023 A1   7/2004

OTHER PUBLICATIONS

Lin et al. (J Biomech Eng. Feb. 2004;126(1):104-10).*
Li et al. (Nat Mater. Jan. 2004;3(1):38-42. Epub Dec. 21, 2003).*
Ma et al. (Nucleic Acids Res. Dec. 22, 1986;14(24):9745-53).*
Matsuura, et al. 'Nucleo-nanocages': designed ternary oligodeoxyribonucleotides spontaneously form nanosized DNA cages. Chem Commun (Camb). 2003; (3):376-7.
Li, et al. Multiplexed detection of pathogen DNA with DNA-based fluorescence nanobarcodes. Nat Biotechnol. 2005; 23(7): 885-9.
Lund, et al. Self-assembling a molecular pegboard. J Am Chem Soc. 2005; 127(50): 17606-7.
Luo, D. The road from biology to materials. Materials Today. 2003; 6: 38-43.
Luo, et al. Enhancement of transfection by physical concentration of DNA at the cell surface. Nat Biotechnol. 2000; 18(8): 893-5.
Luo, et al. Poly(ethylene glycol)-conjugated PAMAM dendrimer for biocompatible, high-efficiency DNA delivery. Macromolecules. 2002; 35: 3456-62.
Prata, et al. Charge-reversal amphiphiles for gene delivery. J Am Chem Soc. 2004; 126(39): 12196-7.
Seeman, N. Nucleic acid junctions and lattices. J Theor Biol. 1982; 99(2): 237-47.
Um, et al. Dendrimer-like DNA-based fluorescence nanobarcodes. Nat Protoc. 2006; 1(2): 995-1000.
Um, et al. Enzyme-catalysed assembly of DNA hydrogel. Nat Mater. 2006; 5(10): 797-801.
Lou, et al. U.S. Appl. No. 60/483,032, filed Jun. 27, 2003, entitled "Nucleic acid-based materials."
Chu, et al. Industrial choices for protein production by large-scale cell culture. Cute Opin Biotechnol. Apr. 2001;12(2):180-7.
Stellwagen, N. C. Apparent pore size of polyacrylamide gels: comparison of gels cast and run in Tris-acetate-EDTA and Tris-borate-EDTA buffers. Electrophoresis. Jul. 1998;19(10):1542-7. (Abstract only).
Zangmeister, et al. UV Graft Polymerization of Polyacrylamide Hydrogel Plugs in Microfluidic Channels. Langmuir. 2003; 19(17):6901-6904.
U.S. Appl. No. 60/756,453, filed Jan. 5, 2006, Luo et al.
Astriab-Fisher, et al. Conjugates of antisense oligonucleotides with the Tat and antennapedia cell-penetrating peptides: effects on cellular uptake, binding to target sequences, and biologic actions. Pharm Res. 2002;19(6):744-54.

(Continued)

*Primary Examiner* — Christopher M. Babic
(74) *Attorney, Agent, or Firm* — Wilson Sonsini Goodrich & Rosati

(57) ABSTRACT

Various nucleic acid-based matrixes are provided, comprising nucleic acid monomers as building blocks, as well as nucleic acids encoding proteins, so as to produce novel biomaterials. Methods of utilizing such biomaterials include cell-free protein synthesis.

49 Claims, 24 Drawing Sheets

OTHER PUBLICATIONS

Bongartz, et al. Improved biological activity of antisense oligonucleotides conjugated to a fusogenic peptide. Nucleic Acids Res. 1994;22(22):4681-8.

Bonny, et al. Cell-permeable peptide inhibitors of JNK: novel blockers of beta-cell death. Diabetes. 2001; 50(1):77-82.

Braeckmans, et al. Encoding Microcarriers: Present and Future Technologies. Nature Reviews Drug Discovery. 2002; 1:447-456.

Chan, et al. Luminescent Quantum Dots for Multiplexed Biological Detection and Imaging. Curr. Op. Biotech. 2002; 13:40-46.

Corbel, et al. Latest developments and in vivo use of the Tet system: ex vivo and in vivo delivery of tetracycline-regulated genes. Curr Opin Biotechnol. 2002; 13(5):448-52.

Dadlani, M. N. Image processing of DNA nanobarcode. The Graduate School of Cornell University (2005) (Dissertation).

Fawell, et al. Tat-mediated delivery of heterologous proteins into cells. Proc Natl Acad Sci U S A. 1994; 91(2):664-8.

Freeman, et al. Screening of large protein libraries by the cell immobilized on adsorbed bead approach. Biotechnol Bioeng. Apr. 20, 2004;86(2):196-200.

Fulton, et al. Advanced Multiplexed Analysis with the FlowMetrix(TM) System. Clinical Chemistry 1997; 43:1749-1756.

Han, et al. Quantum-Dot-Tagged Microbeads for Multiplexed Optical Coding of Biomolecules. Nature Biotechnology. 2001; 19:631-635.

Keller, et al. Biophysical characterization of the DNA binding and condensing properties of adenoviral core peptide mu. Biochemistry. 2002;41(2):652-9.

Kukuruzinska, et al. Protein N-glycosylation: molecular genetics and functional significance. Crit Rev Oral Biol Med. 1998;9(4):415-48.

Luo, et al. Synthetic DNA delivery systems. Nat Biotechnol. 2000; 18(1):33-7.

Nicewarner-Pena, et al. Submicrometer Metallic Barcodes. Science. 2001; 294:137-141.

Ried, et al. Simultaneous Visualization of 7 Different DNA Probes by In situ Hybridization Using Combinatorial Fluorescence and Digital Imaging Microscopy. Proc. Nat'l. Acad. Sci. USA. 1992; 89:1388-1392.

Rubina, et al. Hydrogel drop microchips with immobilized DNA: properties and methods for large-scale production. Anal Biochem. Feb. 1, 2004;325(1):92-106.

Shchepinov, et al. Oligonucleotide dendrimers: synthesis and use as polylabelled DNAa probes. Nucleic Acids Res. Nov. 15, 1997;25(22):4447-54.

Smith, et al. Synthetic peptide-based DNA complexes for nonviral gene delivery. Adv Drug Deliv Rev. 1998; 30(1-3):115-131.

Steemers, et al. Screening Unlabeled DNA Targets with Randomly Ordered Fiber-Optic Gene Arrays. Nature Biotechnology. 2000; 18:91-94.

Tanke, et al. New strategy for multi-colour fluorescence in situ hybridisation: COBRA: COmbined Binary RAtio labelling. Eur J Hum Genet. Jan. 1999;7(1):2-11.

Torchilin, et al. TAT peptide on the surface of liposoines affords their efficient intracellular delivery even at low temperature and in the presence of metabolic inhibitors. Proc Nati Acad Sci U S A. 2001; 98(15):8786-91.

Vives, et al. Selective Coupling of a Highly Basic Peptide to an Oligonucleotide. Tetrahedron Letters. 1997; 38 (7):1183-1186.

Wang, et al. Encoded Beads for Electrochemical Identification. Anal. Chem. 2003; 75:4667-4671.

Zanta, et al. Gene delivery: a single nuclear localization signal peptide is sufficient to carry DNA to the cell nucleus. Proc Natl Acad Sci U S A. 1999; 96(1):91-6.

Zhu, et al. Nylon/DNA: Single-stranded DNA with a covalently stitched nylon lining. J Am Chem Soc. 2003; 125(34):10178-9.

U.S. Appl. No. 13/210,095, filed Aug. 15, 2011, Luo et al.

Roh, et al. DNAsomes: Multifunctional DNA-based nanocarriers. Small. Jan. 3, 2011;7(1):74-8.

Matsuoka, et al. Structural and immunostimulatory properties of Y-shaped DNA consisting of phosphodiester and phosphorothioate oligodeoxynucleotides. J Control Release. Dec. 20, 2010;148(3):311-6.

Mizuno, et al. Simultaneous delivery of doxorubicin and immunostimulatory CpG motif to tumors using a plasmid DNA/doxorubicin complex in mice. J Control Release. Jan. 25, 2010;141(2):252-9.

Nishikawa, et al. Biodegradable CpG DNA hydrogels for sustained delivery of doxorubicin and immunostimulatory signals in tumor-bearing mice. Biomaterials. Jan. 2011;32(2):488-94.

Nishikawa, et al. DNA-based nano-sized systems for pharmaceutical and biomedical applications. Adv Drug Deliv Rev. Apr. 30, 2010;62(6):626-32.

Nishikawa, et al. Enhanced immunostimulatory activity of oligodeoxynucleotides by Y-shape formation. Immunology. Jun. 2008;124(2):247-55.

Rattanakiat, et al. The assembly of a short linear natural cytosine-phosphate-guanine DNA into dendritic structures and its effect on immunostimulatory activity. Biomaterials. Oct. 2009;30(29):5701-6.

Aldeman, L. M. Molecular computation of solutions to combinatorial problems. Science. 1994; 266:1021-1024.

Alivisatos, et al. Organization of 'nanocrystal molecules' using DNA. Nature. 1996; 382:609-611.

Altschul, et al. Basic Local Alignment Search Tool. J. Mol. Biol. 1990; 215:403-410.

Altschul, et al. Gapped BLAST and PSI-BLAST: A New Generation of Protein Database Search Programs. Nucleic Acids Res. 1997; 25(17):3389-3402.

Benenson, et al. Programmable and Autonomous Computing Machine Made of Biomolecules. Nature. 2001; 414:430-434.

Bouchiat, et al. Estimating the Persistence Length of a Worm-Like Chain Molecule from Force-Extension Measurements. Biophys. J. 1999; 76:409-413.

Braun, et al. DNA-Templated Assembly and Electrode Attachment of a Conducting Silver Wire. Nature. 1998; 391:775-778.

Corpet, F. Multiple Sequence Alignment with Hierarchical Clustering. Nucleic Acids Res. 1988; 16(22):10881-10890.

Demers, et al. Direct Patterning of Modified Oligonucleotides on Metals and Insulators by Dip-Pen Nanolitnography. Science. 2002; 296: 1836-1838.

Drexler, K.E. Molecular Engineering: An Approach to the Development of General Capabilities for Molecular Manipulation. Proc. Natl. Acad. Sci. USA. 1981; 78(9):5275-5278.

Eckardt, et al. Chemical Copying of Connectivity. Nature. 2002; 420:286.

Elghanian, et al. Selective Colorimetric Detection of Polynucleotides Based on the Distance-Dependent Optical Properties of Gold Nanoparticles. Science. 1997; 277:1078-1081.

Feynman, R.P. There's Plenty of Room at the Bottom, in Miniaturization, Horace D. Gilbert Ed., Reinhold Publishing Corporation, New York. 1961; pp. 282-296.

Gite, et al. A high-throughput nonisotopic protein truncation test. Nat Biotechnol. 2003;21(2):194-7.

Guarnieri, et al. Making DNA Add. Science. 1996; 273:220-223.

Higgins, et al. CLUSTAL: A Package for Performing Multiple Sequence Alignment on a Microcomputer. Gene. 1988; 73:237-244.

Higgins, et al. Fast and Sensitive Multiple Sequence Alignments on a Microcomputer. CABIOS Commun. 1989; 5(2):151-153.

http://dictionsary.refrences.com/search?q=isotropic.

Huang, et al. Parallelization of a Local Similarity Algorithm. CABIOS. 1992; 8(2): 155-165.

Kadrmas, et al. Relative stabilities of DNA three-way, four-way and five-way junctions (multi-helix junction loops): unpaired nucleotides can be stabilizing or destabilizing. Nucleic Acids Res. 1995; 23(12):2212-22.

Kallenbach, et al. Fourth Rank Immobile Nucleic Acid Junctions. J. Biomol. Struct. Dyn. 1983; 1:159-168.

Karlin, et al. Applications and Statistics for Multiple High-Scoring Segments in Molecular Sequences. Proc. Natl. Acad. Sci. USA. 1993; 90:5873-5877.

Karlin, et al. Methods for Assessing the Statistical Significance of Molecular Sequence Features by Using General Scoring Schemes. Proc. Natl. Acad. Sci. USA. 1990; 87:2264-2268.

Keren, et al. Sequence-Specific Molecular Lithography on Single DNA Molecules. Science. 2002; 297:72-75.

Labean, et al. Construction, Analysis, Ligation, and Self-Assembly of DNA Triple Crossover Complexes. J. Am. Chem. Soc. 2000; 122:1848-1860.
Li, et al. Controlled Assembly of Dendrimer-like DNA. Nature Materials. 2004; 3:38-42.
Luo, D. Novel Crosslinking Technologies to Assess Protein-DNA Binding and DNA-DNA Complexes for Gene Delivery and Expression. Molecular, Cellular, and Developmental Biology Program. The Ohio State University (1997) (Dissertation).
Ma, et al. Three-Arm Nucleic Acid Junctions are Flexible. Nucleic Acids Res. 1986; 14(24):9745-9753.
Mao, et al. A Nanomechanical Device Based on the B-Z Transition of DNA. Nature. 1999; 397:144-146.
Mao, et al. Assembly of Borromean Rings from DNA. Nature. 1997; 386:137-138.
Mao, et al. Designed Two-Dimensional DNA Holliday Junction Arrays Visualized by Atomic Force Microscopy. J. Am. Chem. Soc. 1999; 121:5437-5443.
Mao, et al. Logical Computation Using Algorithmic Self-Assembly of DNA Triple-Crossover Molecules. Nature. 2000; 407:493-496.
Mirkin, et al. A DNA-Based Method for Rationally Assembling Nanoparticles Into Macroscopic Materials. Nature. 1996; 382:607-609.
Myers, et al. Optimal Alignment in Linear Space. CABIOS. 1988; 4(1): 11-17.
Needleman, et al. A General Method Applicable to the Search for Similarities in the Amino Acid Sequence of Two Proteins. J. Mol. Biol. 1970; 48:443-453.
Niemeyer, C.M. Nanoparticles, Proteins, and Nucleic Acids: Biotechnology Meets Materials Science. Angew. Chem. Int. Ed. 2001; 40:4129-4158.
Niemeyer, C.M. Progress in "Engineering Up" Nanotechnology Devices Utilizing DNA as a Construction Material. Appl. Phys. 1999; A 68: 119-124.
Niemeyer, et al. Covalent DNA—Streptavidin Conjugates as Building Blocks for Novel Biometallic Nanostrucrures. Angew. Chem. Int. Ed. 1998; 37(16):2265-2268.
Nilsen, et al. Dendritic Nucleic Acid Structures. J. Theor. Biol. 1997; 187:273-284.
Ouyang, et al. DNA Solution of the Maximal Clique Problem. Science. 1997; 278:446-449.
Park, et al. Array-Based Electrical Detection of DNA with Nanoparticle Probes. Science. 2002; 295:1503-1506.
Pearson, et al. Improved Tools for Biological Sequence Comparison. Proc. Natl. Acad. Sci. USA. 1988; 85:2444-2448.
Pearson, W.R. Using the FASTA Program to Search Protein and DNA Sequence Databases. Meth. Mol. Biol. 1994; 24:307-331.
Robinson, et al. The Design of a Biochip: A Self-Assembling Molecular-Scale Memory Device. Prot. Eng. 1987; 1(4):295-300.
Sakamoto, et al. Molecular Computation by DNA Hairpin Formation. Science. 2000; 288:1223-1226.
Seeman, et al. Designed Two Dimensional Holliday Junction Arrays. Biophys. J. 2000; 78:308a (abstract).
Seeman, et al. Emulating Biology: Building Nanostmctures from the Bottom Up. Proc. Natl. Acad. Sci. USA. 2002; 99(Suppl. 2):6451-6455.
Seeman, N.C. Construction of Three-Dimensional Stick Figures from Branched DNA. DNA & Cell Biol. 1991; 10(7):475-486.
Seeman, N.C. DeNovo Design of Sequences for Nucleic Acid Structural Engineering. J. Biomol. Struct. Dyn. 1990; 8(3):573-581.
Seeman, N.C. DNA Components for Molecular Architecture. Ace. Chem. Res. 1997; 30:357-363.
Seeman, N.C. DNA Engineering and Its Application to Nanotechnology. Trends in Biotech. 1999; 17:437-443.
Seeman, N.C. DNA Nanotechnology: Novel DNA Constructions. Annu. Rev. Biophys. Biomol. Struct. 1998; 27:225-248.
Seeman, N.C. The Use of Branched DNA for Nanoscale Fabrication. Nanotechnology 1991; 2:149-159.
Sha, et al. Atomic Force Microscopy of Parallel DNA Branched Junction Arrays. Chemistry & Biology. 2000; 7:743-751.

Smith, et al. Comparison of Biosequences. Adv. Appl. Math. 1981; 2:482-489.
Smith, et al. Direct Mechanical Measurements of the Elasticity of Single DNA Molecules by Using Magnetic Beads. Science. 1992; 258: 1122-1126.
Taton, et al. The DNA-Mediated Formation of Supramolecular Mono- and Multilayered Nanoparticle Structures. J. Am. Chem. Soc. 2000; 122:6305-6306.
Tijssen, P. Overview of Principles of Hybridization and the Strategy of Nucleic Acid Probe Assays, in Laboratory Techniques in Biochemistry and Molecular Biology, Part 1, Chapter 2, Hybridization with Nucleic Acid Probes, Elsevier, New York. 1993; pp. 19-78.
Tinland, et al. Persistence Length of Single-Stranded DNA. Macromolecules. 1997; 30:5763-5765.
Tóth, et al. DNA Curvature in Solution Measured by Fluorescence Resonance Energy Transfer. Biochemistry. 1998; 37:8173-8179.
Wang, et al. Dendritic Nucleic Acid Probes for DNA Biosensors. J. Am. Chem. Soc. 1998; 120:8281-8282.
Watson, et al. DNA-Block Copolymer Conjugates. J. Am. Chem. Soc. 2001; 123:5592-5593.
Winfree, et al. Design and Self-Assembly of Two-Dimensional DNA Crystals. Nature. 1998; 394:539-544.
Yan, et al. A Robust DNA Mechanical Device Controlled by Hybridization Topology. Nature. 2002; 415:62-65.
Yang, et al. Ligation of DNA Triangles Containing Double Crossover Molecules. J. Am. Chem. Soc. 1998; 120:9779-9786.
Yurke, et al. A DNA-Fuelled Molecular Machine Made of DNA. Nature. 2000; 406:605-608.
Gothelf. Materials science. LEGO-like DNA structures. Science. Nov. 30, 2012;338(6111):1159-60. doi: 10.1126/science.1229960.
Lee, et al. Molecularly self-assembled nucleic acid nanoparticles for targeted in vivo siRNA delivery. Nat Nanotechnol. Jun. 3, 2012;7(6):389-93. doi: 10.1038/nnano.2012.73.
Li, et al. Self-assembled multivalent DNA nanostructures for noninvasive intracellular delivery of immunostimulatory CpG oligonucleotides. ACS Nano. Nov. 22, 2011;5(11):8783-9. doi: 10.1021/nn202774x. Epub Oct. 17, 2011.
Office action dated Jan. 27, 2009 for U.S. Appl. No. 11/423,633.
Office action dated Mar. 27, 2009 for U.S. Appl. No. 11/464,181.
Office action dated May 16, 2011 for U.S. Appl. No. 11/583,990.
Office action dated May 19, 2009 for U.S. Appl. No. 11/423,633.
Office action dated Jun. 3, 2009 for U.S. Appl. No. 11/738,849.
Office action dated Jun. 22, 2010 for U.S. Appl. No. 11/423,633.
Office action dated Jul. 10, 2008 for U.S. Appl. No. 11/423,633.
Office action dated Aug. 7, 2006 for U.S. Appl. No. 10/877,697.
Office action dated Sep. 28, 2012 for U.S. Appl. No. 11/464,181.
Office action dated Sep. 30, 2008 for U.S. Appl. No. 11/464,181.
Office action dated Nov. 23, 2010 for U.S. Appl. No. 11/583,990.
Office action dated Dec. 1, 2005 for U.S. Appl. No. 10/877,697.
Office action dated Dec. 24, 2009 for U.S. Appl. No. 11/464,181.
Office action dated Dec. 28, 2009 for U.S. Appl. No. 11/738,849.
Demeshkina, et al. Nucleotides of 18S rRNA surrounding mRNA codons at the human ribosomal A, P, and E sites: a crosslinking study with mRNA analogs carrying an aryl azide group at either the uracil or the guanine residue. RNA. Dec. 2000;6(12): 1727-36.
Fujimoto, et al. Reversible DNA photocircularization on triple helix: effect of vinyl substituent on base stacking. Tetrahedron Letters. 2000; 41:7897-7900.
Fujimoto, et al. Template-Directed Photoreversible Ligation of Deoxyoligonucleotides via 5-Vinyldeoxyuridine. J. Am. Chem. Soc., 2000; 122(23):5646-5647.
International search report dated Mar. 22, 2010 for PCT Application No. US2009/52795.
Lebedeva, et al. Interaction of replication protein A with photoreactive DNA structures. Biochemistry (Mosc). Feb. 2004;69(2):208-15.
Liu, et al. Template-directed photoligation of oligodeoxyribonucleotides via 4-thiothymidine. Nucleic Acids Research. 1998; 26(13):3300-3304.

* cited by examiner

FIGURES 2A, 2B, 2C, 2D and 2E:
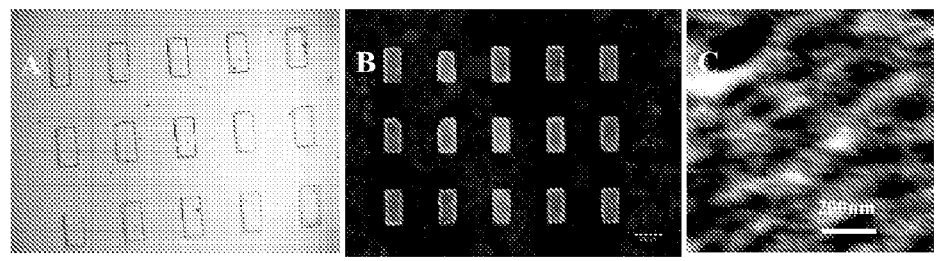
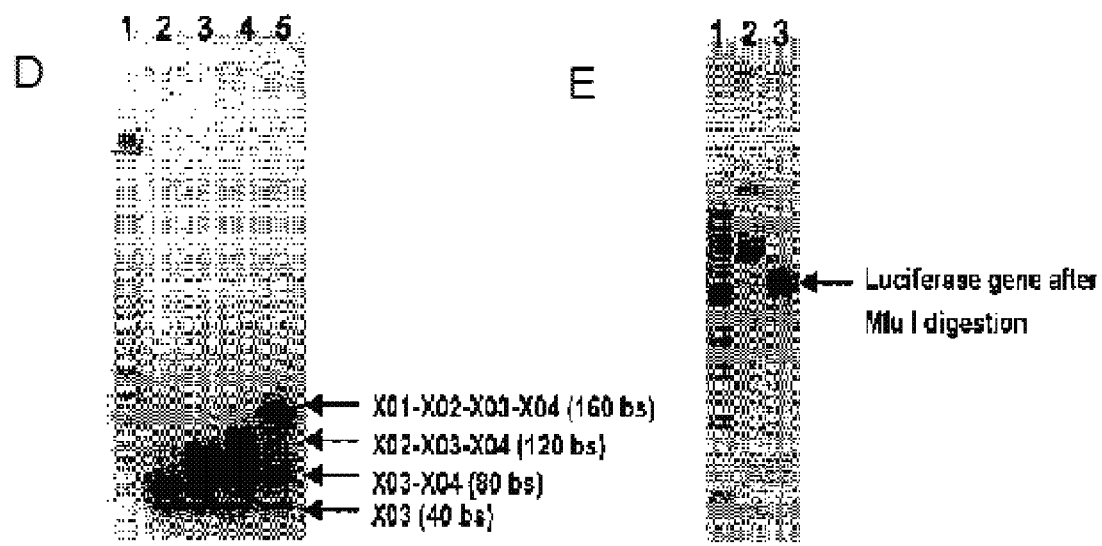

FIGURES 5A, 5B, 5C, 5D, 5E, and 5G:
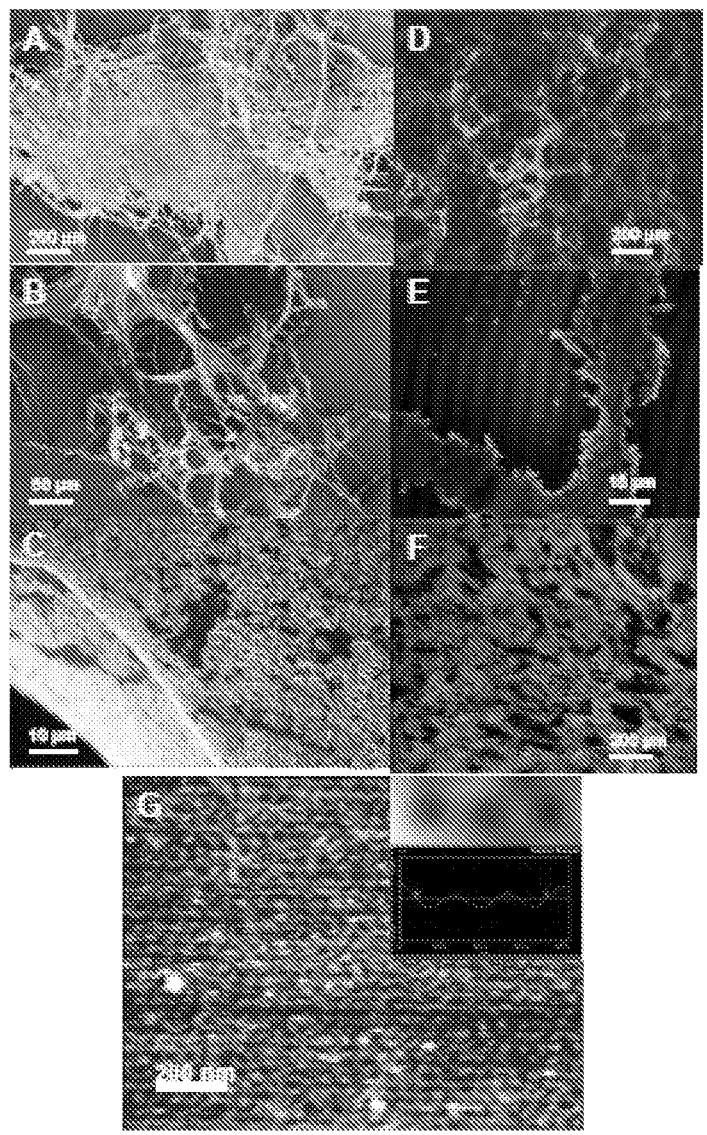

dumbbell-DNA

AuNP

```
                         SEQUENCE LISTING

<160> NUMBER OF SEQ ID NOS: 122

<210> SEQ ID NO 1
<211> LENGTH: 16
<212> TYPE: PRT
<213> ORGANISM: Artificial
<220> FEATURE:
<223> OTHER INFORMATION: Synthetic peptide sequences

<400> SEQUENCE: 1

Asp Ala Asp Ala Asp Ala Asp Ala Arg Ala Arg Ala Arg Ala Arg Ala
1               5                   10                  15

<210> SEQ ID NO 2
<211> LENGTH: 16
<212> TYPE: PRT
<213> ORGANISM: Artificial
<220> FEATURE:
<223> OTHER INFORMATION: Synthetic peptide sequence

<400> SEQUENCE: 2

Ala Asp Ala Asp Ala Asp Ala Asp Ala Arg Ala Arg Ala Arg Ala Arg
1               5                   10                  15

<210> SEQ ID NO 3
<211> LENGTH: 16
<212> TYPE: PRT
<213> ORGANISM: Artificial
<220> FEATURE:
<223> OTHER INFORMATION: Synthetic peptide sequence

<400> SEQUENCE: 3

His Glu His Glu His Lys His Lys His Glu His Glu His Lys His Lys
1               5                   10                  15

<210> SEQ ID NO 4
<211> LENGTH: 8
<212> TYPE: PRT
<213> ORGANISM: Artificial
<220> FEATURE:
<223> OTHER INFORMATION: Synthetic peptide sequence

<400> SEQUENCE: 4

His Glu His Glu His Lys His Lys
1               5

<210> SEQ ID NO 5
<211> LENGTH: 20
<212> TYPE: PRT
<213> ORGANISM: Artificial
<220> FEATURE:
<223> OTHER INFORMATION: Synthetic peptide sequence
```

```
<400> SEQUENCE: 5

Val Glu Val Glu Val Glu Val Glu Val Glu Val Glu Val Glu Val Glu
1               5                   10                  15

Val Glu Val Glu
            20

<210> SEQ ID NO 6
<211> LENGTH: 20
<212> TYPE: PRT
<213> ORGANISM: Artificial
<220> FEATURE:
<223> OTHER INFORMATION: Synthetic peptide sequence

<400> SEQUENCE: 6

Arg Phe Arg Phe Arg Phe Arg Phe Arg Phe Arg Phe Arg Phe Arg Phe
1               5                   10                  15

Arg Phe Arg Phe
            20

<210> SEQ ID NO 7
<211> LENGTH: 16
<212> TYPE: PRT
<213> ORGANISM: Artificial
<220> FEATURE:
<223> OTHER INFORMATION: Synthetic peptide sequence

<400> SEQUENCE: 7

Arg Ala Asp Ala Arg Ala Asp Ala Arg Ala Asp Ala Arg Ala Asp Ala
1               5                   10                  15

<210> SEQ ID NO 8
<211> LENGTH: 16
<212> TYPE: PRT
<213> ORGANISM: Artificial
<220> FEATURE:
<223> OTHER INFORMATION: Synthetic peptide sequence

<400> SEQUENCE: 8

Arg Ala Asp Ala Arg Gly Asp Ala Arg Ala Asp Ala Arg Gly Asp Ala
1               5                   10                  15

<210> SEQ ID NO 9
<211> LENGTH: 8
<212> TYPE: PRT
<213> ORGANISM: Artificial
<220> FEATURE:
<223> OTHER INFORMATION: Synthetic peptide sequence

<400> SEQUENCE: 9

Arg Ala Asp Ala Arg Ala Asp Ala
1               5

<210> SEQ ID NO 10
<211> LENGTH: 16
<212> TYPE: PRT
<213> ORGANISM: Artificial
<220> FEATURE:
<223> OTHER INFORMATION: Synthetic peptide sequence

<400> SEQUENCE: 10

Arg Ala Arg Ala Asp Ala Asp Ala Arg Ala Arg Ala Asp Ala Asp Ala
1               5                   10                  15

<210> SEQ ID NO 11
<211> LENGTH: 8
<212> TYPE: PRT
```

<213> ORGANISM: Artificial
<220> FEATURE:
<223> OTHER INFORMATION: Synthetic peptide sequence

<400> SEQUENCE: 11

Arg Ala Arg Ala Asp Ala Asp Ala
1               5

<210> SEQ ID NO 12
<211> LENGTH: 16
<212> TYPE: PRT
<213> ORGANISM: Artificial
<220> FEATURE:
<223> OTHER INFORMATION: Synthetic peptide sequence

<400> SEQUENCE: 12

Ala Glu Ala Lys Ala Glu Ala Lys Ala Glu Ala Lys Ala Glu Ala Lys
1               5                   10                  15

<210> SEQ ID NO 13
<211> LENGTH: 8
<212> TYPE: PRT
<213> ORGANISM: Artificial
<220> FEATURE:
<223> OTHER INFORMATION: Synthetic peptide sequence

<400> SEQUENCE: 13

Ala Glu Ala Lys Ala Glu Ala Lys
1               5

<210> SEQ ID NO 14
<211> LENGTH: 16
<212> TYPE: PRT
<213> ORGANISM: Artificial
<220> FEATURE:
<223> OTHER INFORMATION: Synthetic peptide sequence

<400> SEQUENCE: 14

Arg Ala Glu Ala Arg Ala Glu Ala Arg Ala Glu Ala Arg Ala Glu Ala
1               5                   10                  15

<210> SEQ ID NO 15
<211> LENGTH: 8
<212> TYPE: PRT
<213> ORGANISM: Artificial
<220> FEATURE:
<223> OTHER INFORMATION: Synthetic peptide sequence

<400> SEQUENCE: 15

Arg Ala Glu Ala Arg Ala Glu Ala
1               5

<210> SEQ ID NO 16
<211> LENGTH: 16
<212> TYPE: PRT
<213> ORGANISM: Artificial
<220> FEATURE:
<223> OTHER INFORMATION: Synthetic peptide sequence

<400> SEQUENCE: 16

Lys Ala Asp Ala Lys Ala Asp Ala Lys Ala Asp Ala Lys Ala Asp Ala
1               5                   10                  15

<210> SEQ ID NO 17
<211> LENGTH: 8
<212> TYPE: PRT
<213> ORGANISM: Artificial
<220> FEATURE:

```
<223> OTHER INFORMATION: Synthetic peptide sequence

<400> SEQUENCE: 17

Lys Ala Asp Ala Lys Ala Asp Ala
1               5

<210> SEQ ID NO 18
<211> LENGTH: 12
<212> TYPE: PRT
<213> ORGANISM: Artificial
<220> FEATURE:
<223> OTHER INFORMATION: Synthetic peptide sequence

<400> SEQUENCE: 18

Lys Leu Asp Leu Lys Leu Asp Leu Lys Leu Asp Leu
1               5                   10

<210> SEQ ID NO 19
<211> LENGTH: 16
<212> TYPE: PRT
<213> ORGANISM: Artificial
<220> FEATURE:
<223> OTHER INFORMATION: Synthetic peptide sequence

<400> SEQUENCE: 19

Ala Glu Ala Glu Ala His Ala His Ala Glu Ala Glu Ala His Ala His
1               5                   10                  15

<210> SEQ ID NO 20
<211> LENGTH: 8
<212> TYPE: PRT
<213> ORGANISM: Artificial
<220> FEATURE:
<223> OTHER INFORMATION: Synthetic peptide sequence

<400> SEQUENCE: 20

Ala Glu Ala Glu Ala His Ala His
1               5

<210> SEQ ID NO 21
<211> LENGTH: 16
<212> TYPE: PRT
<213> ORGANISM: Artificial
<220> FEATURE:
<223> OTHER INFORMATION: Synthetic peptide sequence

<400> SEQUENCE: 21

Phe Glu Phe Glu Phe Lys Phe Lys Phe Glu Phe Glu Phe Lys Phe Lys
1               5                   10                  15

<210> SEQ ID NO 22
<211> LENGTH: 8
<212> TYPE: PRT
<213> ORGANISM: Artificial
<220> FEATURE:
<223> OTHER INFORMATION: Synthetic peptide sequence

<400> SEQUENCE: 22

Phe Glu Phe Lys Phe Glu Phe Lys
1               5

<210> SEQ ID NO 23
<211> LENGTH: 12
<212> TYPE: PRT
<213> ORGANISM: Artificial
<220> FEATURE:
<223> OTHER INFORMATION: Sythetic peptide sequence
```

```
<400> SEQUENCE: 23

Phe Lys Phe Glu Phe Lys Phe Glu Phe Lys Phe Glu
1               5                   10

<210> SEQ ID NO 24
<211> LENGTH: 8
<212> TYPE: PRT
<213> ORGANISM: Artificial
<220> FEATURE:
<223> OTHER INFORMATION: Synthetic peptide sequence

<400> SEQUENCE: 24

Phe Lys Phe Glu Phe Lys Phe Glu
1               5

<210> SEQ ID NO 25
<211> LENGTH: 16
<212> TYPE: PRT
<213> ORGANISM: Artificial
<220> FEATURE:
<223> OTHER INFORMATION: Synthetic peptide sequence

<400> SEQUENCE: 25

Phe Lys Phe Glu Phe Lys Phe Glu Phe Lys Phe Glu Phe Lys Phe Glu
1               5                   10                  15

<210> SEQ ID NO 26
<211> LENGTH: 12
<212> TYPE: PRT
<213> ORGANISM: Artificial
<220> FEATURE:
<223> OTHER INFORMATION: Synthetic peptide sequence

<400> SEQUENCE: 26

Phe Lys Phe Gln Phe Lys Phe Gln Phe Lys Phe Gln
1               5                   10

<210> SEQ ID NO 27
<211> LENGTH: 12
<212> TYPE: PRT
<213> ORGANISM: Artificial
<220> FEATURE:
<223> OTHER INFORMATION: Synthetic peptide sequence

<400> SEQUENCE: 27

Ile Lys Ile Glu Ile Lys Ile Glu Ile Lys Ile Glu
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic peptide sequence

<400> SEQUENCE: 28

Val Lys Val Glu Val Lys Val Glu Val Lys Val Glu
1               5                   10

<210> SEQ ID NO 29
<211> LENGTH: 16
<212> TYPE: PRT
<213> ORGANISM: Artificial
<220> FEATURE:
<223> OTHER INFORMATION: Synthetic peptide sequence

<400> SEQUENCE: 29
```

Leu Glu Leu Glu Leu Lys Leu Lys Leu Glu Leu Glu Leu Lys Leu Lys
1               5                   10                  15

<210> SEQ ID NO 30
<211> LENGTH: 8
<212> TYPE: PRT
<213> ORGANISM: Artificial
<220> FEATURE:
<223> OTHER INFORMATION: Synthetic peptide sequence

<400> SEQUENCE: 30

Leu Glu Leu Glu Leu Lys Leu Lys
1               5

<210> SEQ ID NO 31
<211> LENGTH: 16
<212> TYPE: PRT
<213> ORGANISM: Artificial
<220> FEATURE:
<223> OTHER INFORMATION: Synthetic peptide sequence

<400> SEQUENCE: 31

Ala Glu Ala Glu Ala Lys Ala Lys Ala Glu Ala Glu Ala Lys Ala Lys
1               5                   10                  15

<210> SEQ ID NO 32
<211> LENGTH: 12
<212> TYPE: PRT
<213> ORGANISM: Artificial
<220> FEATURE:
<223> OTHER INFORMATION: Synthetic peptide sequence

<400> SEQUENCE: 32

Ala Glu Ala Glu Ala Glu Ala Glu Ala Lys Ala Lys
1               5                   10

<210> SEQ ID NO 33
<211> LENGTH: 8
<212> TYPE: PRT
<213> ORGANISM: Artificial
<220> FEATURE:
<223> OTHER INFORMATION: Synthetic peptide sequence

<400> SEQUENCE: 33

Ala Glu Ala Glu Ala Lys Ala Lys
1               5

<210> SEQ ID NO 34
<211> LENGTH: 16
<212> TYPE: PRT
<213> ORGANISM: Artificial
<220> FEATURE:
<223> OTHER INFORMATION: Synthetic peptide sequence

<400> SEQUENCE: 34

Lys Ala Lys Ala Lys Ala Lys Ala Glu Ala Glu Ala Glu Ala Glu Ala
1               5                   10                  15

<210> SEQ ID NO 35
<211> LENGTH: 16
<212> TYPE: PRT
<213> ORGANISM: Artificial
<220> FEATURE:
<223> OTHER INFORMATION: Synthetic peptide sequence

<400> SEQUENCE: 35

Ala Glu Ala Glu Ala Glu Ala Glu Ala Lys Ala Lys Ala Lys Ala Lys
1               5                   10                  15

-continued

```
<210> SEQ ID NO 36
<211> LENGTH: 16
<212> TYPE: PRT
<213> ORGANISM: Artificial
<220> FEATURE:
<223> OTHER INFORMATION: Synthetic peptide sequence

<400> SEQUENCE: 36

Arg Ala Arg Ala Arg Ala Arg Ala Asp Ala Asp Ala Asp Ala Asp Ala
1               5                   10                  15

<210> SEQ ID NO 37
<211> LENGTH: 16
<212> TYPE: PRT
<213> ORGANISM: Artificial
<220> FEATURE:
<223> OTHER INFORMATION: Synthetic peptide sequence

<400> SEQUENCE: 37

Ala Asp Ala Asp Ala Asp Ala Asp Ala Arg Ala Arg Ala Arg Ala Arg
1               5                   10                  15

<210> SEQ ID NO 38
<211> LENGTH: 26
<212> TYPE: PRT
<213> ORGANISM: Artificial
<220> FEATURE:
<223> OTHER INFORMATION: Synthetic peptide sequence

<400> SEQUENCE: 38

Arg Gly Asp Tyr Arg Tyr Asp Tyr Thr Phe Arg Glu Glu Glu Gly Leu
1               5                   10                  15

Gly Ser Arg Tyr Asp Tyr Arg Gly Asp Tyr
            20                  25

<210> SEQ ID NO 39
<211> LENGTH: 26
<212> TYPE: PRT
<213> ORGANISM: Artificial
<220> FEATURE:
<223> OTHER INFORMATION: Synthetic peptide sequence

<400> SEQUENCE: 39

Arg Gly Asp Tyr Arg Tyr Asp Tyr Thr Phe Lys Glu Glu Glu Gly Leu
1               5                   10                  15

Gly Ser Arg Tyr Asp Tyr Asp Gly Asp Tyr
            20                  25

<210> SEQ ID NO 40
<211> LENGTH: 26
<212> TYPE: PRT
<213> ORGANISM: Artificial
<220> FEATURE:
<223> OTHER INFORMATION: Synthetic peptide sequence

<400> SEQUENCE: 40

Arg Gly Asp Tyr Arg Tyr Asp Tyr Thr Ala Ser Glu Leu Glu Gly Arg
1               5                   10                  15

Gly Thr Arg Tyr Asp Tyr Arg Gly Asp Tyr
            20                  25

<210> SEQ ID NO 41
<211> LENGTH: 27
<212> TYPE: PRT
<213> ORGANISM: Artificial
```

```
<220> FEATURE:
<223> OTHER INFORMATION: Synthetic peptide sequence

<400> SEQUENCE: 41

Arg Gly Asp Tyr Arg Tyr Asp Tyr Ala Pro Thr Ala Gln Glu Ala Gly
1               5                   10                  15

Glu Gly Pro Arg Tyr Asp Tyr Arg Gly Asp Tyr
            20                  25

<210> SEQ ID NO 42
<211> LENGTH: 27
<212> TYPE: PRT
<213> ORGANISM: Artificial
<220> FEATURE:
<223> OTHER INFORMATION: Synthetic peptide sequence

<400> SEQUENCE: 42

Arg Gly Asp Tyr Arg Tyr Asp Tyr Pro Thr Ile Ser Gln Glu Leu Gly
1               5                   10                  15

Gln Arg Pro Arg Tyr Asp Tyr Arg Gly Asp Tyr
            20                  25

<210> SEQ ID NO 43
<211> LENGTH: 27
<212> TYPE: PRT
<213> ORGANISM: Artificial
<220> FEATURE:
<223> OTHER INFORMATION: Synthetic peptide sequence

<400> SEQUENCE: 43

Arg Gly Asp Tyr Arg Tyr Asp Tyr Pro Thr Val Ser Gln Glu Leu Gly
1               5                   10                  15

Gln Arg Pro Arg Tyr Asp Tyr Arg Gly Asp Tyr
            20                  25

<210> SEQ ID NO 44
<211> LENGTH: 39
<212> TYPE: DNA
<213> ORGANISM: Artificial
<220> FEATURE:
<223> OTHER INFORMATION: Synthetic oligonucleotide

<400> SEQUENCE: 44
actgctggat cgtatgcgta gtctggacgt ctaccgtgt                      39

<210> SEQ ID NO 45
<211> LENGTH: 26
<212> TYPE: DNA
<213> ORGANISM: Artificial
<220> FEATURE:
<223> OTHER INFORMATION: Synthetic oligonucleotide

<400> SEQUENCE: 45
cagtgcaggc tacgcatacc atccag                                    26

<210> SEQ ID NO 46
<211> LENGTH: 26
<212> TYPE: DNA
<213> ORGANISM: Artificial
<220> FEATURE:
<223> OTHER INFORMATION: Synthetic oligonucleotide

<400> SEQUENCE: 46
actgacacgg tagacgtcca gcctgc                                    26
```

```
<210> SEQ ID NO 47
<211> LENGTH: 4
<212> TYPE: DNA
<213> ORGANISM: Artificial
<220> FEATURE:
<223> OTHER INFORMATION: Synthetic oligonucleotide

<400> SEQUENCE: 47 actg                                                                       4

<210> SEQ ID NO 48
<211> LENGTH: 4
<212> TYPE: DNA
<213> ORGANISM: Artificial
<220> FEATURE:
<223> OTHER INFORMATION: Synthetic oligonucleotide

<400> SEQUENCE: 48 cagt                                                                       4

<210> SEQ ID NO 49
<211> LENGTH: 16
<212> TYPE: DNA
<213> ORGANISM: Artificial
<220> FEATURE:
<223> OTHER INFORMATION: Synthetic oligonucleotide

<400> SEQUENCE: 49
ctggatcgta tgcgta                                                         16

<210> SEQ ID NO 50
<211> LENGTH: 7
<212> TYPE: DNA
<213> ORGANISM: Artificial
<220> FEATURE:
<223> OTHER INFORMATION: Synthetic oligonucleotide

<400> SEQUENCE: 50 gcaggct                                                                    7

<210> SEQ ID NO 51
<211> LENGTH: 16
<212> TYPE: DNA
<213> ORGANISM: Artificial
<220> FEATURE:
<223> OTHER INFORMATION: Synthetic oligonucleotide

<400> SEQUENCE: 51
acacggtaga cgtcca                                                         16

<210> SEQ ID NO 52
<211> LENGTH: 3
<212> TYPE: DNA
<213> ORGANISM: Artificial
<220> FEATURE:
<223> OTHER INFORMATION: Synthetic oligonucleotide

<400> SEQUENCE: 52 gtc                                                                        3

<210> SEQ ID NO 53
<211> LENGTH: 16
<212> TYPE: DNA
<213> ORGANISM: Artificial
<220> FEATURE:
<223> OTHER INFORMATION: Synthetic oligonucleotide

<400> SEQUENCE: 53
```
tggacgtcta ccgtgt                                                      16

<210> SEQ ID NO 54
<211> LENGTH: 15
<212> TYPE: DNA
<213> ORGANISM: Artificial
<220> FEATURE:
<223> OTHER INFORMATION: Synthetic oligonucleotide

<400> SEQUENCE: 54
acgcatacca tccag                                                       15

<210> SEQ ID NO 55
<211> LENGTH: 6
<212> TYPE: DNA
<213> ORGANISM: Artificial
<220> FEATURE:
<223> OTHER INFORMATION: Synthetic oligonucleotide

<400> SEQUENCE: 55 gcctgc                                                                  6

<210> SEQ ID NO 56
<211> LENGTH: 30
<212> TYPE: DNA
<213> ORGANISM: Artificial
<220> FEATURE:
<223> OTHER INFORMATION: Synthetic oligonucleotide

<400> SEQUENCE: 56
tcgaaggctg attcggttag tccatgagtc                                       30

<210> SEQ ID NO 57
<211> LENGTH: 30
<212> TYPE: DNA
<213> ORGANISM: Artificial
<220> FEATURE:
<223> OTHER INFORMATION: Synthetic oligonucleotide

<400> SEQUENCE: 57
aattgactca tggactatca tgcggatcca                                       30

<210> SEQ ID NO 58
<211> LENGTH: 30
<212> TYPE: DNA
<213> ORGANISM: Artificial
<220> FEATURE:
<223> OTHER INFORMATION: Synthetic oligonucleotide

<400> SEQUENCE: 58
agcttggatc cgcatgacat tcgccgtaag                                       30

<210> SEQ ID NO 59
<211> LENGTH: 30
<212> TYPE: DNA
<213> ORGANISM: Artificial
<220> FEATURE:
<223> OTHER INFORMATION: Synthetic oligonucleotide

<400> SEQUENCE: 59
gatccttacg gcgaatgacc gaatcagcct                                       30

<210> SEQ ID NO 60
<211> LENGTH: 4
<212> TYPE: DNA
<213> ORGANISM: Artificial

```
<220> FEATURE:
<223> OTHER INFORMATION: Synthetic oligonucleotide

<400> SEQUENCE: 60 tcga                                                                       4

<210> SEQ ID NO 61
<211> LENGTH: 4
<212> TYPE: DNA
<213> ORGANISM: Artificial
<220> FEATURE:
<223> OTHER INFORMATION: Synthetic oligonucleotide

<400> SEQUENCE: 61 aatt                                                                       4

<210> SEQ ID NO 62
<211> LENGTH: 4
<212> TYPE: DNA
<213> ORGANISM: Artificial
<220> FEATURE:
<223> OTHER INFORMATION: Synthetic oligonucleotide

<400> SEQUENCE: 62 agct                                                                       4

<210> SEQ ID NO 63
<211> LENGTH: 4
<212> TYPE: DNA
<213> ORGANISM: Artificial
<220> FEATURE:
<223> OTHER INFORMATION: Synthetic oligonucleotide

<400> SEQUENCE: 63 gatc                                                                       4

<210> SEQ ID NO 64
<211> LENGTH: 13
<212> TYPE: DNA
<213> ORGANISM: Artificial
<220> FEATURE:
<223> OTHER INFORMATION: Synthetic oligonucleotide

<400> SEQUENCE: 64
aggctgattc ggt                                                            13

<210> SEQ ID NO 65
<211> LENGTH: 13
<212> TYPE: DNA
<213> ORGANISM: Artificial
<220> FEATURE:
<223> OTHER INFORMATION: Synthetic oligonucleotide

<400> SEQUENCE: 65
gactcatgga cta                                                            13

<210> SEQ ID NO 66
<211> LENGTH: 13
<212> TYPE: DNA
<213> ORGANISM: Artificial
<220> FEATURE:
<223> OTHER INFORMATION: Synthetic oligonucleotide

<400> SEQUENCE: 66
tggatccgca tga                                                            13
```

-continued

```
<210> SEQ ID NO 67
<211> LENGTH: 13
<212> TYPE: DNA
<213> ORGANISM: Artificial
<220> FEATURE:
<223> OTHER INFORMATION: Synthetic oligonucleotide

<400> SEQUENCE: 67
cttacggcga atg                                                          13

<210> SEQ ID NO 68
<211> LENGTH: 13
<212> TYPE: DNA
<213> ORGANISM: Artificial
<220> FEATURE:
<223> OTHER INFORMATION: Synthetic oligonucleotide

<400> SEQUENCE: 68
tagtccatga gtc                                                          13

<210> SEQ ID NO 69
<211> LENGTH: 13
<212> TYPE: DNA
<213> ORGANISM: Artificial
<220> FEATURE:
<223> OTHER INFORMATION: Synthetic oligonucleotide

<400> SEQUENCE: 69
tcatgcggat cca                                                          13

<210> SEQ ID NO 70
<211> LENGTH: 13
<212> TYPE: DNA
<213> ORGANISM: Artificial
<220> FEATURE:
<223> OTHER INFORMATION: Synthetic oligonucleotide

<400> SEQUENCE: 70
cattcgccgt aag                                                          13

<210> SEQ ID NO 71
<211> LENGTH: 13
<212> TYPE: DNA
<213> ORGANISM: Artificial
<220> FEATURE:
<223> OTHER INFORMATION: Synthetic oligonucleotide

<400> SEQUENCE: 71
accgaatcag cct                                                          13

<210> SEQ ID NO 72
<211> LENGTH: 30
<212> TYPE: DNA
<213> ORGANISM: Artificial
<220> FEATURE:
<223> OTHER INFORMATION: Synthetic oligonucleotide

<400> SEQUENCE: 72
tgactggatc cgcatgacat tcgccgtaag                                        30

<210> SEQ ID NO 73
<211> LENGTH: 30
<212> TYPE: DNA
<213> ORGANISM: Artificial
<220> FEATURE:
<223> OTHER INFORMATION: Synthetic oligonucleotide

<400> SEQUENCE: 73
```
gtcatggatc cgcatgacat tcgccgtaag         30

<210> SEQ ID NO 74
<211> LENGTH: 30
<212> TYPE: DNA
<213> ORGANISM: Artificial
<220> FEATURE:
<223> OTHER INFORMATION: Synthetic oligonucleotide

<400> SEQUENCE: 74
atcgtggatc cgcatgacat tcgccgtaag         30

<210> SEQ ID NO 75
<211> LENGTH: 30
<212> TYPE: DNA
<213> ORGANISM: Artificial
<220> FEATURE:
<223> OTHER INFORMATION: Synthetic oligonucleotide

<400> SEQUENCE: 75
atgctggatc cgcatgacat tcgccgtaag         30

<210> SEQ ID NO 76
<211> LENGTH: 30
<212> TYPE: DNA
<213> ORGANISM: Artificial
<220> FEATURE:
<223> OTHER INFORMATION: Synthetic oligonucleotide

<400> SEQUENCE: 76
gcaatggatc cgcatgacat tcgccgtaag         30

<210> SEQ ID NO 77
<211> LENGTH: 30
<212> TYPE: DNA
<213> ORGANISM: Artificial
<220> FEATURE:
<223> OTHER INFORMATION: Synthetic oligonucleotide

<400> SEQUENCE: 77
tgaccttacg gcgaatgacc gaatcagcct         30

<210> SEQ ID NO 78
<211> LENGTH: 30
<212> TYPE: DNA
<213> ORGANISM: Artificial
<220> FEATURE:
<223> OTHER INFORMATION: Synthetic oligonucleotide

<400> SEQUENCE: 78
cgatcttacg gcgaatgacc gaatcagcct         30

<210> SEQ ID NO 79
<211> LENGTH: 30
<212> TYPE: DNA
<213> ORGANISM: Artificial
<220> FEATURE:
<223> OTHER INFORMATION: Synthetic oligonucleotide

<400> SEQUENCE: 79
gcatcttacg gcgaatgacc gaatcagcct         30

<210> SEQ ID NO 80
<211> LENGTH: 30
<212> TYPE: DNA
<213> ORGANISM: Artificial

```
<220> FEATURE:
<223> OTHER INFORMATION: Synthetic oligonucleotide

<400> SEQUENCE: 80
ttgccttacg gcgaatgacc gaatcagcct                                              30

<210> SEQ ID NO 81
<211> LENGTH: 30
<212> TYPE: DNA
<213> ORGANISM: Artificial
<220> FEATURE:
<223> OTHER INFORMATION: Synthetic oligonucleotide

<400> SEQUENCE: 81
ggatcttacg gcgaatgacc gaatcagcct                                              30

<210> SEQ ID NO 82
<211> LENGTH: 30
<212> TYPE: DNA
<213> ORGANISM: Artificial
<220> FEATURE:
<223> OTHER INFORMATION: Synthetic oligonucleotide

<400> SEQUENCE: 82
tgacaggctg attcggttca tgcggatcca                                              30

<210> SEQ ID NO 83
<211> LENGTH: 30
<212> TYPE: DNA
<213> ORGANISM: Artificial
<220> FEATURE:
<223> OTHER INFORMATION: Synthetic oligonucleotide

<400> SEQUENCE: 83
cgataggctg attcggttca tgcggatcca                                              30

<210> SEQ ID NO 84
<211> LENGTH: 30
<212> TYPE: DNA
<213> ORGANISM: Artificial
<220> FEATURE:
<223> OTHER INFORMATION: Synthetic oligonucleotide

<400> SEQUENCE: 84
gcataggctg attcggttca tgcggatcca                                              30

<210> SEQ ID NO 85
<211> LENGTH: 30
<212> TYPE: DNA
<213> ORGANISM: Artificial
<220> FEATURE:
<223> OTHER INFORMATION: Synthetic oligonucleotide

<400> SEQUENCE: 85
ttgcaggctg attcggttca tgcggatcca                                              30

<210> SEQ ID NO 86
<211> LENGTH: 30
<212> TYPE: DNA
<213> ORGANISM: Artificial
<220> FEATURE:
<223> OTHER INFORMATION: Synthetic oligonucleotide

<400> SEQUENCE: 86
ggataggctg attcggttca tgcggatcca                                              30
```

```
<210> SEQ ID NO 87
<211> LENGTH: 4
<212> TYPE: DNA
<213> ORGANISM: Artificial
<220> FEATURE:
<223> OTHER INFORMATION: Synthetic oligonucleotide

<400> SEQUENCE: 87 tgac                                                                    4

<210> SEQ ID NO 88
<211> LENGTH: 4
<212> TYPE: DNA
<213> ORGANISM: Artificial
<220> FEATURE:
<223> OTHER INFORMATION: Synthetic oligonucleotide

<400> SEQUENCE: 88 gtca                                                                    4

<210> SEQ ID NO 89
<211> LENGTH: 4
<212> TYPE: DNA
<213> ORGANISM: Artificial
<220> FEATURE:
<223> OTHER INFORMATION: Synthetic oligonucleotide

<400> SEQUENCE: 89 cgat                                                                    4

<210> SEQ ID NO 90
<211> LENGTH: 4
<212> TYPE: DNA
<213> ORGANISM: Artificial
<220> FEATURE:
<223> OTHER INFORMATION: Synthetic oligonucleotide

<400> SEQUENCE: 90 atcg                                                                    4

<210> SEQ ID NO 91
<211> LENGTH: 4
<212> TYPE: DNA
<213> ORGANISM: Artificial
<220> FEATURE:
<223> OTHER INFORMATION: Synthetic oligonucleotide

<400> SEQUENCE: 91 gcat                                                                    4

<210> SEQ ID NO 92
<211> LENGTH: 4
<212> TYPE: DNA
<213> ORGANISM: Artificial
<220> FEATURE:
<223> OTHER INFORMATION: Synthetic oligonucleotide

<400> SEQUENCE: 92 atgc                                                                    4

<210> SEQ ID NO 93
<211> LENGTH: 4
<212> TYPE: DNA
<213> ORGANISM: Artificial
<220> FEATURE:
<223> OTHER INFORMATION: Synthetic oligonucleotide

<400> SEQUENCE: 93
```

```
ttgc                                                                  4

<210> SEQ ID NO 94
<211> LENGTH: 4
<212> TYPE: DNA
<213> ORGANISM: Artificial
<220> FEATURE:
<223> OTHER INFORMATION: Synthetic oligonucleotide

<400> SEQUENCE: 94 gcaa                                                                  4

<210> SEQ ID NO 95
<211> LENGTH: 4
<212> TYPE: DNA
<213> ORGANISM: Artificial
<220> FEATURE:
<223> OTHER INFORMATION: Synthetic oligonucleotide

<400> SEQUENCE: 95 ggat                                                                  4

<210> SEQ ID NO 96
<211> LENGTH: 13
<212> TYPE: DNA
<213> ORGANISM: Artificial
<220> FEATURE:
<223> OTHER INFORMATION: Synthetic oligonucleotide

<400> SEQUENCE: 96
tggatccgca tga                                                       13

<210> SEQ ID NO 97
<211> LENGTH: 13
<212> TYPE: DNA
<213> ORGANISM: Artificial
<220> FEATURE:
<223> OTHER INFORMATION: Synthetic oligonucleotide

<400> SEQUENCE: 97
cattcgccgt aag                                                       13

<210> SEQ ID NO 98
<211> LENGTH: 13
<212> TYPE: DNA
<213> ORGANISM: Artificial
<220> FEATURE:
<223> OTHER INFORMATION: Synthetic oligonucleotide

<400> SEQUENCE: 98
cttacggcga atg                                                       13

<210> SEQ ID NO 99
<211> LENGTH: 13
<212> TYPE: DNA
<213> ORGANISM: Artificial
<220> FEATURE:
<223> OTHER INFORMATION: Synthetic oligonucleotide

<400> SEQUENCE: 99
accgaatcag cct                                                       13

<210> SEQ ID NO 100
<211> LENGTH: 13
<212> TYPE: DNA
<213> ORGANISM: Artificial
```

```
<220> FEATURE:
<223> OTHER INFORMATION: Synthetic oligonucleotide

<400> SEQUENCE: 100
aggctgattc ggt                                                          13

<210> SEQ ID NO 101
<211> LENGTH: 13
<212> TYPE: DNA
<213> ORGANISM: Artificial
<220> FEATURE:
<223> OTHER INFORMATION: Synthetic oligonucleotide

<400> SEQUENCE: 101
tcatgcggat cca                                                          13

<210> SEQ ID NO 102
<211> LENGTH: 30
<212> TYPE: DNA
<213> ORGANISM: Artificial
<220> FEATURE:
<223> OTHER INFORMATION: Synthetic oligonucleotide

<400> SEQUENCE: 102
ttgctggatc cgcatgacat tcgccgtaag                                        30

<210> SEQ ID NO 103
<211> LENGTH: 30
<212> TYPE: DNA
<213> ORGANISM: Artificial
<220> FEATURE:
<223> OTHER INFORMATION: Synthetic oligonucleotide

<400> SEQUENCE: 103
cgtttggatc cgcatgacat tcgccgtaag                                        30

<210> SEQ ID NO 104
<211> LENGTH: 30
<212> TYPE: DNA
<213> ORGANISM: Artificial
<220> FEATURE:
<223> OTHER INFORMATION: Synthetic oligonucleotide

<400> SEQUENCE: 104
atgctggatc cgcatgacat tcgccgtaag                                        30

<210> SEQ ID NO 105
<211> LENGTH: 26
<212> TYPE: DNA
<213> ORGANISM: Artificial
<220> FEATURE:
<223> OTHER INFORMATION: Synthetic oligonucleotide

<400> SEQUENCE: 105
tggatccgca tgacattcgc cgtaag                                            26

<210> SEQ ID NO 106
<211> LENGTH: 30
<212> TYPE: DNA
<213> ORGANISM: Artificial
<220> FEATURE:
<223> OTHER INFORMATION: Synthetic oligonucleotide

<400> SEQUENCE: 106
gcatcttacg gcgaatgacc gaatcagcct                                        30
```

```
<210> SEQ ID NO 107
<211> LENGTH: 30
<212> TYPE: DNA
<213> ORGANISM: Artificial
<220> FEATURE:
<223> OTHER INFORMATION: Synthetic oligonucleotide

<400> SEQUENCE: 107
gcaacttacg gcgaatgacc gaatcagcct                                      30

<210> SEQ ID NO 108
<211> LENGTH: 26
<212> TYPE: DNA
<213> ORGANISM: Artificial
<220> FEATURE:
<223> OTHER INFORMATION: Synthetic oligonucleotide

<400> SEQUENCE: 108
cttacggcga atgaccgaat cagcct                                          26

<210> SEQ ID NO 109
<211> LENGTH: 30
<212> TYPE: DNA
<213> ORGANISM: Artificial
<220> FEATURE:
<223> OTHER INFORMATION: Synthetic oligonucleotide

<400> SEQUENCE: 109
gcataggctg attcggttca tgcggatcca                                      30

<210> SEQ ID NO 110
<211> LENGTH: 30
<212> TYPE: DNA
<213> ORGANISM: Artificial
<220> FEATURE:
<223> OTHER INFORMATION: Synthetic oligonucleotide

<400> SEQUENCE: 110
ttgcaggctg attcggttca tgcggatcca                                      30

<210> SEQ ID NO 111
<211> LENGTH: 30
<212> TYPE: DNA
<213> ORGANISM: Artificial
<220> FEATURE:
<223> OTHER INFORMATION: Synthetic oligonucleotide

<400> SEQUENCE: 111
aacgaggctg attcggttca tgcggatcca                                      30

<210> SEQ ID NO 112
<211> LENGTH: 26
<212> TYPE: DNA
<213> ORGANISM: Artificial
<220> FEATURE:
<223> OTHER INFORMATION: Synthetic oligonucleotide

<400> SEQUENCE: 112
aggctgattc ggttcatgcg gatcca                                          26

<210> SEQ ID NO 113
<211> LENGTH: 36
<212> TYPE: DNA
<213> ORGANISM: Artificial
<220> FEATURE:
<223> OTHER INFORMATION: Synthetic oligonucleotide

<400> SEQUENCE: 113
```
cgaccgatga atagcggtca gatccgtacc tactcg                          36

<210> SEQ ID NO 114
<211> LENGTH: 36
<212> TYPE: DNA
<213> ORGANISM: Artificial
<220> FEATURE:
<223> OTHER INFORMATION: Synthetic oligonucleotide

<400> SEQUENCE: 114
cgagtaggta cggatctgcg tattgcgaac gactcg                          36

<210> SEQ ID NO 115
<211> LENGTH: 36
<212> TYPE: DNA
<213> ORGANISM: Artificial
<220> FEATURE:
<223> OTHER INFORMATION: Synthetic oligonucleotide

<400> SEQUENCE: 115
cgagtcgttc gcaatacggc tgtacgtatg gtctcg                          36

<210> SEQ ID NO 116
<211> LENGTH: 36
<212> TYPE: DNA
<213> ORGANISM: Artificial
<220> FEATURE:
<223> OTHER INFORMATION: Synthetic oligonucleotide

<400> SEQUENCE: 116
cgagaccata cgtacagcac cgctattcat cggtcg                          36

<210> SEQ ID NO 117
<211> LENGTH: 36
<212> TYPE: DNA
<213> ORGANISM: Artificial
<220> FEATURE:
<223> OTHER INFORMATION: Synthetic oligonucleotide

<400> SEQUENCE: 117
cgaccgatga atagcggtca gatccgtacc tactcg                          36

<210> SEQ ID NO 118
<211> LENGTH: 36
<212> TYPE: DNA
<213> ORGANISM: Artificial
<220> FEATURE:
<223> OTHER INFORMATION: Synthetic oligonucleotide

<400> SEQUENCE: 118
cgagtcgttc gcaatacgac cgctattcat cggtcg                          36

<210> SEQ ID NO 119
<211> LENGTH: 36
<212> TYPE: DNA
<213> ORGANISM: Artificial
<220> FEATURE:
<223> OTHER INFORMATION: Synthetic oligonucleotide

<400> SEQUENCE: 119
cgagtaggta cggatctgcg tattgcgaac gactcg                          36

<210> SEQ ID NO 120
<211> LENGTH: 36
<212> TYPE: DNA
<213> ORGANISM: Artificial

```
<220> FEATURE:
<223> OTHER INFORMATION: Synthetic oligonucleotide

<400> SEQUENCE: 120
cgacagctga ctagagtcac gacctgtacc tactcg                                   36

<210> SEQ ID NO 121

<400> SEQUENCE: 121

000

<210> SEQ ID NO 122
<211> LENGTH: 36
<212> TYPE: DNA
<213> ORGANISM: Artificial
<220> FEATURE:
<223> OTHER INFORMATION: Synthetic oligonucleotide

<400> SEQUENCE: 122
cgagtaggta caggtcgtcg tcttgagaac gactcg                                   36
```

NUCLEIC ACID-BASED MATRIXES

CROSS-REFERENCE TO RELATED APPLICATIONS

The present application claims priority to U.S. Provisional Application Ser. Nos. 60/722,032, filed Sep. 29, 2005, 60/783,422, filed Mar. 17, 2006, 60/783,426, filed Mar. 17, 2006, 60/707,431, filed Aug. 11, 2005, 60/745,383, filed Apr. 21, 2006 and 60/756,453, filed Jan. 5, 2006, the disclosure of each of which is incorporated herein by reference in its entirety. Applicants claim the benefits of these applications under 35 U.S.C. §119(e) and/or 35 U.S.C. §120.

FIELD OF THE INVENTION

The field of the invention is nucleic acid-based polymeric structures and the use thereof.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

A key aim of biotechnology and nanotechnology is the construction of new biomaterials, including individual geometrical objects, nanomechanical devices, and extended constructions that permit the fabrication of intricate structures of materials to serve many practical purposes (Feynman et al., *Miniaturization* 282-296 (1961); Drexler, *Proc. Nat. Acad. Sci. (USA)* 78:5275-5278 (1981); Robinson et al., *Prot Eng* 1 295-300 (1987); Seeman, *DNA & Cell Biol.* 10:475-486 (1991); Seeman, *Nanotechnol.* 2:149-159 (1991)). Molecules of biological systems, for example, nucleic acids, have the potential to serve as building blocks for these constructions due to their self and programmable-assembly capabilities.

Nucleic acid molecules possess a distinct set of mechanical, physical, and chemical properties. From a mechanical point of view, nucleic acid molecules can be rigid (e.g., when DNA molecules are less than 50 nm, the persistent length of double stranded DNA (Bouchiat, C. et al., *Biophys J* 76:409-13 (1999); Tinland et al., *Macromolecules* 30:5763-5765 (1997); Toth et al., *Biochemistry* 37:8173-9 (1998)), or flexible. Physically, nucleic acid molecules are small, with a width of about 2 nanometers and a length of about 0.34 nanometers per basepair (e.g., B-DNA). In nature, nucleic acid molecules (i.e., RNA and DNA) can be found in either linear, double stranded or circular shapes. Chemically, DNA is generally stable, non-toxic, water soluble, and is commercially available in large quantities and in high purity. Unlike DNA, RNA is almost always a single-stranded molecule and has a much shorter chain of nucleotides. RNA contains ribose, rather than the deoxyribose found in DNA (there is a hydroxyl group attached to the pentose ring in the 2' position whereas DNA has a hydrogen atom rather than a hydroxyl group). This hydroxyl group makes RNA less stable than DNA because it is more prone to hydrolysis. However, several types of RNA (tRNA, rRNA) contain a great deal of secondary structure, which help promote stability. In addition, RNA can be modified with various chemical modifiers known in the art to stabilize the molecules. Analogous molecules with modified backbones have been designed which change various characteristics of RNA, such as its instability to degradative enzymes. Some alternative antisense structural types are phosphorothioate, Morpholino, PNA (peptide nucleic acid), LNA (locked nucleic acid), TNA (treose nucleic acid) and 2'-O alkyl oligos. Some antisense structural types are being experimentally applied as antisense therapy, with at least one antisense therapy approved for use in humans.

Moreover, nucleic acid molecules are easily and highly manipulable by various well-known enzymes such as restriction enzymes, ligases and nucleases. Also, under proper conditions, nucleic acid molecules will self-assemble with complementary strands of nucleic acid (e.g., DNA, RNA, or Peptide Nucleic Acid, (PNA)). Furthermore, nucleic acid molecules can be amplified exponentially and ligated specifically. Thus, nucleic acid molecules are an excellent candidate for constructing nano-material and macro-material for use in biotechnology or medicine.

The concept of using nucleic acid molecules for non-genetic application has only recently emerged, such as in DNA-computation, where DNA are utilized in algorithms for solving combinatorial problems (Adleman, *Science* 266:1021-4 (1994); Guarnieri et al., *Science* 273:220-3 (1996); Ouyang et al., *Science* 278:446-9 (1997); Sakamoto et al., *Science* 288:1223-6 (2000); Benenson et al., *Nature* 414:430-4 (2001)), and DNA-nanotechnology, such as using DNA molecules for nano-scaled frameworks and scaffolds (Niemeyer, *Applied Physics a-Materials Science & Processing* 68:119-124 (1999); Seeman, *Annual Review of Biophysics and Biomolecular Structure* 27:225-248 (1998)). However, the design and production of DNA-based materials is still problematic (Mao et al., *Nature* 397:144-146 (1999); Seeman et al., *Proc Natl Acad Sci USA* 99:6451-6455 (2002); Yan et al., *Nature* 415:62-5 (2002); Mirkin et al., *Nature* 382:607-9 (1996); Watson et al., *J Am Chem Soc* 123:5592-3 (2001)). For example, nucleic acid structures are quite polydispersed with flexible arms and self-ligated circular and non-circular byproducts (Ma et al., *Nucleic Acids Res* 14:9745-53 (1986); Wang et al., *Journal of the American Chemical Society* 120:8281-8282 (1998); Nilsen et al., *J Theor Biol* 187:273-84 (1997)), which severely limits their utility in constructing DNA materials. Furthermore, the building blocks and motifs employed thus far are isotropic and multivalent, possibly useful for growing nano-scaled arrays and scaffolds (Winfree et al., *Nature* 394:539-44 (1998); Niemeyer, *Applied Physics a-Materials Science & Processing* 68:119-124 (1999); Seeman, *Annual Review of Biophysics and Biomolecular Structure* 27:225-248 (1998)), but not suitable for controlled growth, such as in dendrimer, or in creating a large quantity of monodispersed new materials, which are important to realize nucleic acid-based materials.

Other schemes of nano-construction using linear DNA molecules include a biotin-avidin based DNA network (Luo, "Novel Crosslinking Technologies to Assess Protein-DNA Binding and DNA-DNA Complexes for Gene Delivery and Expression" (Dissertation). Molecular, Cellular, and Developmental Biology Program, The Ohio State University (1997)), nanocrystals (Alivisatos et al., *Nature* 382:609-11 (1996)), DNA-protein nanocomplexes (Niemeyer et al., *Angewandte Chemie-International Edition* 37:2265-2268 (1998)), a DNA-fueled molecular machine (Yurke et al., *Nature* 406:605-8 (2000)), DNA-block copolymer conjugates (Watson et al., *J Am Chem Soc* 123:5592-3 (2001)), DNA-silver-wire (Braun et al., *Nature* 391:775-8 (1998)), and DNA-mediated supramolecular structures (Taton et al., *Journal of the American Chemical Society* 122:6305-6306 (2000)), DNA sensing via gold nanoparticles (Elghanian et al., *Science* 277:1078-81 (1997)), Y-shape DNA molecules (Eckardt et al., *Nature* 420:286 (2002)) and DNA patterning via dip-pen nanolithography (Demers et al., *Science* 296: 1836-8 (2002)). However, the preceding prior art DNA-based structures are not suitable for large scale production and are further limited to linear DNA.

Matrixes formed from various polymers are important biomaterials useful in many biomedical applications, including controlled drug delivery and tissue engineering. Biomacromolecules including proteins are great precursors for novel hydrogels. For example, hydrogels made from peptides and proteins have already been recognized as smart materials (Petka et al., Science 281, 389 (1998); Zhang et al., *J Am Chem Soc* 127, 10136 (2005); J. Kisiday et al., *Proc Natl Acad Sci USA* 99, 9996 (2002); T. Amiya, T. Tanaka, *Macromolecules* 20, 1162 (1987); A. P. Nowak et al., *Nature* 417, 424 (2002); J. P. Schneider et al., *J Am Chem Soc* 124, 15030 (2002)), cell culture composition (S. Zhang et al., *Biomaterials* 16, 1385 (1995)) and artificial tissues (Lutolf et al., *Nat Biotechnol* 23, 47 (2005)).

However, there are still many limitations to protein hydrogels including the fact that the protein used is usually very expensive, the difficulty of designing and generating a primary amino acid sequence with a predictable structure, and the obvious immunogenecities of most proteins. Nucleic acid molecules, on the other hand, possess remarkable physical and chemical properties making it an ideal polymer. A large number of molecular tools also exist that can manipulate nucleic acid molecules at angstrom precision with enzymatic efficiency. For example, linear DNA was first used to construct an artificial nano-structure (Chen et al., *Nature* 350, 631 (1991)). Using "double crossover" DNA (two crossovers connecting two helical domains), a variety of geometric objects, periodic arrays and nanoscale mechanical devices have been constructed (Yan et al., *Nature* 415, 62 (2002); Yan et al., *Science* 301, 1882 (2003); Seeman, *Trends Biochem Sci* 30, 119 (2005); Pinto et al., *Nano Lett* 5, 2399 (2005)). Recently Lin et al. used a linear DNA molecule as a cross-linker to construct a thermal-stimulative polyacrylamide hydrogel, creating a DNA-polymer hybrid hydrogel system (Lin et al., *J Biomech Eng* 126, 104 (2004)). In addition, nucleic acid molecules have been conjugated with other chemical moieties, thus effectively linking diverse chemical functionalities (Zhu et al., *J Am Chem Soc* 125, 10178 (2003)).

A matrix structure or scaffold composed of synthetic nucleic acid molecules with or without any other chemical moieties has not been reported, which matrix would provide much better control in design and synthesis, higher biocompatibility, and better cost effectiveness. A key component for creating a nucleic acid matrix is cross-linkable nucleic acid monomers (building blocks), which cannot be realized by linear nucleic acid molecules. Branched and dendrimer-like DNA are known in the art (Y. Li et al., *Nat Materials* 3, 38 (2004); Li et al., *Nat Biotechnol* 23, 885 (2005)).

An important application for matrixes composed of nucleic acid molecules is controlled delivery of bioactive agents to a cell or organism. A major challenge in delivery of therapeutic agents is controlled temporal delivery of therapeutic agents (e.g., drugs or growth factors). Accordingly, it would be an advance in the art to provide controlled therapy that is free from undesirable complications ascribed to protein matrices. Furthermore, controlled drug delivery using chemical polymer compounds often results in batch to batch variance and is not reliably predictable with regards to pore size and geometrical pattern, thus not all issues have been completely resolved. In applications where a drug is incorporated into a degradable structure to control delivery, it is necessary to ensure that the degradation products of the structure do not interfere with the drug being delivered. Furthermore, it can be difficult to control the drug release rate by controlling the degradation process. For example, in cases where a porous polymer layer is used to hold drugs and/or to control the delivery rate, the delivery rate can depend sensitively on parameters of the porous layer (e.g., porosity, mean pore size, degradation rate) which are imperfectly controlled during fabrication. For example, two membranes made in different ways (or by different manufacturers) may have different drug delivery properties even if they nominally have the same pore size and porosity. Therefore, there is a need for new biomaterials, such as nucleic acid-based matrixes so as to provide a new and tremendous advantage in drug delivery, in vitro or ex vivo cell-based applications or therapies. In this regard nucleic acid-based matrixes have yet to be successfully exploited.

Another important application of nucleic acid based matrixes is cell-free protein production. Nucleic acid-based matrixes have simply not been contemplated in the prior art, for utilization in cell-free protein production. The in vitro synthesis of proteins is an important tool for molecular biologists and has a variety of applications, including the rapid identification of gene products (e.g., proteomics), localization of mutations through synthesis of truncated gene products, protein folding studies, and incorporation of modified or unnatural amino acids for functional studies. The use of in vitro translation systems can have advantages over in vivo gene expression when the over-expressed product is toxic to the host cell, when the product is insoluble or forms inclusion bodies, or when the protein undergoes rapid proteolysis by intracellular proteases.

A substantial problem with recombinant systems is post-expression purification. Expressed recombinant proteins must be purified away from the entire host's lysates, which contain cell debris, lipids, carbohydrates, nucleic acids, and other proteins. It is still a great challenge to purify expressed proteins while keeping the protein activity high and the total cost down. In addition, there is a high cost and the danger associated with living organisms, e.g., production of toxins. Moreover, expensive media, serum, fermentaters, reactors, etc. are needed to maintain hosts. In addition, keeping batch to batch consistency for expressed recombinant protein within living organisms has proved to be difficult and expensive. Once a production process is established, it is almost impossible to improve it with living organisms, further increasing the final cost. Moreover, there also exists the danger of potential contamination by pathogen bacteria or viruses.

In practice, only a few cell-free systems have been developed for in vitro protein synthesis. In general, systems known in the art are derived from cells engaged in a high rate of protein synthesis. Such cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.). There are two approaches to in vitro protein synthesis based on the starting genetic material: RNA or DNA. Standard translation systems, such as reticulocyte lysates and wheat germ extracts, use RNA as a template; whereas "coupled" and "linked" systems start with DNA templates, which are transcribed into RNA then translated.

RNA is transcribed from the DNA and subsequently translated without any purification. Such systems typically combine a prokaryotic phage RNA polymerase and promoter (T7, T3, or SP6) with eukaryotic or prokaryotic extracts to synthesize proteins from exogenous DNA templates. DNA templates for transcription:translation reactions may be cloned into plasmid vectors or generated by PCR. The "linked" system is a two-step reaction, based on transcription with a bacteriophage polymerase followed by translation in the rabbit reticulocyte lysate or wheat germ lysate. Because the transcription and translation reactions are separate, each can be optimized to ensure that both are functioning at their full potential. Conversely, many commercially available eukaryotic coupled transcription:translation systems have compromised one or both reactions so that they can occur in a single tube. Thus, yield is sacrificed for convenience.

Notably, the protein production systems in the prior are fundamentally limited solution-based systems. In addition, such solution based systems provide very limited production levels (e.g., yield of the protein of interest is at best about 750 µg/ml; Invitrogen). Indeed, none of the prior art systems utilize nucleic acid-based matrixes to produce proteins. Therefore, there is a clear need for an efficient and robust cell-free protein production system.

Therefore there is a need for new biomaterials that have applications in diverse areas of biotechnology and medicine. The present invention provides compositions and methods that provide nucleic acid-based matrixes useful in biotechnology and medicine.

SUMMARY OF THE INVENTION

The nucleic acid-based matrixes disclosed can be utilized in delivery of biologically active agents, delivery or propagation of cells, three-dimensional cell culture or in vivo cell growth, such as in cell therapy or tissue engineering, utilization in wound-dressing, and applications in cell-free protein production and/or modification.

In some embodiments, the nucleic acid based matrixes are composed of nucleic acid molecules of different shapes. Such nucleic acid molecules are branched nucleic acids that are X-, Y-, T-, or dumbbell shaped (collectively referred to as "multimers" or a "multimer"). Branched nucleic acid molecules are also dendrimer-like, can form dendrimers and are also referred to as dendrimer-like nucleic acid molecules (DL-NAMs). In some embodiments, the multimers form a matrix that is three-dimensional. In yet other embodiments, a matrix can be composed of substantially a single multimer (i.e., a single shape). Further embodiments can be directed to a matrix composed of a single shaped multimer and linear nucleic acids. In yet further embodiments, a matrix is composed of two or more different shaped multimers, and/or in preselected ratios of one multimer to another.

One aspect of the invention is directed to a polymeric matrix comprised of branched nucleic acid molecules wherein said nucleic acid molecules form the backbone or are building blocks utilized to form a matrix. The matrix can be three-dimensional thus providing a scaffold of nucleic acid molecules. In one embodiment, the tensile strength for the scaffold (i.e., matrix) is about 30, 35, 40, 45, 50 and 55%. In another embodiment, the matrix forms a gel capable of swelling 2, 3, 4, 5, 6, 7, 8, 9, 10, or 20 fold as compared to a dried form of the matrix. In another embodiment, the matrix forms a hydrogel. In yet another embodiment, the matrix forms protein-yielding gel, or "P-gel".

In various aspects of the invention, the matrix is comprised of branched, or branched and linear nucleic acid molecules, where the branched nucleic acid molecules are selected from X-, Y-, T-, dumbbell-, dendrimer-shape or any combination thereof. In one embodiment, the matrix is comprised entirely of branched nucleic acids that are X-, Y-, T-, dumbbell- or dendrimer-shape nucleic acids. In additional embodiments, the multimers comprised in a matrix are entirely DNA, DNA and RNA, or entirely RNA. In further embodiment, the multimers can be TNA, PNA and LPNA, including a combination of any such nucleic acids, as well analogs thereof.

In one embodiment, a matrix of the invention is comprised of X-DNA that is cross-linked to linear DNA. In another embodiment, DNAs form a protein expressing gel ("P-gel"). In yet a further embodiment, the X-DNA is cross-linked to linear RNA, wherein the RNA encodes a protein of interest. Another embodiment is directed to a P-gel expressing one or more proteins in a cell-free environment, where the protein-encoding nucleic acid sequences are either RNA or DNA, or a combination thereof.

In one aspect, a matrix is formed to contain and to deliver a bioactive (also "biologically active") agent. In some embodiments, such a matrix comprises one or more bioactive agents, which are different. In one embodiment, a matrix comprises a bioactive agent comprising a therapeutic agent. In another embodiment, a matrix comprises a bioactive agent comprising a cell.

In some embodiments, one or more matrixes comprised of one or more different shaped nucleic acid building blocks are utilized to deliver an effective amount of a bioactive agent to a cell, either in vitro or in vivo. In some embodiments, such matrices/gels are implanted into a target tissue site in an animal.

In yet another embodiment, a matrix comprises a therapeutic agent and a cell. In further embodiments, the matrix comprises one or more different cells. In a preferred embodiment, a matrix comprises mammalian cells. In other embodiments, a matrix or matrixes are utilized to encapsulate one or more bioactive agents, which bioactive agents include cells. In one embodiment, the cells are mammalian cells.

In one embodiment, a nucleic acid based matrix is linked to an additional copolymer or copolymers. In a further embodiment, a matrix is linked to molecules, elements or compounds that further strengthen the matrix structure, or provide a desired characteristic. In one embodiment, a matrix is composed of multimers that are linked to metal particles, such as gold particles (FIG. 11).

In other embodiments, the multimers selected to compose a matrix are preselected to form a matrix having pores. The multimers can be selected based on shape and size, and length of sequence. In some embodiments, the pores are of sizes that are selected to deliver a desired bioactive agent, or deliver one or more desired bioactive agents.

In additional embodiments, DL-NAMs are utilized to form dendrimer structures that can be monodisperse and multivalent. In such embodiments, a dendrimer can be composed of a single shaped multimer or two or more different shaped multimers. Dendrimers provide a multivalent and/or monodisperse structure that provides multiple sites for addition of one or more molecules of interest, including bioactive agents, selection markers, antibiotics, detection signals/labels, drugs or a combination thereof. In various embodiments, such vectors can be utilized to deliver one or more bioactive agents to a cell or animal.

In yet another aspect, the nucleic acid structures form a matrix that provides a cell-free protein synthesis system. In some embodiments, such systems can comprise macromolecules that are necessary for protein modification (e.g., post-translational modification, glycosylation, etc.). In yet other embodiments, the nucleic acids comprised in such matrices can comprise RNA. Thus, protein-synthesizing matrices of the invention can comprise macromolecules necessary for transcription, translation and/or protein modification. Obtaining such macromolecules and their use in cell-free protein synthesis is described herein.

BRIEF DESCRIPTION OF THE FIGURES

The illustrations included within this specification describe many of the advantages and features of the invention. It shall be understood that similar reference numerals and characters noted within the illustrations herein may designate the same or like features of the invention. The illustrations and features depicted herein are not necessarily drawn to scale.

FIG. 2: (A) Microscopic images for the array of protein producing DNA hydrogel pads on the glass substrate. The size of each one pad is 200 μm×400 μm×20 μm. After peeled off from PDMS mold, the gel remained on the glass substrate. (B) Also, the gels were stained with SYBR I which is very sensitive to dsDNA. (C) AFM image showed the internal structure of the hydrogel in swollen state. (D) DNA building blocks including X-shaped DNA: Lane 1 corresponds to the 50 bps step ladder. Lanes 2, 3, and 4 correspond to the incomplete X-DNA and lane 5 corresponds to the complete X-DNA. (E) a luciferase gene after Mlu I restriction enzyme digestion: Lane 1 corresponds to the 1.0 kbps step ladder. Lanes 2 and 3 correspond to the plasmid DNA including a luciferase gene and a luciferase gene after Mlu I digestion, respectively.

FIG. 5. External morphologies and internal structures of different DNA hydrogels. A, B, C: FE-SEM images of dried X-, Y-, and T-DNA DNA hydrogels, respectively. D, E, F: Confocal microscopic images of the swollen X-, Y-, and T-DNA hydrogels, respectively. G: AFM image of the X-DNA gel.

DETAILED DESCRIPTION OF THE INVENTION

Figures 1A, 1B, 1C, 1D:
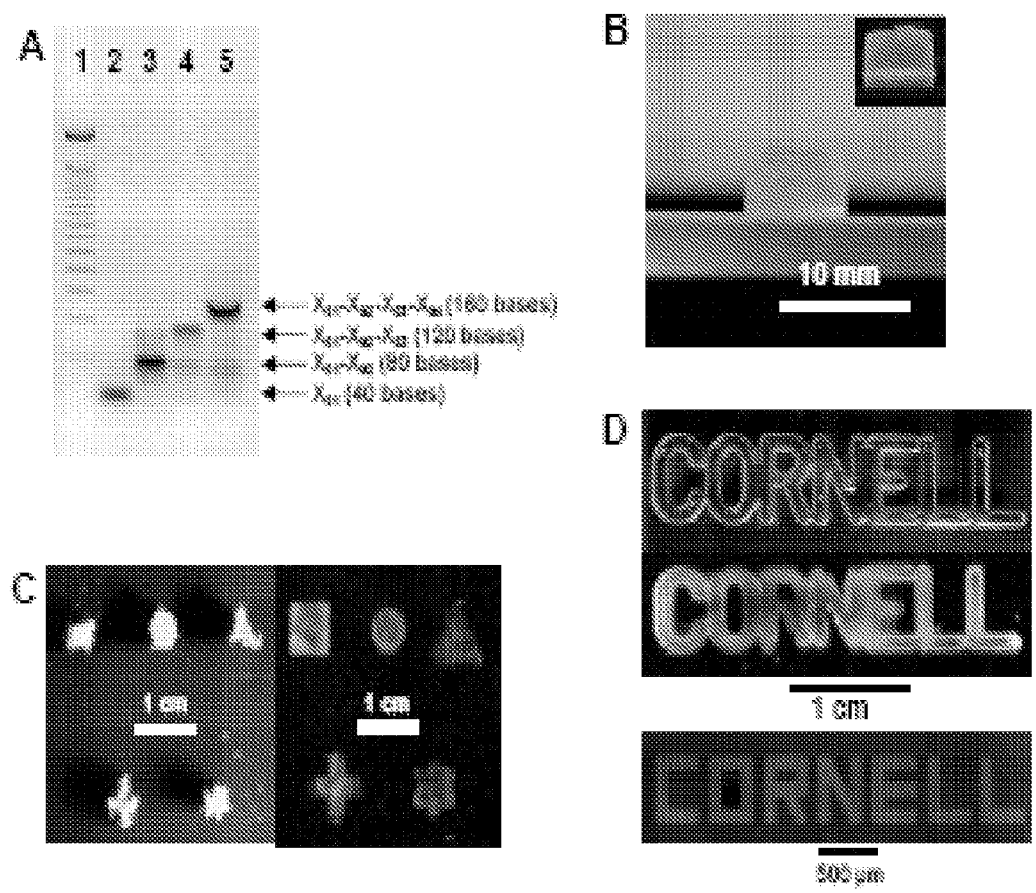
FIG. 1: (A) shows the gel electrophoretic migration of DNA building blocks. Lane 1 corresponds to a 50-bp step ladder marker. Lanes 2 and 3 correspond to X01 oligonucleotide with 40 bases and X01-X02 oligonucleotide dimers with 80 bases (18 base pairs plus 44 bases), respectively. Lanes 4 and 5 correspond to X01-X02-X03 trimer with 120 bases (36 bases pairs plus 48 bases) and X01-X02-X03-X04 tetramer (i.e. X-DNA) with 160 bases (72 base pairs plus 16 bases). (B): A swollen X-DNA hydrogel fabricated in a cylindrical mold. The size is 7.0 mm in diameter and 3.0 mm in height. The inset shows the DNA gel stained with SYBR I. (C): Images of the dried (left) and swollen (right) X-shape DNA hydrogel with different patterns: rectangular, circular, triangular, star and cross (from the top left corner, clockwise). (D): X-shape DNA gels patterned in CORNELL shapes at centimeter (macroscopic) scale (top and middle rows) and micrometer scale (bottom row). The gels were stained with two different, DNA-specific fluorescent dyes: EtBr (red, the middle row) and SYBR I (green, the bottom row).

While the invention has been described with reference to the aforementioned specification, the descriptions and illustrations of the preferable embodiments herein are not meant to be construed in a limiting sense. It shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art upon reference to the present disclosure. It is therefore contemplated that the appended claims shall also cover any such modifications, variations and equivalents.

Fabrication of DNA building blocks and DNA hydrogels.

The practice of various embodiments of the invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the terms "biologically active agent" or "bioactive agent" are used interchangeably and include but are not limited to a biological or chemical compound such as a simple or complex organic or inorganic molecule, peptide, peptide mimetic, protein (e.g. antibody, angiogenic, anti-angiogenic and cellular growth factors), an antigen or immunogen, liposome, small interfering RNA, or a polynucleotide (e.g. vector, virus, viral vector, or anti-sense), therapeutic agents, organic or inorganic molecules can include a homogenous or heterogeneous mixture of compounds, including pharmaceuticals, radioisotopes, crude or purified plant extracts, and/or a cell, entities that alter, inhibit, activate, or otherwise affect biological or biochemical events, including classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, etc.) that are commonly found in cells and tissues, whether the molecules themselves are naturally-occurring or artificially created (e.g., by synthetic or recombinant methods). Such agents may be naturally derived or synthetic.

Examples of such agents include but are not limited to drugs, for example, anti-cancer substances, analgesics, opioids, anti-AIDS substances, anti-cancer substances, immunosuppressants (e.g., cyclosporine), anti-viral agents, enzyme inhibitors, neurotoxins, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the DA under 21 C.F.R. §§500 through 589, incorporated herein by reference are all considered acceptable for use in accordance with compostions and methods disclosed herein.

The term "scaffold" can mean a three-dimensional structure capable of supporting cells. Cells may be encapsulated by the scaffold or may be disposed in a layer on a surface of the scaffold. The scaffold is formed by but not limited to the self-assembly of nucleic acid molecules described herein, that may include X-, Y-, T-, dumbell-, or dendrimer-shape, as well as linear or circular shapes, or a combination thereof. It is also contemplated that the nucleic acid may be linked to a compound, such as a chemoattractant or a therapeutically active compound. The peptide scaffold may be formed from one or more distinct molecular species of nucleic acids which are complementary and structurally compatible with each other. Nucleic acids containing mismatched pairs, may also form scaffolds if the disruptive force is dominated by stabilizing interactions between the peptides. Scaffolds are also referred to herein as matrixes, matrices, gels, nucleic acid hydrogel structures, nucleic acid gel structures, or hydrogel structures.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA (A, B and Z structures) of any sequence, PNA, LNA, TNA (treose nucleic acid), isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components.

A polynucleotide may be further modified after polymerization, such as by conjugation with a labeling component. The nucleic acids, used in the various embodiments disclosed herein, may be modified in a variety of ways, including by crosslinking, intra-chain modifications such as methylation and capping, and by copolymerization. Additionally, other beneficial molecules may be attached to the nucleic acid chains. The nucleic acids may have naturally occurring sequences or artificial sequences. The sequence of the nucleic acid may be irrelevant for many aspects disclosed herein. However, special sequences may be used to prevent any significant effects due to the information coding properties of nucleic acids, to elicit particular cellular responses or to govern the physical structure of the molecule. A "nucleotide probe" or "probe" refers to a polynucleotide used for detecting or identifying its corresponding target polynucleotide in a hybridization reaction. The nucleic acids may comprise intron and exon sequences, modified sequences, RNA, DNA, or analogs thereof.

As used herein, the term "nanofiber" refers to a fiber having a diameter of nanoscale dimensions. Typically a nanoscale fiber has a diameter of 500 nm or less. According to certain embodiments of the invention a nanofiber has a diameter of less than 100 nm. According to certain other embodiments of the invention a nanofiber has a diameter of less than 50 nm. According to certain other embodiments of the invention a nanofiber has a diameter of less than 20 nm. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm.

As used herein, the terms "isolated and/or purified" refer to in vitro preparation, isolation and/or purification of a nucleic acid molecule of the invention, so that it is not associated with in vivo substances, or is substantially purified from in vitro substances.

The following terms are used to describe the sequence relationships between two or more polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a segment of or the entirety of a specified sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 5, 10, or 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty can be introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988), which is hereby incorporated by reference in its entirety; the local homology algorithm of Smith et al, *Adv. Appl. Math.*, 2:482 (1981), which is hereby incorporated by reference in its entirety; the homology alignment algorithm of Needleman and Wunsch, *JMB*, 48:443 (1970), which is hereby incorporated by reference in its entirety; the search-for-similarity-method of Pearson and Lipman, *Proc. Natl. Acad. Sci. USA*, 85:2444 (1988), which is hereby incorporated by reference in its entirety; the algorithm of Karlin and Altschul, *Proc. Natl. Acad. Sci. USA*, 87:2264 (1990), which is hereby incorporated by reference in its entirety; modified as in Karhn and Altschul, *Proc. Natl. Acad. Sci. USA*, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988), Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994), which are hereby incorporated by reference in their entirety. The ALIGN program is based on the algorithm of Myers and Miller, supra. The BLAST programs of Altschul et al., *JMB*, 215:403 (1990); *Nucl. Acids Res.*, 25:3389 (1990), which are hereby incorporated by reference in their entirety, are based on the algorithm of Karlin and Altschul supra.

Software for performing BLAST analyses is publicly available through the National Center for Biotechnology Information (worldwideweb.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997), which is hereby incorporated by reference in its entirety. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix. See worldwideweb.ncbi.nlm.nih.gov. Alignment may also be performed manually by inspection.

Comparison of nucleotide sequences for determination of percent sequence identity to the sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As is known to one skilled in the art, hybridization can be performed under conditions of various stringency. Suitable hybridization conditions are such that the recognition interaction between the probe and target ER-stress related gene is both sufficiently specific and sufficiently stable. Conditions that increase the stringency of a hybridization reaction are widely known and published in the art. See, for example, (Sambrook, et al., (1989), supra; Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution.

For DNA-DNA hybrids, the $T_m$ can be approximated from the equation of Meinkoth and Wahl, *Anal. Biochem.,* 138:267 (1984), which is hereby incorporated by reference in its entirety; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH.

However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes,* Part I Chapter 2 "Overview of Principles of Hybridization and the Strategy of Nucleic Acid Probe Assays," Elsevier, New York (1993), which is hereby incorporated by reference in its entirety. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g. more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product".

As used herein the term "ligation" refers to the process of joining DNA molecules together with covalent bonds. For example, DNA ligation involves creating a phosphodiester bond between the 3' hydroxyl of one nucleotide and the 5' phosphate of another. Ligation is preferably carried out at 4-37° C. in presence of a ligase enzyme. Suitable ligases include *Thermus thermophilus* ligase, *Thermus acquaticus* ligase, *E. coli* ligase, T4 ligase, and *Pyrococcus* ligase.

A number of techniques for protein analysis are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

In various embodiments of the invention, the nucleic acid-based matrixes can have nanoparticle, nanosphere, nanoshell, micelle, core-shell, multi-core shell, multi-layered, nanogel, microparticle, microsphere, microgel, macrogel, nanoscale, macroscale, macroscopic, block, branched, hyperbranched, hybrid, tree-like, comb-like, brush, grafting, vesicle, coil, global, coil-coil, coil-global, rod, membrane, film, coating, self-assembly, cyclic, microconduit, microchannel, nanochannel, porous, nonporous, tube, microtube, nanotube, semi-interpenetrating network, cross-linked, or a highly networked structure.

Nucleic Acid Molecules of the Invention

In certain aspects, the nucleic acid molecules provide monomer building blocks and/or cross-linkers that form a three-dimensional matrix or scaffold structure. A matrix of the invention can be comprised of nucleic acids that are X-shaped, Y-shaped, T-shaped, dumbbell-shaped (e.g., FIGS. 8-10, FIGS. 12-16 or FIGS. 21-30) nucleic acids, or a combination thereof. Collectively or singularly, one or more matrices of the present invention may be referred to herein as "biomaterial", "matrix", "dendrimer", "dendrimer like", hydrogel, gel or "scaffold", and including plural forms thereof. Examples of various shape nucleic acids (e.g., DNA) are disclosed in U.S. patent application Ser. Nos. 10/877,697 and 60/756,453, which are incorporated by reference in their entirety.

Furthermore, in some embodiments the matrixes form gels that are molded into any desired shape and/or size (FIG. 1). In one embodiment, such gels are formed entirely from branched DNA. In other embodiments, the gels are formed of linear and branched nucleic acids. In yet further embodiments, the linear or branched nucleic acids can be DNA, RNA, PNA, TNA, LNA or any combination thereof. For example, a gel can comprise branched DNA that form building blocks supporting the matrix and also linking linear DNA that encodes a protein(s) of interest. In another embodiment, the hydrogel can be comprised entirely of RNA building blocks and protein-encoding sequences. In yet another embodiment, the gels are hydrogels. Such hydrogels are in large part comprised of $H_2O$ molecules (i.e., in the hydrated state; e.g., FIG. 1D), thus are extremely inexpensive, (e.g., an average hydrogel costs less than $5). In addition, fine tuning of the chemical and physical properties of these hydrogels can be easily accomplished by adjusting the concentrations and types of branched nucleic acid building blocks, thus allowing the hydrogels to comprise particular physical/chemical properties tailored for specific applications.

Nucleic acids have different rates of degradation, which may be modified and exploited. Additionally, particular degradation products may be desired (for instance, nucleic acids with a given sequence). The sites or timing of degradation may be modified so as to obtain these products. The type of nucleic acid selected may affect degradation as well as the different combination of types of nucleic acid. RNA will likely degrade much more rapidly than DNA. Different DNA structures may have different degradation rates. This may also vary by the tissue in which the nucleic acid is used. Various disease states or injuries may also affect degradation. In some embodiments, the degradation rate can be controlled by selecting nucleic acids of a single shape, or a combination of different shapes (i.e., X, Y, T, dumbbell shapesa).

In other embodiments, purified nucleic acids may be linked to other nucleic acids or other compounds to reduce degradation. Linking may be accomplished in a variety of ways, including hydrogen bonds, ionic and covalent bonds, $\pi$-$\pi$ bonds, polarization bonding, van der Wals forces. As used herein, "link" and "cross-link" are used interchangeably. More than one type of crosslinking may be used within a given biomaterial. For example, use of a type of crosslinking easily degraded in a cell coupled with a more degradation resistant type of crosslinking may result in a biomaterial that is opened in two phases, one when the easily degraded crosslinks are broken and second when the more resistant crosslinks or the nucleic acid itself are degraded. Crosslinking may be accomplished by UV radiation, esterification, hydrolysis, intercalating agents, neoplastic agents, formaldehyde, formalin, or silica compounds. Examples of linking include but are not limited to the use of siloxane bridges as described in U.S. Pat. No. 5,214,134.

Crosslinking may occur between two strands of a double stranded nucleic acid or between the strands of two separate double strands. It may also occur between two separate single strands. Double strand to single strand crosslinking is also possible, as is crosslinking between different regions of one strand. Increased levels of crosslinking will generally slow degradation of nucleic acids. Linkers such as small organic molecules (esters, amines) or inorganic molecules (silicas, siloxanes), including microparticles or nanoparticles thereof, may be used to attach copolymers to nucleic acids. Any of the different shaped nucleic acids of the invention can be linked or cross-linked by one or methods described herein. Therefore, X-shaped, Y-shaped, T-shaped, dumbbell shaped or any combination thereof can be linked to each other, as well as to other chemical moieties or polymeric compounds.

In addition, in certain aspects, the nucleic acids can be linked to biologically active agents, including drugs, selection markers, detectable signals, other therapeutic agents, peptides, such as signal or cell targeting peptides, nucleic acid sequences, proteins (including antibodies), plasmids, viruses, viral vectors, small molecules, inorganic compounds, metals or derivatives thereof. Additionally, any inorganic or organic molecules, including amino acids, silicas, cytokines, such as interleukins, biologics and drugs may be added to the nucleic acid polymers to produce certain biological effects. Nucleic acids provide a variety of molecular attachment sites and therefore facilitate covalent, ionic and hydrogen bonding, as well as Van der Wals attachments, or other forms of attachment.

In one embodiment, a nucleic acid-based matrix is strengthened by cross-linking nanoparticles onto the nucleic acids of the matrix. In one embodiment, the nucleic acids are branched DNA molecules. In one preferred embodiment, the nanoparticles are gold, silver or copper.

In addition, the nucleic acids may be methylated, ethylated, alkylated, or otherwise modified along the backbone to influence degradation rates. Generally, methylated, hemi-methylated, ethylated, or alkylated nucleic acids will degrade more slowly. Other backbone modifications affecting degradation rates include the use of heteroatomic oligonucleoside linkages as described in U.S. Pat. No. 5,677,437. Additionally, alkyl modifications may be used to prevent the nucleic acid from being transcribed or translated in a given tissue or organism. In addition, the nucleic acids may be capped to prevent degradation. Such caps are generally located at or near the termini of the nucleic acid chains. Examples of capping procedures are included in U.S. Pat. Nos. 5,245,022 and 5,567,810.

In certain embodiments, where the nucleic acids are DNA molecules, the quantity of DNA in a matrix can be measured by used DNA specific labels. DNA-binding dye suitable for this application include SYBR green, SYBR blue, DAPI, propidium iodine, Hoechste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015

In further aspects of the invention, matrixes also include copolymers that maybe biodegradable or nonbiodegradable. Copolymers that are also biodegradable and non-toxic to mammals may be preferred. However, polymers in which only one polymer (e.g. the nucleic acid portion) degrades, leaving a non-biodegradable framework may also be desirable in certain situations. Examples of materials that may be used as copolymers include but are not limited to, poly(amino acids), including PGA, PLA, PLGA and poly(proline), polysaccharides, such as cellulose, chitin and dextran, proteins, such as fibrin and casein, VICRYL™, MAXON™, PDS, poly(e-caprolactone), polyanhydrides, trimethylene carbonate, poly(.beta.-hydroxybutyrate), poly(DTH imino carbonate), poly(bisphenol A iminocarbonate), poly(ortho ester), polycyanoacrylate, polyphospohazene, poly(N-isopropylacrylamide), poly(N-alkylacrylamide), poly(N-n-propylacrylamide), poly(N-isopropylmethacrylamide), poly(ethylene oxide)-poly(propylene oxide)-poly(ethylene oxide), poly(DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly(epsilon-caprolactone), polyanhydride, poly(bis(p-carboxyphenoxy) propane-sebacic acid), polyorthoester, polyphosphoester, polyphosphazene, polystyrene, polyurethane, poly(amino acid), and hyaluronic acid, derivatives thereof, aliphatic polyesters, poly(amino acids), copoly(ether-esters), polyalkylene oxalates, polyamides, poly(iminocarbonates), polyorthoesters, polyoxaesters, polyamidoesters, polyoxaesters containing amine groups, poly(anhydrides), polyphosphazenes, polyoxaamides and polyoxaesters containing amines and/or amido groups, polyanhydrides from diacids of the form HOOC—$C_6H_4$—O—$(CH_2)_m$—O—$C_6H_4$—COOH where m is an integer in the range of 2 to 8 and copolymers thereof with aliphatic alpha-omega diacids of up to 12 carbons are also suitable, and blends of any thereof.

Aliphatic polyesters include but are not limited to homopolymers and copolymers of lactide (which includes lactic acid, d-, l- and meso lactide), glycolide (including glycolic acid), □-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, □-decalactone, hydroxybutyrate (repeating units), hydroxyvalerate (repeating units), 1,4-dioxepan-2-one (including its dimer 1,5,8,12-tetraoxacyclotetradecan 7,14-dione), 1,5-dioxepan-2-one, 6,6-dimethyl-1,4-dioxan-2-one 2,5-diketomorpholine, pivalolactone, alpha, alpha diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one or any polymer material capable of linking to nucleic acids of the present invention.

Additional examples of copolymers that can be linked to the nucleic acid matrixes of the present invention include peptide sequences. Therefore, in some embodiments the nucleic acid and a copolymer such as peptide sequences are utilized to form a nucleic acid-peptide matrix. Examples of such peptides include but are not limited to sequences such as those reported in U.S. Pat. Nos. 5,670,483 and 5,955,343, and U.S. patent application Ser. No. 09/778,200, the contents of all of which are incorporated herein by reference. These peptide chains consist of alternating hydrophilic and hydrophobic amino acids that are capable of self-assembling to form an exceedingly stable beta-sheet macroscopic structure in the presence of electrolytes, such as monovalent cations.

The peptide chains are complementary and structurally compatible. The side-chains of the peptide chains in the structure partition into two faces, a polar face with charged ionic side chains and a nonpolar face with alanines or other hydrophobic groups. These ionic side chains are self-complementary to one another in that the positively charged and negatively charged amino acid residues can form complementary ionic pairs. These peptide chains are therefore called ionic, self-complementary peptides, or Type I self-assembling peptides. If the ionic residues alternate with one positively and one negatively charged residue (−+−+−+−+), the peptide chains are described as "modulus I;" if the ionic residues alternate with two positively and two negatively charged residues (−−++−−++), the peptide chains are described as "modulus II." In some embodiments, peptide sequences for use with the invention have at least 12 or 16 amino acid residues. Both D- and L-amino acids may be used to produce peptide chains. They may be mixed in the same chain, or peptide compositions may be prepared having mixtures of individual chains that themselves only include D- and L-amino acids. Exemplary peptide sequences for use with the invention include those listed in Table 1. Therefore, in various embodiments a nucleic acid matrix or gel can further comprise one or more peptides disclosed herein to form, for example, a DNA-peptide matrix. Such peptides can be associated with X-, Y-, T-, dumbell- or dendrimer-shape nucleic acids to provide an additional level of control for providing matrixes of morphological and internal structures as desired.

TABLE 1

Representative Self-Assembling Peptides

| Name | Sequence (n-->c) | Modulus | SEQ. ID NO. |
|---|---|---|---|
| DAR16-IV* | n-DADADADARARARARA-c | IV | 1 |
| DAR32-IV | n-(ADADADADARARARAR)$_2$-c | IV | 2 |
| EHK16 | n-HEHEHKHKHEHEHKHK-c | N/A | 3 |
| EHK8-I | n-HEHEHKHK-c | N/A | 4 |
| VE20* | n-VEVEVEVEVEVEVEVEVE-c | N/A | 5 |
| RF20* | n-RFRFRFRFRFRFRFRFRFRF-c | N/A | 6 |

N/A denotes not applicable
*These peptides form a β-sheet when incubated in a solution containing NaCl, however they have not been observed to self-assemble to form a macroscopic scaffolds.

Other self-assembling peptide chains may be generated by changing the amino acid sequence of any self-assembling peptide chains by a single amino acid residue or by multiple amino acid residues. Additionally, the incorporation of specific cell recognition ligands, such as RGD or RAD, into the peptide scaffold may promote the proliferation of the encapsulated cells. In vivo, these ligands may also attract cells from outside a scaffold to the scaffold, where they may invade the scaffold or otherwise interact with the encapsulated cells. To increase the mechanical strength of the resulting scaffolds, cysteines may be incorporated into the peptide chains to allow the formation of disulfide bonds, or residues with aromatic rings may be incorporated and cross-linked by exposure to UV light. The in vivo half-life of the scaffolds may also be modulated by the incorporation of protease cleavage sites into the scaffold, allowing the scaffold to be enzymatically degraded. Combinations of any of the above alterations may also be made to the same peptide scaffold.

Self-assembled nanoscale structures can be formed with varying degrees of stiffness or elasticity. While not wishing to be bound by any theory, low elasticity may be an important factor in allowing cells to migrate into the scaffold and to communicate with one another once resident in the scaffold. The peptide scaffolds described herein typically have a low elastic modulus, in the range of 1-10 kPa as measured in a standard cone-plate rheometer. Such low values permit scaffold deformation as a result of cell contraction, and this deformation may provide the means for cell-cell communication. In addition, such moduli allow the scaffold to transmit physiological stresses to cells migrating therein, stimulating the cells to produce tissue that is closer in microstructure to native tissue than scar. Scaffold stiffness can be controlled by a variety of means including changes in peptide sequence, changes in peptide concentration, and changes in peptide length. Other methods for increasing stiffness can also be used, such as by attaching a biotin molecule to the amino- or carboxy-terminus of the peptide chains or between the amino- and carboxy-termini, which may then be cross-linked.

Peptide chains capable of being cross-linked may be synthesized using standard f-moc chemistry and purified using high pressure liquid chromatography (Table 11). The formation of a peptide scaffold may be initiated by the addition of electrolytes as described herein. The hydrophobic residues with aromatic side chains may be cross-linked by exposure to UV irradiation. The extent of the cross-linking may be precisely controlled by the predetermined length of exposure to UV light and the predetermined peptide chain concentration. The extent of cross-linking may be determined by light scattering, gel filtration, or scanning electron microscopy using standard methods. Furthermore, the extent of cross-linking may also be examined by HPLC or mass spectrometry analysis of the scaffold after digestion with a protease, such as matrix metalloproteases. The material strength of the scaffold may be determined before and after cross-linking.

TABLE 2

Representative Self-Assembling Peptides

| Name | Sequence (n-->c) | Modulus | SEQ. ID. NO. |
|---|---|---|---|
| RAD16-I | n-RADARADARADARADA-c | I | 7 |
| RGDA16-I | n-RADARGDARADARGDA-c | I | 8 |
| RADA8-I | n-RADARADA-c | I | 9 |
| RAD16-II | n-RARADADARARADADA-c | II | 10 |
| RAD8-II | n-RARADADA-c | II | 11 |
| EAKA16-I | n-AEAKAEAKAEAKAEAK-c | I | 12 |
| EAKA8-I | n-AEAKAEAK-c | I | 13 |
| RAEA16-I | n-RAEARAEARAEARAEA-c | I | 14 |
| RAEA8-I | n-RAEARAEA-c | I | 15 |
| KADA16-I | n-KADAKADAKADAKADA-c | I | 16 |
| KADA8-I | n-KADAKADA-c | I | 17 |
| KLD12 | n-KLDLKLDLKLDL-c | | 18 |
| EAH16-II | n-AEAEAHAHAEAEAHAH-c | II | 19 |
| EAH8-II | n-AEAEAHAH-c | II | 20 |
| EFK16-II | n-FEFEFKFKFEFEFKFK-c | II | 21 |
| EFK8-II | n-FEFKFEFK-c | I | 22 |
| KFE12 | n-FKFEFKFEFKFE-c | | 23 |
| KFE8 | n-FKFEFKFE-c | | 24 |
| KFE16 | n-FKFEFKFEFKFEFKFE-c | | 25 |
| KFQ12 | n-FKFQFKFQFKFQ-c | | 26 |
| KIE12 | n-IKIEIKIEIKIE-c | | 27 |
| KVE12 | n-VKVEVKVEVKVE | | 28 |
| ELK16-II | n-LELELKLKLELELKLK-c | II | 29 |
| ELK8-II | n-LELELKLK-c | II | 30 |

TABLE 2-continued

Representative Self-Assembling Peptides

| Name | Sequence (n-->c) | Modulus | SEQ. ID. NO. |
|---|---|---|---|
| EAK16-II | n-AEAEAKAKAEAEAKAK-c | II | 31 |
| EAK12 | n-AEAEAEAEAKAK-c | IV/II | 32 |
| EAK8-II | n-AEAEAKAK-c | II | 33 |
| KAE16-IV | n-KAKAKAKAEAEAEAEA-c | IV | 34 |
| EAK16-IV | n-AEAEAEAEAKAKAKAK-c | IV | 35 |
| RAD16-IV | n-RARARARADADADADA-c | IV | 36 |
| DAR16-IV | n-ADADADADARARARAR-c | IV | 37 |

Aggrecan processing sites, such as those underlined in Table 12, may optionally be added to the amino- or carboxy-terminus of the peptides or between the amino- and carboxy-termini. Likewise, other matrix metalloprotease (MMP) cleavage sites, such as those for collagenases, may be introduced in the same manner. Peptide scaffolds formed from these peptide chains, alone or in combination with peptides capable of being cross-linked, may be exposed to various proteases for various lengths of time and at various protease and peptide concentrations. The rate of degradation of the scaffolds may be determined by HPLC, mass spectrometry, or NMR analysis of the digested peptide chains released into the supernatant at various time points. Alternatively, if radiolabeled peptide chains are used for scaffold formation, the amount of radiolabeled material released into the supernatant may be measured by scintillation counting. For some embodiments, the beta-sheet structure of the assembled peptide chains is degraded sufficiently rapidly that it is not necessary to incorporate cleavage sites in the peptide chains.

TABLE 3

Representative Peptide Sequences Having Aggrecan Processing Sites

| Name | Sequence (N-->C) | SEQ. ID. NO. |
|---|---|---|
| REE | RGDYRYDYTFREEE-GLGSRYDYRGDY | 38 |
| KEE | RGDYRYDYTFKEEE-GLGSRYDYDGDY | 39 |
| SELL | RGDYRYDYTASELE-GRGTRYDYRGDY | 40 |
| TAQE | RGDYRYDYAPTAQE-AGEGPRYDY-RGDY | 41 |
| ISQE | RGDYRYDYPTISQE-LGQRPRYDYRGDY | 42 |
| VSQE | RGDYRYDYPTVSQE-LGQRPRYDYRGDY | 43 |

If desired, peptide scaffolds may also be formed with a predetermined shape or volume. To form a scaffold with a desired geometry or dimension, an aqueous peptide solution is added to a pre-shaped casting mold, and the peptide chains are induced to self-assemble into a scaffold by the addition of an electrolyte, as described herein. The resulting geometry and dimensions of the macroscopic peptide scaffold are governed by the concentration and amount of peptide solution that is applied, the concentration of electrolyte used to induce assembly of the scaffold, and the dimensions of the casting apparatus.

If desired, peptide scaffolds may be characterized using various biophysical and optical instrumentation, such as circular dichroism (CD), dynamic light scattering, Fourier transform infrared (FTIR), atomic force microscopy (ATM), scanning electron microscopy (SEM), and transmission electron microscopy (TEM). For example, biophysical methods may be used to determine the degree of beta-sheet secondary structure in the peptide scaffold. Additionally, filament and pore size, fiber diameter, length, elasticity, and volume fraction may be determined using quantitative image analysis of scanning and transmission electron microscopy. The scaffolds may also be examined using several standard mechanical testing techniques to measure the extent of swelling, the effect of pH and electrolyte concentration on scaffold formation, the level of hydration under various conditions, and the tensile strength.

The type of nucleic acid polymer or copolymer used will affect the resulting chemical and physical structure of the polymeric biomaterial. The matrixes formed by nucleic acid polymers alone, or nucleic acid polymers and copolymers may be used for a variety of purposes, including controlled release of biologically active agents described herein (e.g., drug delivery), encapsulation and/or culturing cells, tissue engineering applications including, inter alia, to increase tissue tensile strength, as templates for tissue formation, to guide tissue formation, to stimulate nerve growth, to improve vascularization in tissues, as a biodegradable adhesive, as device or implant coating, or to improve the function of a tissue or body part. In addition, the matrixes formed from nucleic acid polymers alone, or nucleic acid polymers and copolymers can be utilized in a cell-free protein producing system.

Therefore, in one aspect, a matrix is comprised of branched building block nucleic acid molecules linked to at least one copolymer known in the art or disclosed herein above, and said matrix comprises linear nucleic acid molecules that encode one or more proteins of interest to be expressed therein or therefrom.

Matrixes comprising nucleic acids and copolymers may be formed in a variety of ways, depending upon the copolymer used and the desired properties of the finished matrix(es). The copolymer may be attached to the nucleic acid by covalent, ionic or hydrogen bonds or by Van der Wals forces. Linkers such as small organic molecules (esters, amines) or inorganic molecules (silicas, siloxanes), including microparticles or nanoparticles thereof, may be used to attach copolymers to nucleic acids. The finished biomaterial may contain the nucleic acids and copolymers arranged in a variety of fashions including, substantially end-to-end, end-to-side, side-to-side, or any mixture thereof with one or more linkages securing such attachments. Copolymers may also fall into the general forms or block copolymers and graft copolymers. Furthermore, chemical and biological properties of nucleic acid polymers may be influenced by modifications of the copolymers, such as modification of the hydrophobicity or hydrophilicity of the polymers or copolymers.

Nucleic acid-based matrixes provide many important advantages over protein hydrogels and polymeric hydrogels. First, many different nucleic acid hydrogels with unique properties can be precisely designed and easily fabricated because of the availability of a great variety of branched nucleic acid building blocks of different shapes and different lengths. For example, different shapes and/or different lengths of nucleic acid monomers can result in different pore sizes of the matrix formed therewith, which in turn can control drug release rates, or provide different three-dimensional scaffolds for cell culturing or tissue engineering. Furthermore, matrixes comprised of nucleic acids of different shapes/lengths can also provide scaffolds for improved protein production, by providing anchoring points for macromolecules necessary for protein expression (e.g., polymerases), as well as a plurality of coding sequences for one or more proteins.

Therefore, in various embodiments, different release rates are readily obtained by selection Y-, T-, X-DNA or a combination of one or more Y-, T-, or X-DNA to compose a hydrogel.

Second, since the conditions for fabricating nucleic acid matrixes are very mild (e.g. at room temperature and with a neutral pH), in various embodiments the matrixes provide a unique tool that may be applied in many biotechnological or biomedical applications. For example, since many bioactive agents, including drugs and/or proteins, or cells (e.g., mammalian cells) can be dissolved or dispersed in an aqueous nucleic acid solution, encapsulation of such biosactive agents, e.g., drugs and live cells, is effected in situ, eliminating the need to load drugs into gels and also avoiding denaturing conditions that preclude, for example, encapsualtion of live cells.

Consequently, bioactive agents and cells are contained in an aqueous, physiologically compatible environment, during the pre-gelling, thus allowing the efficiency of encapsulation of such agents to reach close to 100%. In addition, nucleic acid building blocks can also post-react with other chemicals such as nucleic acid-specific reagents, e.g., fluorescent dyes, enabling the tracing of gel matrixes, of biodegradation and distribution processes.

Furthermore, nucleic acid matrixes are biodegradable and non-immunogenetic (e.g., DNA strands are synthesized de novo and totally lack the immuno-stimulative, bacterial CpG motifs (Krieg et al., *Nature* 374, 546 (1995); D. Schwartz et al, *J Clin Invest* 100, 68 (1997))), ideal as controlled drug delivery carriers. Therefore, providing yet additional improvement over many of the existing platforms for biomaterials. Moreover, as alluded to previously, due to the mild gelling conditions, in situ encapsulation, and their intrinsic biocompatibilities and biodegradabilities, nucleic acid hydrogels can also encapsulate live cells, thus serve as matrices for 3D cell culture or tissue engineering. In addition, such matrixes can also serve as carriers in cell/tissue transplantation, whereby a bioactive agent and/or cell is delivered in effective concentrations to a desired target site in vivo.

Building Blocks of Different Shapes

One aspect of the invention is directed to a matrix comprising nucleic acids that include X-shape, T-shape, Y-shape, dumbbell-shape or dendrimer shape, which nucleic acids can be used as building blocks for new, designer biomaterials. Thus the nucleic acid(s) have different shapes and one or more shapes can be utilized as a monomer or a crosslinker (e.g., building block) for constructing a matrix. In one embodiment, branched nucleic acids are all of one shape (X-, Y-, dumbbell- or T-shape), which nuclei acids are used as monomers or crosslinkers to form nucleic acid hydrogels. In some embodiments, branched nucleic acids are prepared through the hybridization of the complimentary sequences of the pre-designed oligonucleotides (Table 3). In some embodiments, the nucleic acids are DNA, RNA, PNA, LNA or TNA. In additional embodiments, one or more combinations of such nucleic acids can be utilized as building blocks. In further embodiments, the monomers are linked to other monomers by ligation. Therefore, the monomers can undergoe a ligation reaction facilitated by a nucleic acid ligase.

Thus, the nucleic acids are capable of undergoing enzymatic reactions. In some embodiments, the reactions include reactions by enzymes, wherein said one or more enzyme is a DNA polymerase, RNA reverse transcriptase, terminal transferase, DNA ligase, RNA ligase, exonuclease, ribonuclease, endonuclease, polynucleotide kinase, DNA methylase, or DNA ubiquitinase. Furthermore, reactions include any reaction wherein one or more enzyme is an enzyme that shortens nucleic acids, lengthens nucleic acids, amplifies nucleic acids, labels nucleic acids, or a combination of reactions/enzymes thereof.

In one aspect of the invention, a matrix comprises different shape nucleic acid molecules, ratios for which can be selected to predetermine the geometrical pattern, chemical and physical properties for the resulting matrix. For example, a matrix can be comprised of a ratio of monomers of X- and Y-shaped, X- and T-shaped, X- and dumbbell-shaped, Y- and T-shaped, Y- and dumbbell-shaped, or T- and dumbell shaped nucleic acids. In such embodiments, each monomer can be DNA, RNA, PNA, LNA, TNA or analogs thereof. In one embodiment, the matrix is comprised of DNA. In another embodiment, the matrix is comprised of RNA and DNA. In yet another embodiment, the matrix is comprised of RNA. Therefore, one or more matrixes can be entirely comprised of nucleic acids molecules of one type or a combination of types (e.g., DNA, RNA types, etc.).

In one embodiment, the resulting matrix is three-dimensional. In another embodiment, the resulting matrix is capable of gelling. In yet another embodiment, the resulting matrix is a hydrogel. In yet further aspects of the invention, as disclosed herein, any one or more matrixes of the present invention can be linked to a copolymer or additional chemical moieties. Furthermore, the nucleic acid molecules of the one or more matrices of the present invention can be linear, X-shape, Y-shape, T-shape, dumbbell-shape, denrimer shape or any combination thereof. The following nonlimiting examples provide some of the characteristics for nucleic acid molecules (e.g., building blocks) that may be utilized in one or more compositions or methods disclosed herein.

X-Shape

In one aspect of the present invention, a matrix of the present invention is comprised entirely or at least in part of branched nucleic acids that are X-shape nucleic acids. In one embodiment, the X-shape nucleic acid is DNA. In yet another embodiment, the matrix is comprised of X-shape DNA and/or RNA, or analogs/derivative thereof. In another embodiment, the matrix is comprised of X-shape DNA, and linear DNA, RNA or PNA. In one preferred embodiment, the matrix is nearly entirely comprised of nucleic acids. In yet another embodiment, the X-shape nucleic acids are RNA.

In another aspect, the matrix is comprised of X-shape and linear nucleic acids and at least one copolymer. In one embodiment, the X-shape and linear nucleic acid is DNA. In another embodiment, the X-shape nucleic acid is DNA, while the linear nucleic acid is DNA, RNA or PNA. The at least one copolymer is selected from those known in the art or as disclosed herein above. In one embodiment, the copolymer is a peptide monomer.

In addition, certain aspects of the invention are directed to the X-shape nucleic acid being "reinforced" to produce a more stable and resilient scaffold or matrix, by linking a nanoparticle to the nucleic acid. In one embodiment, the X-shape nucleic acid is DNA. In another embodiment, the X-shape nucleic acid is RNA. In a preferred embodiment, the X-shape DNA is linked to a nanoparticle that is a metal. In another preferred embodiment, the metal is silver, gold or copper.

In one embodiment, four different oligonucleotides with complimentary sequences, termed as X01, X02, X03, and X04 (Table 3), are hybridized with each other o through an annealing process to achieve the final X-DNA. Furthermore, a plurality of said X-DNA can be linked via same or different linear DNA, which can be varied by sequence and/or size, to construct a unique matrix or networked matrix. (e.g., FIG. 8A).

In certain aspects of the invention, the X-DNA terminal ends are designed with sticky ends that are capable of undergoing an enzymatic reaction. In one embodiment, the enzymatic reaction is a ligation reaction with a DNA ligase, which results in covalent linkage of two or more monomers. In yet a further embodiment, the DNA ligase is a T4 DNA ligase.

In one aspect, X-shaped nucleic acids utilized in building a matrix result in the matrix comprising a tensile modulus of about 0.4 and tensile strength of about 42%. In one embodiment, X-DNA utilized to build a matrix comprise tensile strength (ultimate elongation) of about 35, 36, 37, 38, 39, 40, 41, 42, 43, 44, 45, 46, 47, 48, 49, or 50%, whereby the percentage refers to its own length (stretch).

In one embodiment, X-DNA molecules can be designed and synthesized in such a way that each arm of the X-DNA possessed a complimentary sticky end whose sequences are palindromic.

X-shaped nucleic acid molecules can be synthesized by mixing equal amounts of four oligonucleotide strands. The nomenclature is as follows: $X_{0a}$, $X_{0b}$, $X_{0c}$, and $X_{0d}$ are the four corresponding single oligonucleotide chains that form a $X_0$-nucleic acid molecule ($X_0$). Similarly, $X_{1a}$, $X_{1b}$, $X_{1c}$, and $X_{1d}$ are the four corresponding single oligonucleotide chains that form an $X_1$-nucleic acid molecule ($X_1$); and $X_{na}$, $X_{nb}$, $X_{nc}$, and $X_{nd}$ are the four corresponding single oligonucleotide chains that form a $X_n$-shaped nucleic acid molecule ($X_n$). The reactions can be the following: $X_{0a}+X_{0b}+X_{0c}+X_{0d} \rightarrow X_0$, $X_{1a}+X_{1b}+X_{1c}+X_{1d} \rightarrow X_1$, and $X_{na}+X_{nb}+X_{nc}+X_{nd} \rightarrow X_n$, etc. (see FIGS. 24 and 25).

For the X-shaped nucleic acid molecule, the region 2 of each polynucleotide is complementary to region 3 of one of the other three polynucleotides. For example, with reference to the sequences in Tables 5 and 6: region 2 of SEQ ID NO: 56 is complementary to region 3 of SEQ ID NO:59, region 2 of SEQ ID NO: 57 is complementary to region 3 of SEQ ID NO:56, region 2 of SEQ ID NO: 58 is complementary to region 3 of SEQ ID NO: 57; and region 2 of SEQ ID NO: 59 is complementary to region 3 of SEQ ID NO: 58.

In one embodiment, the length of each of the regions can vary. For example, in some embodiments, the second and/or third regions for the X-shaped nucleic acid molecule and the second and/or fourth regions of the T-shaped nucleic acid molecules are about 13 nucleotides each in length. In some embodiments, the lengths of these regions may be 7, 8, 9, 10, 11, 12, 13, 14, 15, 16, 17, 18, 19, or 20 nucleotides in length. In some embodiments, these regions may be larger than 20 nucleotides in length, for example they may be about 25, 30, 35, 40, 45, or 50 nucleotides in length.

TABLE 4

Sequences of Oligonucleotides

| Strand | SEQ ID NO: | Region 1 | Region 2 3 | Region 4 |
|---|---|---|---|---|
| $T_{0a}$ | 44 | 5'-ACTG | CTGGATCG GTC TATGCGTA | TGGACGTCTACCG TGT-3' |
| $T_{0b}$ | 45 | 5'-CAGT | GCAGGCT | ACGCATACCATCC AG-3' |
| $T_{0c}$ | 46 | 5'-ACTG | ACACGGTA GACGTCCA | GCCTGC-3' |

TABLE 5A

Sequence Table

| SEQ ID NO | Sequence |
|---|---|
| 44 | 5'-ACTGCTGGATCGTATGCGTAGTCTGGACGTCTACCG TGT-3' |
| 45 | 5'-CAGTGCAGGCTACGCATACCATCCAG-3' |
| 46 | 5'-ACTGACACGGTAGACGTCCAGCCTGC-3' |
| 47 | 5'-ACTG-3' |
| 48 | 5'-CAGT-3' |
| 49 | 5'-CTGGATCGTATGCGTA'3' |
| 50 | 5'-GCAGGCT-3' |
| 51 | 5'-ACACGGTAGACGTCCA-3' |
| 52 | 5'-GTC-3' |
| 53 | 5'-TGGACGTCTACCGTGT-3' |
| 54 | 5'-ACGCATACCATCCAG-3' |
| 55 | 5'-GCCTGC-3' |

TABLE 5B

Sequences of Oligonucleotides

| Strand | SEQ ID NO | Region 1 | Region 2 | Region 3 |
|---|---|---|---|---|
| $X_{0a}$ | 56 | 3'-TCGA | AGGCTGATTCGGT | TAGTCCATGA GTC-5' |
| $X_{0b}$ | 57 | 3'-AATT | GACTCATGGACTA | TCATGCGGAT CCA-5' |
| $X_{0c}$ | 58 | 3'-AGCT | TGGATCCGCATGA | CATTCGCCGT AAG-5' |
| $X_{0d}$ | 59 | 3'-GATC | CTTACGGCGAATG | ACCGAATCAG CCT-5' |

TABLE 6

Sequence Table

| SEQ ID NO | Sequence |
|---|---|
| 56 | 3'-TCGAAGGCTGATTCGGTTAGTCCATGAGTC-5' |
| 57 | 3'-AATTGACTCATGGACTATCATGCGGATCCA-5' |
| 58 | 3'-AGCTTGGATCCGCATGACATTCGCCGTAAG-5' |
| 59 | 3'-GATCCTTACGGCGAATGACCGAATCAGCCT-5' |
| 60 | 3'-TCGA-5' |
| 61 | 3'-AATT-5' |
| 62 | 3'-AGCT-5' |
| 63 | 3'-GATC-5' |
| 64 | 3'-AGGCTGATTCGGT-5' |
| 65 | 3'-GACTCATGGACTA-5' |
| 66 | 3'-TGGATCCGCATGA-5' |

TABLE 6-continued

Sequence Table

| SEQ ID NO | Sequence |
|---|---|
| 67 | 3'-CTTACGGCGAATG-5' |
| 68 | 3'-TAGTCCATGAGTC-5' |
| 69 | 3'-TCATGCGGATCCA-5' |
| 70 | 3'-CATTCGCCGTAAG-5' |
| 71 | 3'-ACCGAATCAGCCT-5' |

Thus, X-DNA can ligate with each other via T4 DNA ligase, resulting in a DNA hydrogel. Note that irrespective of the kind of DNA building blocks used (e.g., X-, Y-, dumbbell- or T-shape), the gelation of all DNA hydrogels can be completed at room temperature and neutral pH within 2 hours. In one embodiment, the hydrogel gelation can depend on the activity of the ligase enzyme. Thus, by increasing 2 times the amount of ligase, the DNA hydrogel can be essentially completely formed within 30 minutes. For example, in control experiments including 1) X-DNA without T4 ligase, 2) X-DNA with sticky ends that were not complementary to each other but with T4 ligase, and 3) T4-ligase alone without DNA; gelation (e.g., gel formation) did not occur. Therefore, the complementary sticky ends and ligases were responsible for the gel formation.

In some embodiments, linear nucleic acids, Y-shape, T-shape, dumbell-shape or dendrimer shape nucleic acids having the necessary sticky ends can also be incorporated into a matrix or gel structure formed of X-shape nucleic acids. Therefore, in some embodiments, the matrix is comprised of X-shape and one or more other shapes in a ratio of each monomer that is preselected as desired. (e.g., FIG. 29C).

Y-Shape

In another aspect, the nucleic acids comprising a matrix are Y-shape nucleic acids. In one embodiment, the Y-shape nucleic acid is DNA. In yet another embodiment, the matrix comprises Y-shape DNA and/or RNA, or analogs/derivatives thereof. In another embodiment, the matrix is comprised of Y-shape DNA, and linear DNA or RNA. In one embodiment, the matrix is comprised entirely of nucleic acids that are Y-shape. In a further embodiment, the matrix can comprise Y-shape and X-shape nucleic acids, in a ratio that is preselected as desired.

In one embodiment, dendrimer-line DNA (DL-DNA) is assembled by ligation of Y-DNA molecules, whose sequences are specifically designed so that ligations between Yi and Y-DNA could only occur when i≠j, where i and j refer to the generation number n, for example, G1, G2, etc. The cohesive end of each oligonucleotide is non-palindromic, thus no self-ligations occurred. In addition, the ligation can only occur in one direction, that is, Y0☐Y1☐Y2☐Y3Y4 and so on. Furthermore, when Y0 is ligated to Y1 with a 1:3 molar stoichiometry, one Y0 was linked with three Y1, forming the first-generation DL-DNA. G1 is then ligated to six Y2 (one Y2 for each of the six free branches of G1), resulting in a second-generation DL-DNA (G2). The third (G3), fourth (G4), and higher generation DL-DNA were assembled in a similar way. Note that the assembled DL-DNA (Gn) had only one possible conformation due to the unidirectional ligation strategy. The general format of the nth-generation DL-DNA is Gn=(Y0)(3Y1)(6Y2) . . . (3☐2n−1Yn), where n is the generation number and Yn is the nth Y-DNA. The total number of Y-DNA in an nth-generation DL-DNA is 3☐2n−2. The growth of DL-DNA from nth generation to (n+1)th generation requires a total of 3☐2n new Yn+1-DNA.

Three specific polynucleotides are combined to form each Y-DNA. Each polynucleotide may include three regions. A first region (region 1) of each polynucleotide may include nucleotides that will form a 5' sticky end when a Y-DNA is formed. A "sticky end" is a single-stranded overhang portion of one of the polynucleotides. In various embodiments, the sticky ends for any X-, Y-, T- or dumbbell-shape nucleic acid can be 1, 2, 3, 4, 5, 6, 7, 8, 9, or 10 nucleotides. In some embodiments, a polynucleotide may not have this sticky end. In general, a shorter sticky end will allow for less selectivity in binding. For example, a polynucleotide lacking a sticky end would have little to no selectivity. The sticky end in some embodiments is a four nucleotide sticky end.

The sticky end in some embodiments is a four nucleotide sticky end. In some embodiments, the sticky end includes, or is, TGAC, GTCA, CGAT, ATCG, GCAT, ATGC, TTGC, GCAA, or GGAT (e.g., Tables 4, 5 or 6).

The second region (region 2) of each polynucleotide is complementary to the third region (region 3) of one of the other two polynucleotides that form the Y-DNA. The third region of each polynucleotide is complementary to the second region of the other of the other two polynucleotides of Y-DNA. For example, with reference to the sequences in Tables 7A and 7B: region 2 of SEQ ID NOs 72-76, represented by SEQ ID NO:96, is complementary to region 3 of SEQ ID NOs 82-86, represented by SEQ ID NO:101, region 3 of SEQ ID NOs 72-76, represented by SEQ ID NO:97, is complementary to region 2 of SEQ ID NOs 77-81, represented by SEQ ID NO:98; and region 2 of SEQ ID NOs 82-86, represented by SEQ ID NO:100, is complementary to region 3 of SEQ ID NOs 77-81, represented by SEQ ID NO:99.

In some embodiments of the invention, the length of each of the regions can vary. For example, in some embodiments, the second and/or third regions are about 13 nucleotides each in length. In some embodiments, the lengths of the second and/or third regions may be 7, 8, 9, 10, 11, 12, 13, 14, 15, 16, 17, 18, 19, or 20 nucleotides in length. In some embodiments of the invention, the second and/or third regions may be larger than 20 nucleotides in length, for example they may be about 25, 30, 35, 40, 45, or 50 nucleotides in length.

In one embodiment of the invention, each polynucleotide is 30 nucleotides in length, with the first region having 4 nucleotides, the second region having 13 nucleotides, and the third region also having 13 nucleotides. In some embodiments of the invention, the Y-shape polynucleotides include, essentially include, or are comprised of SEQ ID NOs:75-SEQ ID NO: 89, or SEQ ID NOs: 102-112. With respect to any of the nucleic acid building blocks described herein (e.g., X-, Y-, T-, dumbbell-, dendrimer-shape), in various embodiments, the 5' end can comprise a phosphorylation modification so as to include various labels disclosed here, including Alex488, BO630 (See, probes/labels, supra).

TABLE 7A

Sequences of Oligonucleotides

| Strand | SEQ ID NO: | Region 1 | Region 2 | Region 3 |
|---|---|---|---|---|
| $Y_{0a}$ | 72 | 5'-TGAC | TGGATCCGCATGA | CATTCGCCGTAAG-3' |
| $Y_{1a}$ | 73 | 5'-GTCA | TGGATCCGCATGA | CATTCGCCGTAAG-3' |
| $Y_{2a}$ | 74 | 5'-ATCG | TGGATCCGCATGA | CATTCGCCGTAAG-3' |

TABLE 7A-continued

Sequences of Oligonucleotides

| Strand | SEQ ID NO: | Region 1 | Region 2 | Region 3 |
|---|---|---|---|---|
| $Y_{3a}$ | 75 | 5'-ATGC | TGGATCCGCATGA | CATTCGCCGTAAG-3' |
| $Y_{4a}$ | 76 | 5'-GCAA | TGGATCCGCATGA | CATTCGCCGTAAG-3' |
| $Y_{0b}$ | 77 | 5'-TGAC | CTTACGGCGAATG | ACCGAATCAGCCT-3' |
| $Y_{1b}$ | 78 | 5'-CGAT | CTTACGGCGAATG | ACCGAATCAGCCT-3' |
| $Y_{2b}$ | 79 | 5'-GCAT | CTTACGGCGAATG | ACCGAATCAGCCT-3' |
| $Y_{3b}$ | 80 | 5'-TTGC | CTTACGGCGAATG | ACCGAATCAGCCT-3' |
| $Y_{4b}$ | 81 | 5'-GGAT | CTTACGGCGAATG | ACCGAATCAGCCT-3' |
| $Y_{0c}$ | 82 | 5'-TGAC | AGGCTGATTCGGT | TCATGCGGATCCA-3' |
| $Y_{1c}$ | 83 | 5'-CGAT | AGGCTGATTCGGT | TCATGCGGATCCA-3' |
| $Y_{2c}$ | 84 | 5'-GCAT | AGGCTGATTCGGT | TCATGCGGATCCA-3' |
| $Y_{3c}$ | 85 | 5'-TTGC | AGGCTGATTCGGT | TCATGCGGATCCA-3' |
| $Y_{4c}$ | 86 | 5'-GGAT | AGGCTGATTCGGT | TCATGCGGATCCA-3' |

TABLE 7B

Sequence Table

| SEQ ID NO | Sequence |
|---|---|
| 72 | 5'-TGACTGGATCCGCATGACATTCGCCGTAAG-3' |
| 73 | 5'-GTCATGGATCCGCATGACATTCGCCGTAAG-3' |
| 74 | 5'-ATCGTGGATCCGCATGACATTCGCCGTAAG-3' |
| 75 | 5'-ATGCTGGATCCGCATGACATTCGCCGTAAG-3' |
| 76 | 5'-GCAATGGATCCGCATGACATTCGCCGTAAG-3' |
| 77 | 5'-TGACCTTACGGCGAATGACCGAATCAGCCT-3' |
| 78 | 5'-CGATCTTACGGCGAATGACCGAATCAGCCT-3' |
| 79 | 5'-GCATCTTACGGCGAATGACCGAATCAGCCT-3' |
| 80 | 5'-TTGCCTTACGGCGAATGACCGAATCAGCCT-3' |
| 81 | 5'-GGATCTTACGGCGAATGACCGAATCAGCCT-3' |
| 82 | 5'-TGACAGGCTGATTCGGTTCATGCGGATCCA-3' |
| 83 | 5'-CGATAGGCTGATTCGGTTCATGCGGATCCA-3' |
| 84 | 5'-GCATAGGCTGATTCGGTTCATGCGGATCCA-3' |
| 85 | 5'-TTGCAGGCTGATTCGGTTCATGCGGATCCA-3' |
| 86 | 5'-GGATAGGCTGATTCGGTTCATGCGGATCCA-3' |
| 87 | 5'-TGAC-3' |
| 88 | 5'-GTCA-3' |
| 89 | 5'-CGAT-3' |
| 90 | 5'-ATCG-3' |
| 91 | 5'-GCAT-3' |
| 92 | 5'-ATGC-3' |
| 93 | 5'-TTGC-3' |
| 94 | 5'-GCAA-3' |
| 95 | 5'-GGAT-3' |
| 96 | 5'-TGGATCCGCATGA-3' |
| 97 | 5'-CATTCGCCGTAAG-3' |
| 98 | 5'-CTTACGGCGAATG-3' |
| 99 | 5'-ACCGAATCAGCCT-3' |
| 100 | 5'-AGGCTGATTCGGT-3' |
| 101 | 5'-TCATGCGGATCCA-3' |
| 102 | TTGCTGGATCCGCATGACATTCGCCGTAAG-3' |
| 103 | CGTTTGGATCCGCATGACATTCGCCGTAAG-3' |
| 104 | ATGCTGGATCCGCATGACATTCGCCGTAAG-3' |
| 105 | TGGATCCGCATGACATTCGCCGTAAG-3' |
| 106 | GCATCTTACGGCGAATGACCGAATCAGCCT-3' |
| 107 | GCAACTTACGGCGAATGACCGAATCAGCCT-3' |
| 108 | CTTACGGCGAATGACCGAATCAGCCT-3' |
| 109 | GCATAGGCTGATTCGGTTCATGCGGATCCA-3' |
| 110 | TTGCAGGCTGATTCGGTTCATGCGGATCCA-3' |
| 111 | AACGAGGCTGATTCGGTTCATGCGGATCCA-3' |
| 112 | AGGCTGATTCGGTTCATGCGGATCCA-3' |

In another aspect, the matrix is comprised of Y-shape and linear nucleic acids and at least one copolymer. In one embodiment, the Y-shape and linear nucleic acid is DNA. In another embodiment, the Y-shape nucleic acid is DNA, while the linear nucleic acid is DNA, RNA, TNA or PNA. Furthermore, the at least one copolymer is selected from those known in the art or as disclosed herein above. In one embodiment, the copolymer is a peptide monomer, as known in the art or disclosed herein above.

In certain aspects of the invention, the Y-DNA terminal ends are designed with sticky ends as described above that are capable of undergoing an enzymatic reaction. In one embodiment, the enzymatic reaction is a ligation reaction with a DNA ligase. In yet a further embodiment, the DNA ligase is a T4 DNA ligase.

In one embodiment, Y-shape nucleic acid building blocks are joined end-to-end to produce a dumbell shaped building block or dendrimer like nucleic acid. (e.g., FIGS. 9 and 30B)

In one aspect, Y-shaped nucleic acid building blocks form a matrix having a tensile modulus of about 0.4 and tensile strength of about 42%. In one embodiment, Y-nucleic acids utilized to build a matrix comprise tensile strength of about 35, 37, 38, 39, 40, 41, 42, 43, 44, 45, 46, 47, 48, 49, 50, 51, 52, 53, 54, 55, 56, 57, 58, 59 or 60%. In one embodiment, the Y-shaped nucleic acids are DNA. In another, embodiment, the Y-shaped nucleic acids are RNA.

Figure 14:
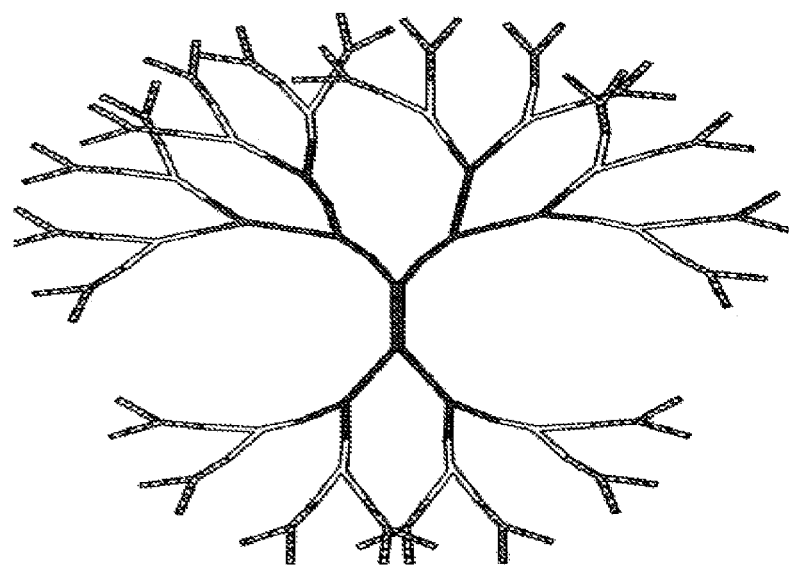
FIG. 14. Shows a dendrimer structure.
Figure 15:
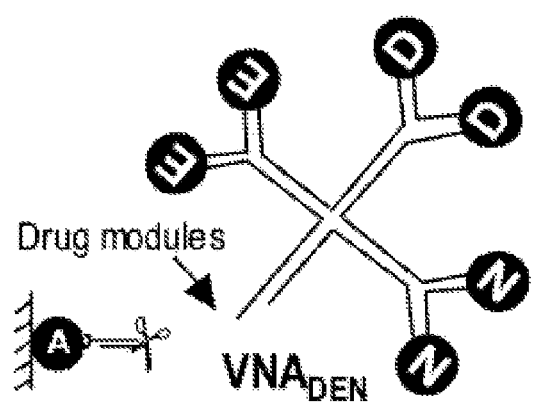
FIG. 15. Shows a dendrimer like structure comprised of nucleic acids with terminal Y-shape arms with various compounds linked to the plurality of arms.
Figure 16:
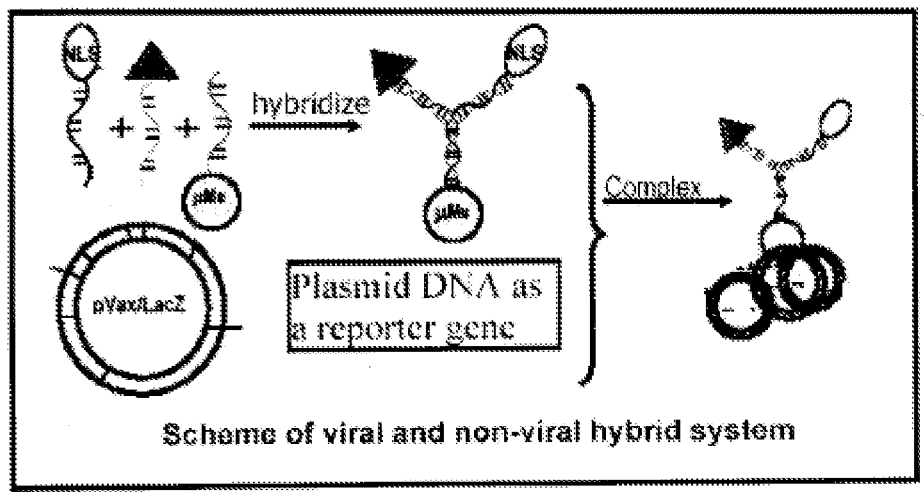
FIG. 16. Shows a Y-shape DNA linked to various compounds, including a circular vector DNA linked to the Y-DNA via a μMu component.

In another aspect, the Y-shape nucleic acids of the invention are used to form a dendrimer structure. Branched nucleic acids described herein are dendrimer like, thus by combining such nucleic acids in a step-wise or all in one fashion, dendrimer structure are formed. Furthermore, in some embodiments, the various arms of said Y-shape nucleic acids, as comprised on in a dendrimer structure, are linked to one or more biologically active agents, which agents are described herein. Thus, in one embodiment, the arms are linked to a targeting peptide or signal peptide, a selection marker, a detectable label, a small compound, a drug, a pharmaceutical or to a plasmid or viral vector, or virus. It should be apparent to one of skill in the art that the Y-shape nucleic acids forming said dendrimer afford attachment of multiple same or different compounds (FIGS. 14-16). In other words, the dendrimer structures are anisotropic and/or multivalent. In other embodiments, X-shaped, T-shaped or dumbbell-shaped nucleic acids are utilized to from dendrimer structures.

In one embodiment the Y-shape, X-shape, T-shape or dumbbell-shape arms are attached to a peptide moiety comprising an adenovirus core peptide, a synthetic peptide, an influenza virus HA2 peptide, a simian immunodeficiency virus gp32 peptide, an SV40 T-Ag peptide, a VP22 peptide, a Tat peptide, a Rev peptide, DNA condensing peptide, DNA protection peptide, endosomal targeting peptide, membrane fusion peptide, nuclear localization signaling peptide, a protein transduction domain peptide or any combination thereof.

In another embodiment, the Y-shape, T-shape, X-shape or dumbbell shape nucleic acids are linked to one or more biologically active agents, including the preceding peptides, one or more selection markers, one or more detectable labels, one or more drugs, small compounds, or nucleic acid sequences or one or more copolymer compounds.

T-Shape

Figure 10:
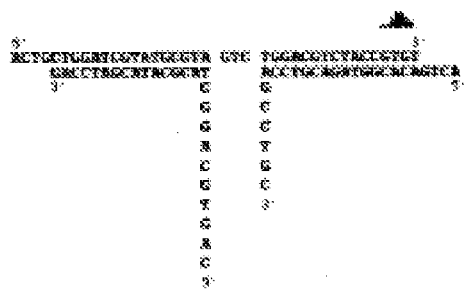
FIG. 10. Shows a T-shape DNA (SEQ ID NOs: 46).
Figure 11:
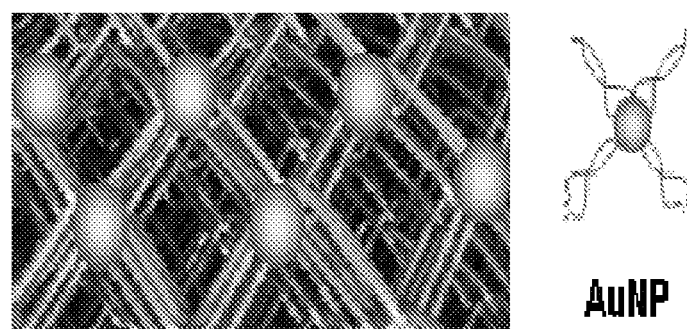
FIG. 11. Shows a networked matrix of X-shape nucleic acids, with AuNP integrated into the matrix.
Figure 12:
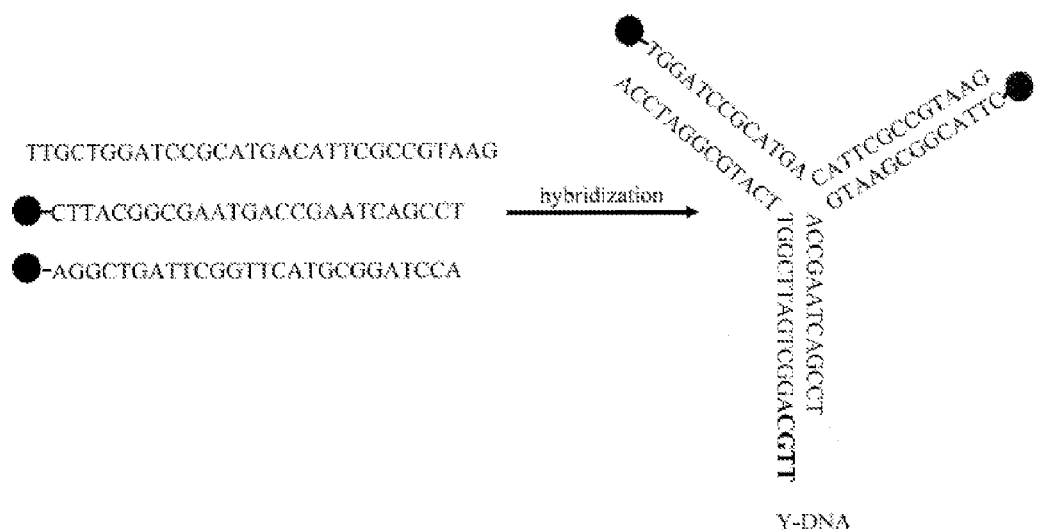
FIGS. 12 and 13. Show a Y-shape DNA (SEQ ID NOs: 102, 108 and 112).
Figure 13:

In yet another aspect, the nucleic acids forming a matrix are T-shape nucleic acids (FIG. 10). In one embodiment, the T-shape nucleic acids are DNA. In yet another embodiment, the matrix comprises T-shape DNA and/or RNA, or analogs/derivatives thereof. In addition, a matrix can be comprised of T-shape and one or more different shapes of nucleic acids, including X-, Y-, dumbell- or dendrimer-shape nucleic acids, as well as a combination thereof.

In one embodiment, the T-shape nucleic acids have a tensile strength selected from 50, 51, 52, 53, 54, 55, 56, 57, 58, 59, 60, 61, 62, 63, 64, or 65%. In addition, the T-shape nucleic acids can have a degree of swelling selected from 100, 105, 110, 115, 120, 125, 130, or 135%. For the T-shaped nucleic acid molecule, the second region (region 2) of each polynucleotide is complementary to the fourth region (region 4) of one of the other two polynucleotides. The fourth region of each polynucleotide is complementary to the second region of the other of the other two polynucleotides of T-shaped nucleic acid molecule. The third region is either absent or is a linker to permit formation of the T-shaped configuration. For example, with reference to the sequences in Tables 4 and 5A: region 2 of SEQ ID NO: 46 is complementary to region 4 of SEQ ID NO: 44, region 4 of SEQ ID NO: 46 is complementary to region 2 of SEQ ID NO: 45, and region 2 of SEQ ID NO: 44 is complementary to region 4 of SEQ ID NO: 45.

T-shaped nucleic acid molecules can be synthesized by mixing equal amounts of three oligonucleotide strands. The nomenclature is as follows: $T_{0a}$, $T_{0b}$, and $T_{0c}$ are the three corresponding single oligonucleotide chains that form a $T_0$-nucleic acid molecule ($T_0$). Similarly, $T_{1a}$, $T_{1b}$, and $T_{1c}$ are the three corresponding single oligonucleotide chains that form a $T_1$-nucleic acid molecule ($T_1$); and $T_{na}$, $T_{nb}$, and $T_{nc}$ are the three corresponding single oligonucleotide chains that form a $T_n$-shaped nucleic acid molecule ($T_n$). The reactions can be the following: $T_{0a}+T_{0b}+T_{0c} \rightarrow T_0$, $T_{1a}+T_{1b}+T_{1c} \rightarrow T_1$, and $T_{na}+T_{nb}+T_{nc} \rightarrow T_n$, etc. (see FIGS. 10 and 26).

In various embodiments, selection of X-, Y- or T-DNA can be utilized to design hydrogels of differing external morphologies and internal structure. (e.g., FIGS. 1, 2 and 5). For example, in a dry state surface morphology revealed a tangled pattern for X-DNA gel (FIG. 5A), a fibrous form for Y-DNA gel, and a scale shape for T-DNA gel. (FIG. 5). Furthermore, X-DNA gels can exhibit two flat DNA gel strips tangled into a knot to form a large sheet with many wrinkles on the surface. Y-DNA gel (FIG. 5B) exhibits fibrous a fibrous form spreading out from many branches. T-DNA gel (FIG. 5C) exhibits puckers on a sheet. In a swollen state, the surface morphology of the gels exhibited a large number of various sized pores and channels (FIG. 5D), with obvious fibers of fractal-shapes on the periphery (FIG. 5E) and perpendicularly erected, scale like structures (FIG. 5F) for X-, Y- and T-DNAs.

In yet other embodiments, gels can be comprised of one or more differently shaped nucleic acids, including X-, Y-, T-, dumbell- or dendrimer-shaped DNA (e.g., Y- and X-DNA, or Y- and T-DNA or X- and T-DNA). In yet further embodiments, applicable to any matrix disclosed herein, gels can be comprised of nucleic acids that include DNA, RNA, PNA, TNA, or a combination thereof.

Matrix Pore Size

In another aspect of the invention, by selecting a particular nucleic acid or combination of nucleic acids to construct a matrix, the resulting matrix comprises pores. In one embodiment, the pores are of a size selected from 5 nm, about 10 nm, about 15 nm, about 20 nm, about 30 nm, about 40 nm, about 50 nm, and about 100 nm. In yet another embodiment, said pores have a size selected from a group consisting of about 0.1 micron to about 5 microns, about 10 microns, about 20 microns, about 30 microns, about 40 microns, about 50 microns, about 100 microns, about 200 microns, about 300 microns, about 400 microns, about 500 microns, 600 microns and about 1000 microns. Therefore, by selecting different length monomers and/or different shapes, a matrix can be constructed having substantially predetermined pore sizes.

In another aspect of the invention, methods are directed to producing three-dimensional matrices by utilizing branched nucleic acids, in particular X-, Y-, T-, dumbbell-, or dendrimer-nucleic acids as the building blocks that form said three-dimensional matrices. In one embodiment, the nucleic acids are DNA molecules. In another embodiment, the nucleic acids are RNA and/or PNA. Furthermore, the nucleic acids can be a combination of DNA, RNA or PNA, or any other nucleic acids disclosed herein. In another embodiment, said matrices comprise linear nucleic acids that encode one or more proteins.

In one aspect, the three-dimensional matrix structure is designed to comprise certain pore sizes based on selection of the particular nucleic-acid based building blocks, wherein a matrix (hydrogel) is comprised of a single shape monomer building block, which monomer can be X-, Y-, T-, dumbbell- or dendrimer-shape, or a combination thereof. In one embodiment, the nucleic acids are X and Y shapes and provided in predetermined ratios so as to provide a network matrix structure resulting in a predictable pore size or range of pore sizes. In another embodiment, the nucleic acids further include linear nucleic acids utilized concomitantly with the various shapes selected from X-, Y-, Y-, dumbell-, dendrimer-shapes, or a combination thereof. In another embodiment, the network matrix structure is hydradable, whereby a dry compound comprising the nucleic acid-based matrix swells in volume (with water or similar liquid) from about 100, 200, 300, 400, 500, 600, 700, 800, 900, 1000, 1100, 1200, 1300, 1400, 1500%.

Hydrogel Swelling

DNA incorporation and the degree of swelling of the DNA hydrogels. The swelling degree Q of the DNA hydrogel was calculated from:

$$Q = 1 + \rho_2 \cdot \left( \frac{m_{sw}}{m_d \cdot \rho_1} - \frac{1}{\rho_1} \right)$$

where $m_{sw}$ is the weight of the sample in the swollen state, $m_d$ is the weight of the dry extracted sample, and $\rho_1$ and $\rho_2$ are the specific densities of the swelling medium and the polymer, respectively. $\rho_2$ was determined by weighing a sample piece of precisely known length, width, and thickness (A. Lendin, A. M. Schmidt, R. Langer, *Proc Natl Acad Sci USA* 98, 842 (2001)).

The DNA gels were fabricated in a cylindrical mold with a known size and volume. The gels were thoroughly freeze-dried overnight and then weighed. For the swollen gels, 300 μl of fresh water was added into the dried-gel tube and incubated for over a day in order for the DNA gels to swell. All values shown in this table are an average of at least three replicates. N/D means "not determined".

TABLE 8

Hydrogel Swelling

| DNA buildling blocks (initial concentration) | DNA building blocks incorporated (%) | Q (%) |
|---|---|---|
| X-DNA gel (0.2 mM) | 83.05 ± 2.10 | 693.79 ± 8.33 |
| Y-DNA gel (0.2 mM) | 81.07 ± 0.63 | 439.65 ± 7.30 |
| T-DNA gel (0.2 mM) | 80.12 ± 5.15 | 428.19 ± 10.14 |
| X-DNA gel (0.1 mM) | 79.66 ± 5.91 | 531.07 ± 24.17 |
| Y-DNA gel (0.1 mM) | 80.45 ± 3.28 | 281.04 ± 7.53 |
| T-DNA gel (0.1 mM) | 79.67 ± 1.56 | 278.13 ± 9.51 |
| X-DNA gel (0.03 mM) | 79.67 ± 2.78 | N/D |
| Y-DNA gel (0.03 mM) | 79.08 ± 0.60 | 137.05 ± 13.90 |
| T-DNA gel (0.03 mM) | 72.41 ± 4.76 | 132.64 ± 3.73 |

TABLE 9A

Tensile Strength

| DNA Building Blocks (initial concentration) | Specific Gravity | Tensile Modulus (mPa) | Tensile Strength (%) (Ultimate Elongation) |
|---|---|---|---|
| X-DNA gel (0.2 mM) | 1.060 | 0.0415 = 0.0003 | 42.50 ± 1.13 |
| Y-DNA gel (0.2 mM) | 1.033 | 0.0015 = 0.0001 | 48.89 = 0.59 |
| T-DNA gel (0.2 mM) | 1.012 | 0.0104 = 0.0007 | 57.93 = 0.00 |

The specific gravity of a substance is a comparison of its density to that of water. The percentage (ultimate elongation) indicates how close the measurements are made to the point at which the gel breaks.

TABLE 9B

Mechanical properties of dried and swollen hydrogels

| | Specific Gravity | Tensile Modulus (mPa) | Tensile Strength |
|---|---|---|---|
| X-DNA | | | |
| 0.01 dried | N/A | N/A | N/A |
| 0.01 swollen | N/A | N/A | N/A |
| 0.03 dried | 1.699 | 0.07472 | 35.795 |
| 0.03 swollen | 6.830 | 0.008766 | 35.070 |
| 0.05 dried | 2.070 | 0.01767 | 47.764 |
| 0.05 swollen | 13.023 | 0.04174 | 41.909 |
| Y-DNA | | | |
| 0.05 dried | 1.752 | 0.04660 | 34.404 |
| 0.05 swollen | 17.706 | 0.001434 | 41.909 |
| T-DNA | | | |
| 0.05 | 2.07 | 0.03854 | 38.286 |
| 0.05 swollen | 9.394 | 0.01010 | 57.917 |

TABLE 10

Example of Oligonucleotides used to construct X-, Y- and T-nucleic acid building blocks.

| Strand | Segment 1 | Segment 2 | SEQ. ID. NO. |
|---|---|---|---|
| $X_{01}$ | 5'-p-ACGT CGA CCG ATG AAT AGC GGT | CAG ATC CGT ACC TAC TCG-3' | 113 |
| $X_{02}$ | 5'-p-ACGT CGA GTA GGT ACG GAT CTG | CGT ATT GCG AAC GAC TCG-3' | 114 |
| $X_{03}$ | 5'-p-ACGT CGA GTC GTT CGC AAT ACG | GCT GTA CGT ATG GTC TCG-3' | 115 |
| $X_{04}$ | 5'-p-ACGT CGA GAC CAT ACG TAC AGC | ACC GCT ATT CAT CGG TCG-3' | 116 |
| $Y_a$ | 5'-p-ACGT CGA CCG ATG AAT AGC GGT | CAG ATC CGT ACC TAC TCG-3' | 117 |
| $Y_b$ | 5'-p-ACGT CGA GTC GTT CGC AAT ACG | ACC GCT ATT CAT CGG TCG-3' | 118 |
| $Y_c$ | 5'-p-ACGT CGA GTA GGT ACG GAT CTG | CGT ATT GCG AAC GAC TCG-3' | 119 |
| $T_a$ | 5'-p-ACGT CGA CAG CTG ACT AGA GTC | ACG ACC TGT ACC TAC TCG-3' | 120 |
| $T_b$ | 5'-p-ACGT CGA GTC GTT CTC AAG ACG TAG CTA GGA CTC TAG TCA GCT GTC G-3' | | 121 |
| $T_c$ | 5'-p-ACGT CGA GTA GGT ACA GGT CGT | CGT CTT GAG AAC GAC TCG-3 | 122 |

Note that p represents the phosphorylation on the 5' end of the oligonucleotide.

To confirm the formation of these branched DNA building blocks, a gel electrophoretic migration-shift assay (GEMSA) coupled with a DNA-specific fluorescent dye (SYBR I) was employed. The size (molecular weight) and the purity (polydispersity) were assessed (FIG. 1A). Due to their larger size, the mobility of complete X-DNA was much slower (lane 5 in FIG. 1A). Incomplete hybridization of X01, X02, X03, and X04, on the other hand, resulted in a small amount of incomplete X-DNA (see the relatively faint bands below the major ones in lane 5 of FIG. 1A). When all complete X-DNA bands from the gel were collected and evaluated, they represented approximately 80% of the initial amounts of input oligonucleotides. These results matched well with the gel formation data (Table 1) showing that approximately 80% of the DNA building blocks were incorporated into the DNA hydrogel. In addition, the reaction profile of the formation of DNA hydrogels also showed about 20% of unincorporated DNA molecules remaining in the reaction solution (data not shown). In general, lower salt concentrations can be used for more specific base-pairing, while higher salt concentrations favor strong electro-static intereactions. Ionic influences on DNA are familiar to one of ordinary skill in the art. (See, e.g., Macromolecules, 1997, 30: 5763; J. Phys. Chem. 2006; 110: 2918-2926; Biophys. J. 1996; 70: 2838-46.

Similar experiments as above were also performed with Y- and T-DNA, which led to controlled-assembled hydrogels with different properties. For ligation, manufacturer's protocols were followed. Mg++ was added for ATP. Hydrogel gelation correlated with ligase activity. For example, by using twice the amount of ligase (e.g., 60 Units), the DNA hydrogel was completely formed within 30 minutes. Irrespective of the kind of DNA monomer (e.g., X, Y, or T), the gelation of all hydrogels was completed at room temperature and neutral pH within 2 hours. A typical example of ligase reaction utilized Ligase 10× buffer which has a composition of 300 mM Tris-HCl (pH 7.8), 100 mM Mg Cl2, 100 mM DTT and 10 mM ATP. T4 DNA ligase is supplied with 10 mM Tris-HCl (pH 7.4), 50 mM KCl, 1 mM DTT, 0.1 mM EDTA and 50% glycerol.

The amount of DNA building blocks incorporated can be calculated by subtracting the DNA concentration in the supernatant after gelation from the initial DNA concentration after gelation.

Dendrimer Structures

As almost all nucleic acid molecules are either linear or circular, to rationally construct nucleic acid biomaterials, additional shapes of nucleic acids as basic building blocks must be first constructed. In addition, these nucleic acid building blocks must be readily incorporated into larger structures in a controlled manner. Thus, in one aspect of the invention, dendrimer like nucleic acid structures are assembled to provide a biomaterial compound.

In other aspects of the invention branched or DL-NAMs are utilized to form dendrimer structures. Synthesizing monodisperse polymers demands a high level of synthetic control which is achieved through stepwise reactions, building the dendrimer up one monomer layer, or "generation," at a time. Each dendrimer consists of a multifunctional core molecule with a dendritic wedge attached to each functional site. The core molecule is referred to as "generation 0." Each successive repeat unit along all branches forms the next generation, "generation 1," "generation 2," and so on until the terminating generation (e.g., FIG. 14).

There are two defined methods of dendrimer synthesis, divergent and convergent. In the divergent method the molecule is assembled from the core to the periphery; while in the convergent method, the dendrimer is synthesized beginning from the outside and terminating at the core. In either method the synthesis requires a stepwise process, attaching one generation to the last, purifying, and then changing functional groups for the next stage of reaction. For example, in FIG. 14, the shaded inner core represents one step, followed by the unshaded "Y" molecules as an additional and subsequent step, and finally the stipeled "Y" molecules as a further additional and subsequent step. This functional group transformation is necessary to prevent unbridled polymerization. Such polymerization can lead to a highly branched molecule which is not monodisperse—otherwise known as a hyperbranched polymer.

In the divergent method, the surface groups initially are unreactive or protected species which are converted to reactive species for the next stage of the reaction. In the convergent approach the opposite holds, as the reactive species must be on the focal point of the dendritic wedge.

Due to steric effects, continuing to react dendrimer repeat units leads to a sphere shaped or globular molecule until steric overcrowding prevents complete reaction at a specific generation and destroys the molecule's monodispersity. The number of possible generations can be increased by using longer spacing units in the branches of the core molecule. The monodispersity and spherical steric expansion of dendrimers leads to a variety of interesting properties. The steric limitation of dendritic wedge length leads to small molecular sizes, but the density of the globular shape leads to fairly high molecular weights. The spherical shape also provides an interesting study in molecular topology. Dendrimers have two major chemical environments, the surface chemistry due to the functional groups on the termination generation, which is the surface of the dendritic sphere, and the sphere's interior which is largely shielded from exterior environments due to the spherical shape of the dendrimer structure. The existence of two distinct chemical environments in such a molecule implies many possibilities for dendrimer applications.

As such, hydrophobic/hydrophilic and polar/nonpolar interactions can be varied in the two environments. The existence of voids in the dendrimer interior furthers the possibilities of these two heterogeneous environments playing an important role in dendrimer chemistry. Therefore, in a further embodiment dendrimer structures can accept molecules in the void spaces in addition to or alternative to the linkage to one or more arm portions of one or more terminal monomer (e.g., Y-shape) nucleic acid molecules. Dendrimers have found actual and potential use as molecular weight and size standards, gene transfection agents, as hosts for the transport of biologically important guests, and as anti-cancer agents, to name but a few. Much of the interest in dendrimers involves their use as catalytic agents, utilizing their high surface functionality and ease of recovery. Dendrimers' globular shape and molecular topology, however, make them highly useful to biological systems. Utilizing nucleic acid molecules as building blocks for dendrimer construction and further linked to biologically active agents provides wholly new opportunities in biotechnology and medicine.

In some aspects of the invention the dendrimer structures can be formed at any stage during a step-wise process of formulation to provide a multivalent structure. Such a dendrimer structure can be composed of multimers that are Y-, X-, T-, or dumbbell shape.

In one embodiment, the multimers forming said dendrimer structure are DNA multimers. In another embodiment, the dendrimer structure is comprised of DNA and/or RNA. As indicated above, dendrimers are formed through step-wise addition of different nucleic acid monomers (i.e., building blocks), where for example, nucleic acid monomer ends provide overhangs for subsequent ligation reactions thus expanding the three-dimensional structure of the expanding dendrimer structure.

Therefore, in selection various nucleic acids, monomers of different length can be utilized to form dendrimers having a different internal and surface area network. Furthermore, the various sticky ends and/or monomer units can provide a substrate for linking to one or a plurality of biologically active agents. Such biologically active agents are known in the art or described herein.

In one aspect of the invention, a method is directed to controlled assembly of dendrimer-like DNA (DL-DNA) from Y-shaped DNA (Y-DNA) FIGS. 13-16. In one embodiment, the resulting DL-DNA is stable and monodisperse. In a further embodiment, the multivalent DNA dendrimers are either isotropic or anisotropic, thus capable of linkage to other compounds FIG. 14.

In certain embodiments, the dendrimer structures are linked or cross-linked to additional compounds selected from a group consisting of an adenovirus core peptide, a synthetic peptide, an influenza virus HA2 peptide, a simian immunodeficiency virus gp32 peptide, an SV40 T-Ag peptide, a VP22 peptide, a Tat peptide, and a Rev peptide. Such additional compounds are selected from a group consisting of DNA condensing peptide, DNA protection peptide, endosomal targeting peptide, membrane fusion peptide, nuclear localization signaling peptide, a protein transduction domain peptide or a combination thereof (FIGS. 15-16).

In one embodiment, the dendrimer structures are utilized in a method of delivering a biologically active agent to a cell, or to a subject. In another embodiment, the dendrimer structure comprises a linkage to a signal or targeting peptide as described herein above, and comprises a biologically active agent.

In yet another embodiment, the dendrimer comprises a targeting peptide, a biologically active agent, a selection marker and a detectable label. Selection markers include antibiotics which are known in the art for both eukaryotic and prokaryotic cells, or disclosed herein. Infra. Therefore, as noted above, a dendrimer can provide a multivalent structure comprised of several distinct molecules that are bound to one or more arms of a one or more multimer nucleic acid molecules of which a dendrimer is composed. (e.g., FIGS. 15-17).

Figure 17:
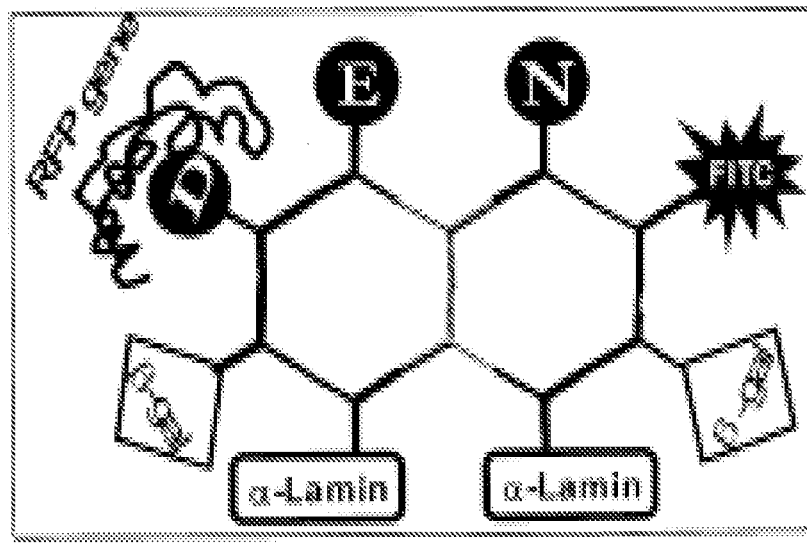
FIG. 17. Multivalent nucleic acid dendrimer for delivery into a cell, and linked to various components.
Figure 18:
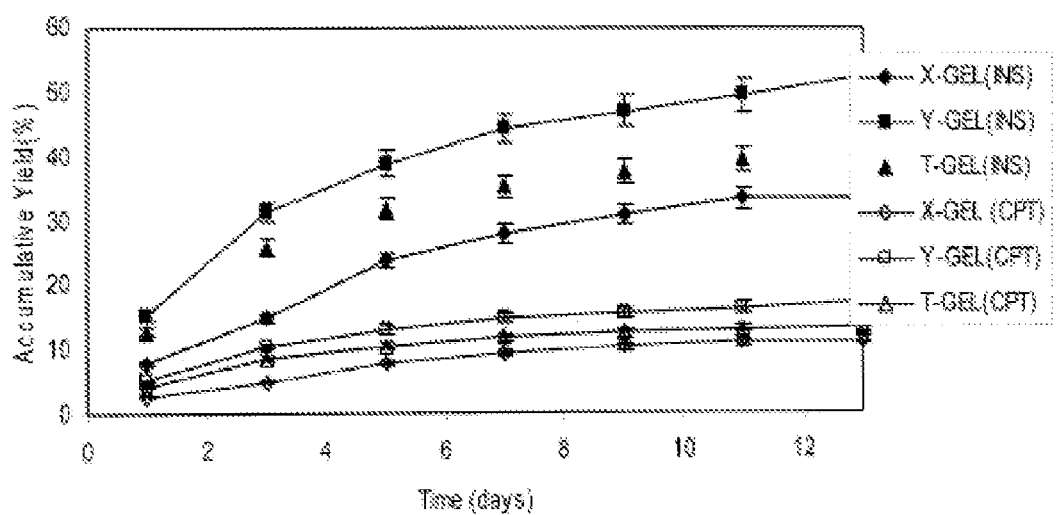
FIG. 18. Drug release profile for from various nucleic acid matrixes.
Figure 19A:
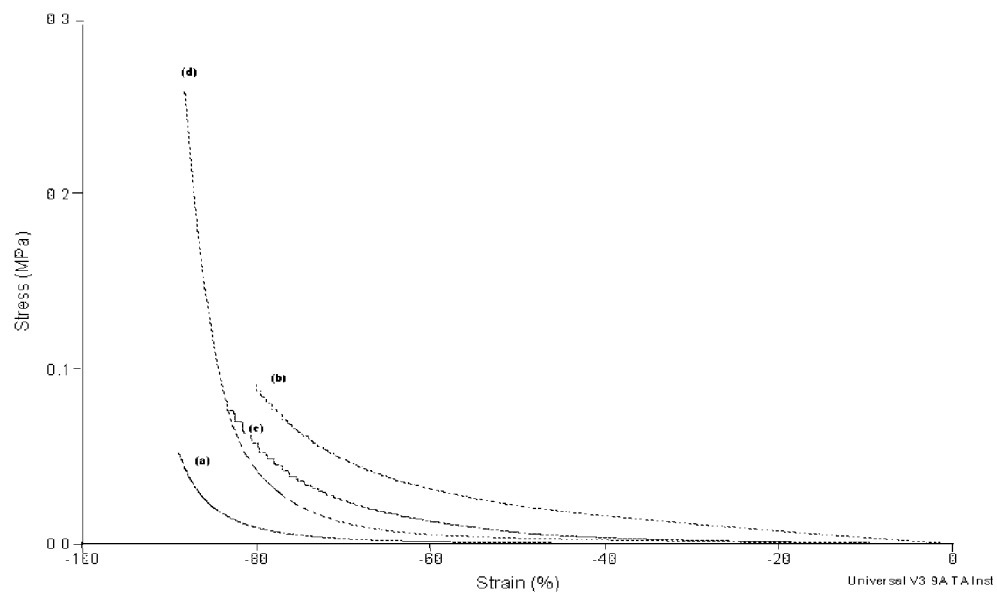
FIG. 19. Stress-Strain Curves Illustrating the Mechanical Properties of P-gel. A: (a) swollen X-DNA gel (0.03 umole); (b) swollen X-DNA gel (0.05 umole); (c) swollen Y-DNA gel (0.05 umole); (d) swollen T-DNA gel (0.05 umole); B: dried X-DNA gel (0.03 umole); (b) dried X-DNA gel (0.05 umole); dried Y-DNA gel (0.05 mmole); (d) T-DNA gel (0.05 umole).
Figure 19B:
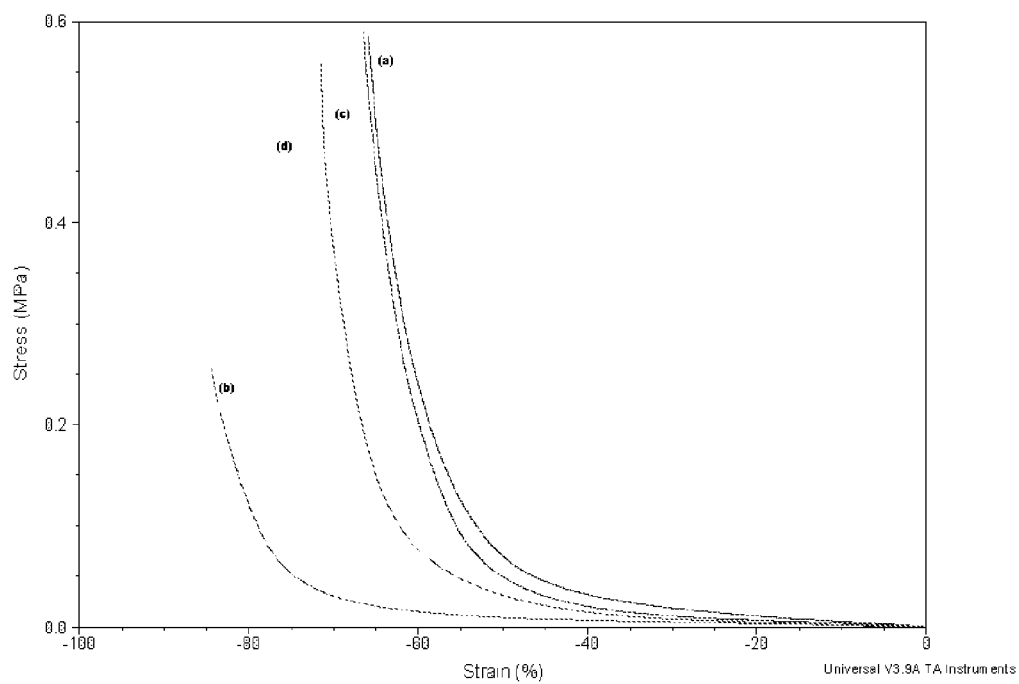
Figure 20A:
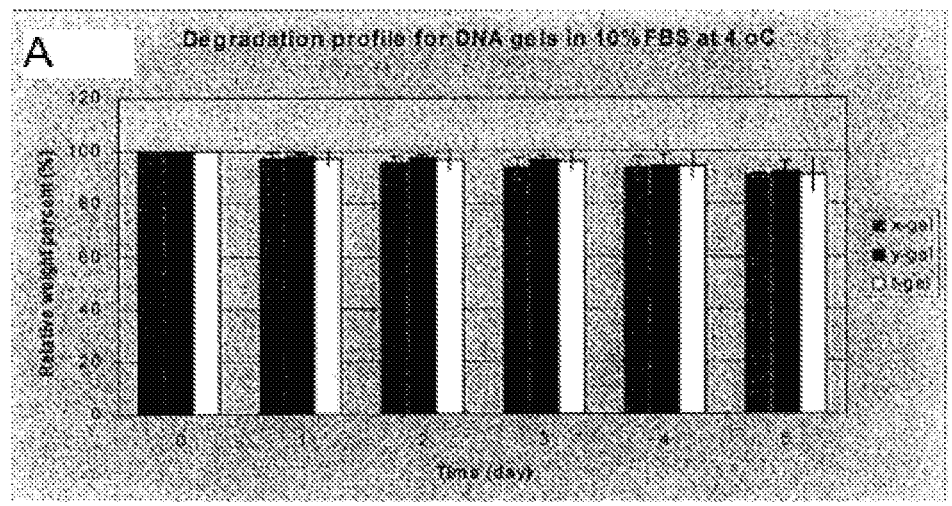
FIG. 20. Degradation Profiles in 10% FES and 1×PBS. A: Degradation for X-, Y- and T-gels appears stable over 5 days and similar for each type of gel. B: Degradation profiles for Y-, X- and T-gels, where X-gels appear most recalcitrant to degradation in 1×PBS over 10 days.
Figure 20B:
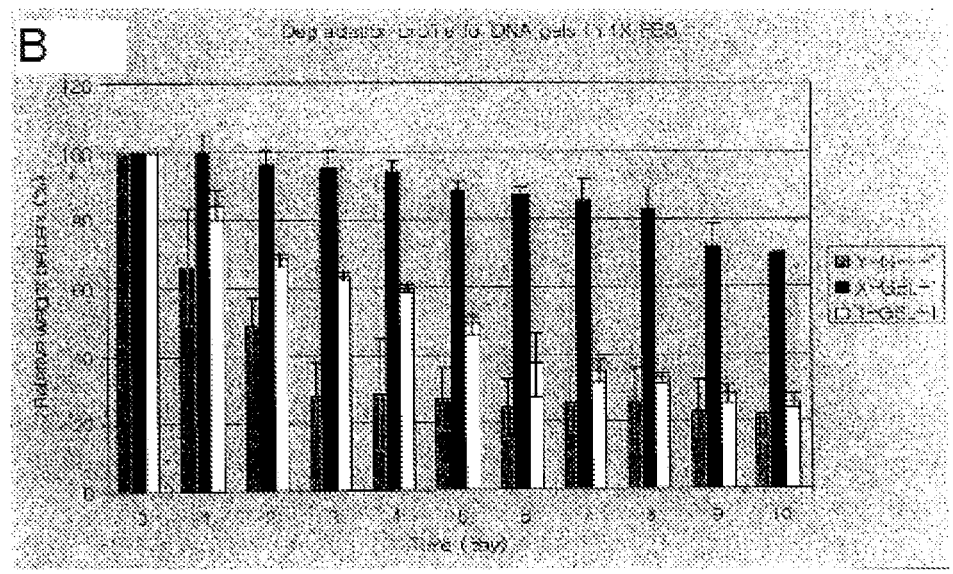
Figure 21A:
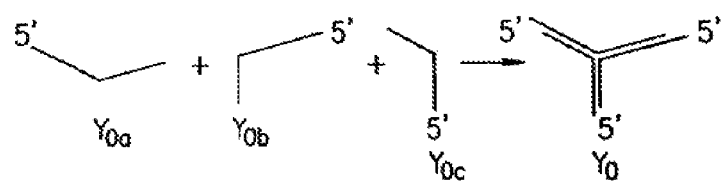
FIG. 21A-21B illustrate steps for formation of Y-shape molecules which are subsequently joined through ligation.
Figure 21B:
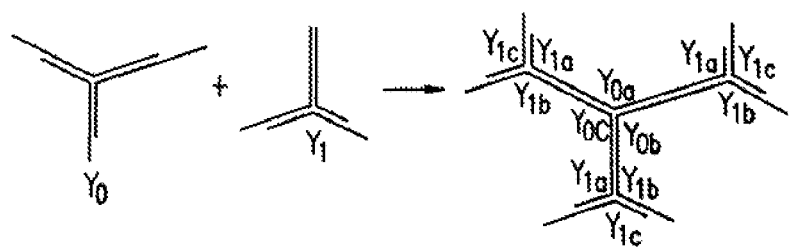
Figure 22A:
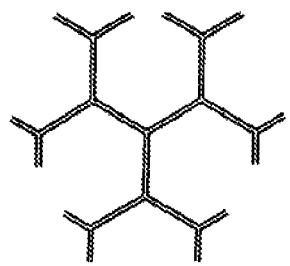
FIG. 22A-B illustrate dendrimer like molecules.
Figure 22B:
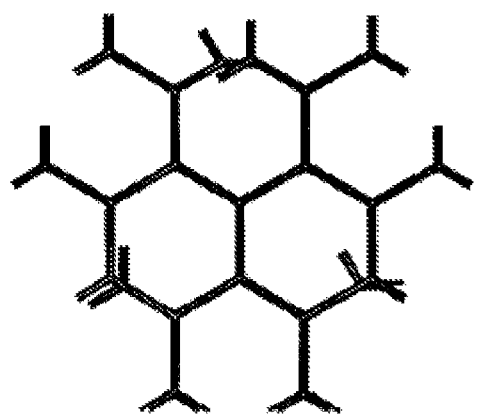
Figure 23:
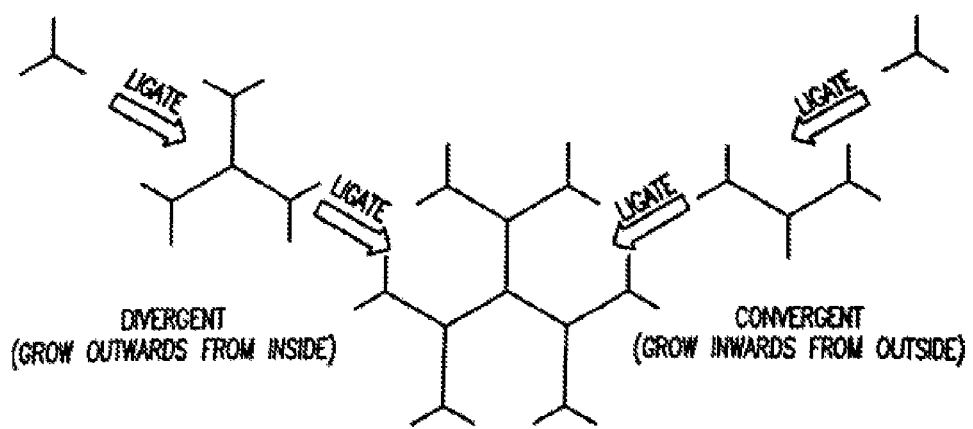
FIG. 23 illustrates divergent versus convergent dendrimer production.
Figure 24:
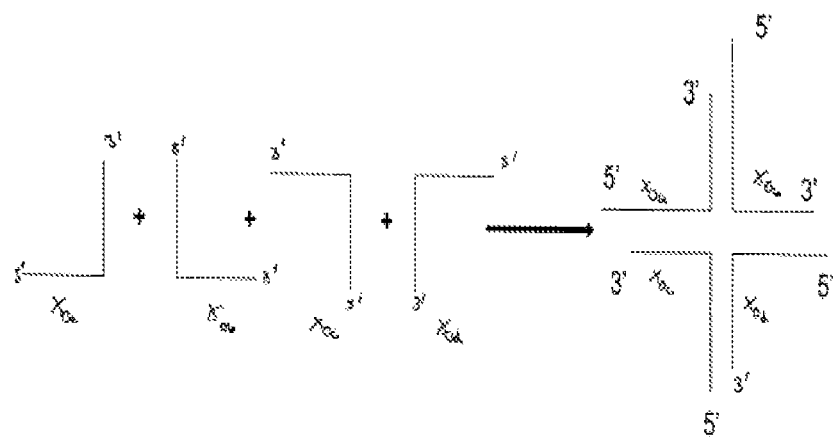
FIG. 24 illustrates formation of an X-shape molecule.
Figure 25:
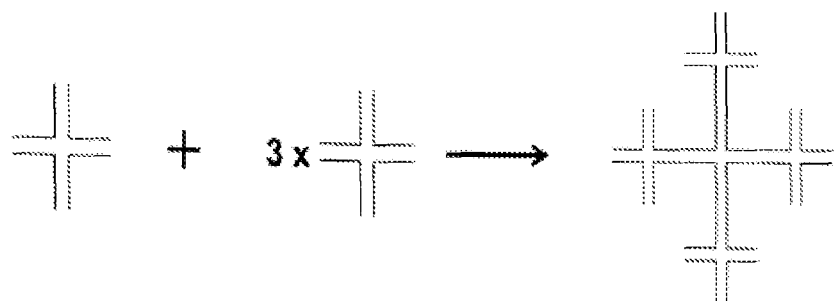
FIG. 25 illustrates joining of several X-shape molecules.
Figure 26:
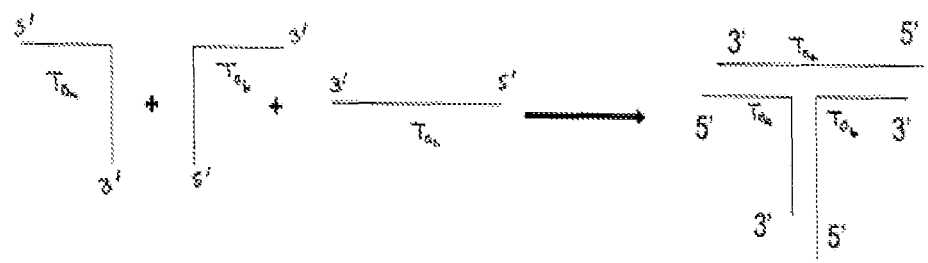
FIG. 26 illustrates formation of a T-shape molecule.
Figure 27:
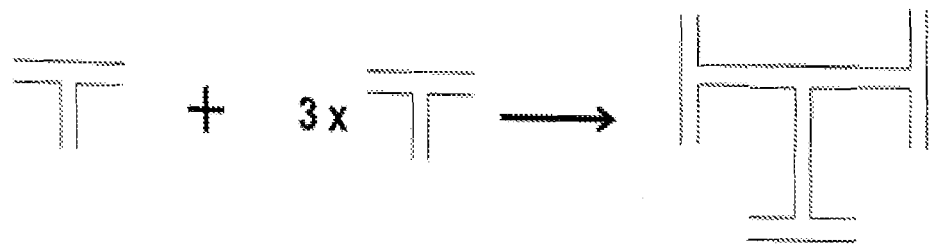
FIG. 27 illustrates formation of several T-shape molecules into a dendrimer-like molecule.
Figure 28:
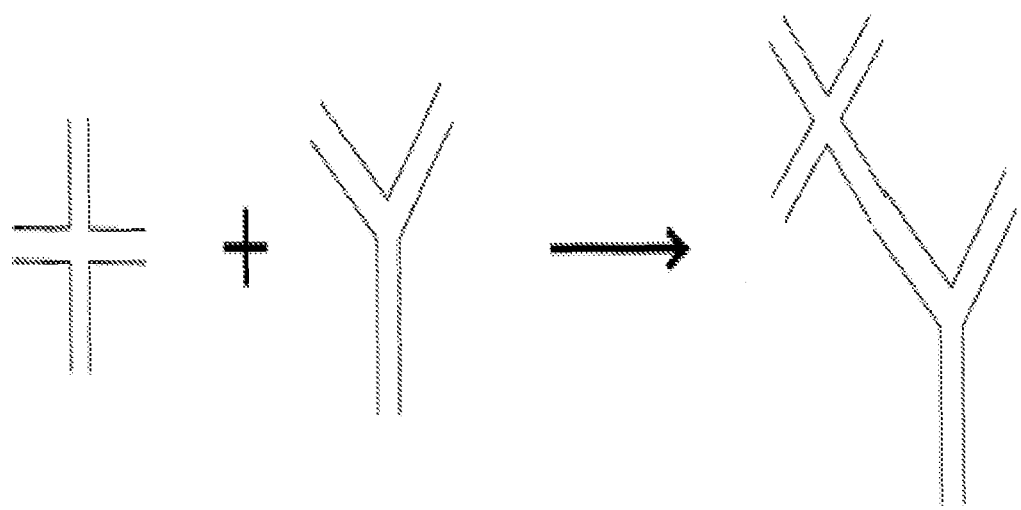
FIG. 28 illustrates formation of matrixes comprised of different shaped molecules.
Figure 29A:
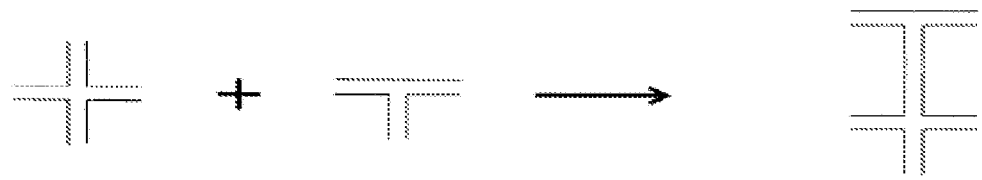
FIG. 29 illustrates further matrixes comprised of different shaped molecules.
Figure 29B:
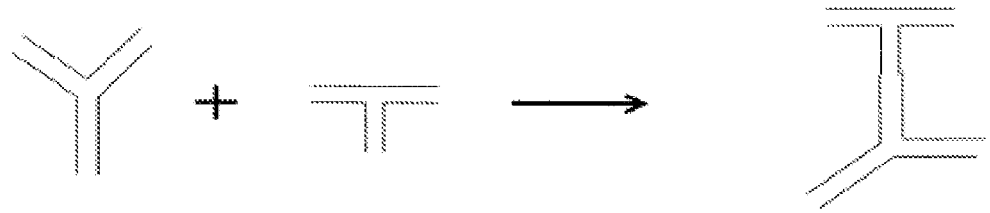
Figure 29C:
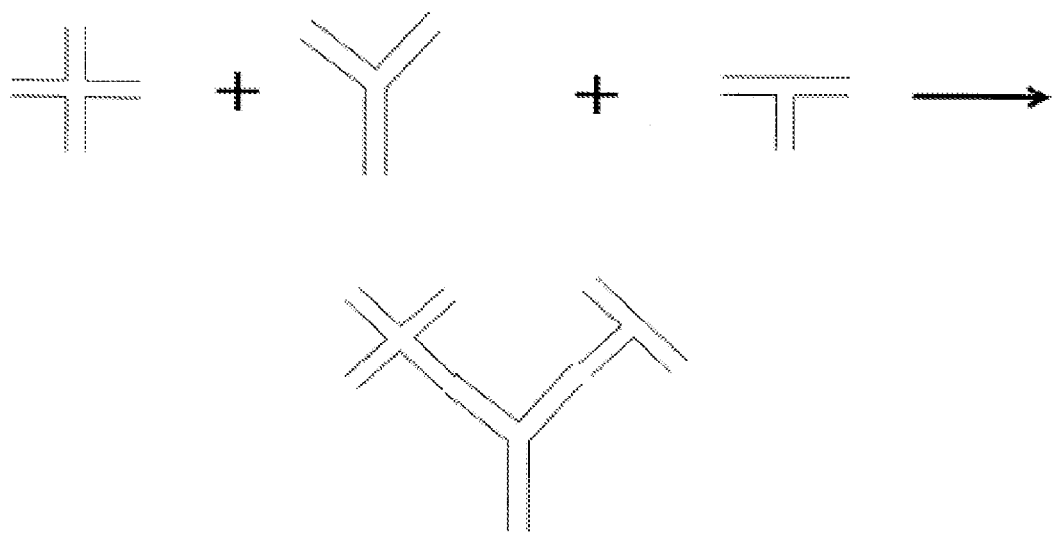
Figures 30A, 30B:
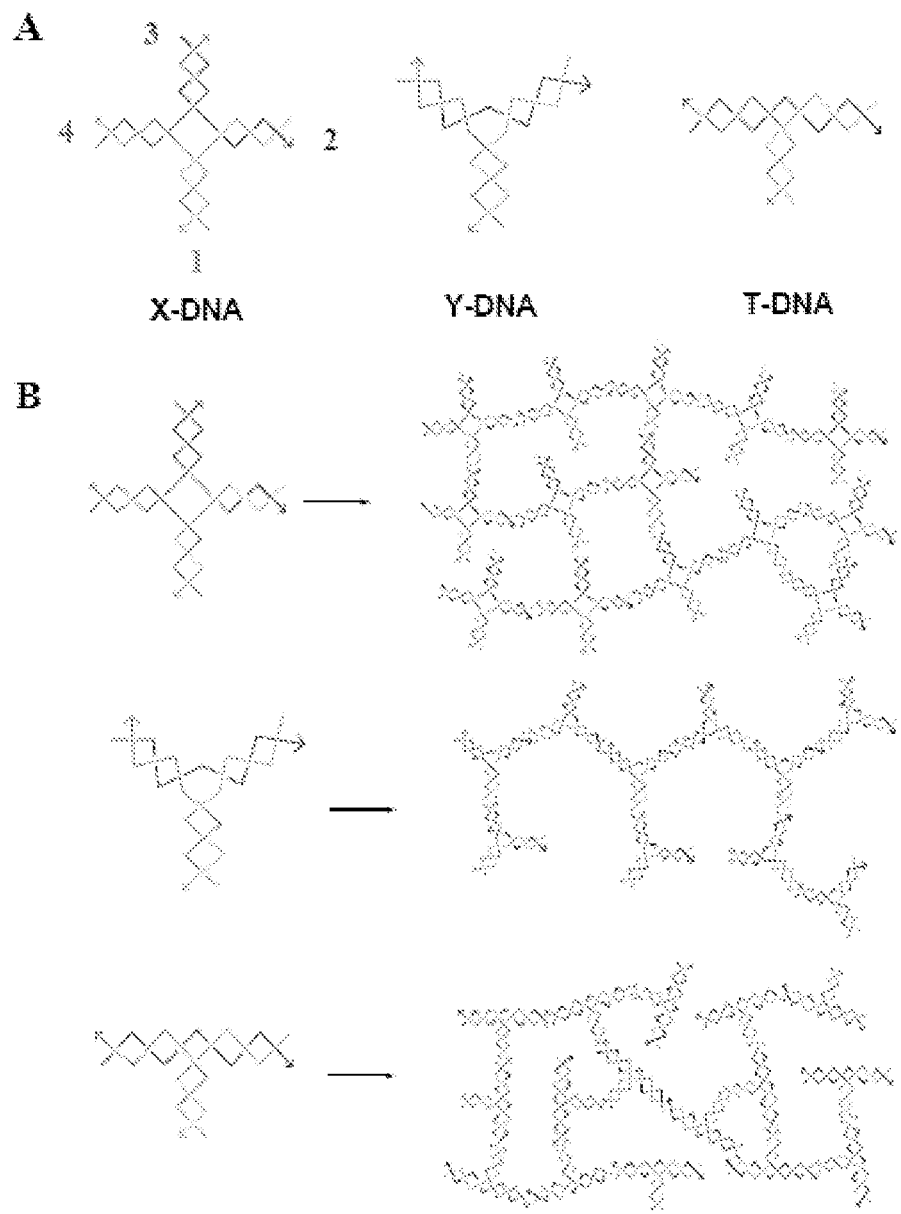
FIG. 30 illustrates A: X-, Y-, T-DNA building blocks B: forming matrixes.

Specific examples of detectable molecules include radioactive isotopes such as $p^{32}$ or $H^3$, fluorophores such as fluorescein isothiocyanate (FITC) FIG. 17, TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, $I^2$-galactosidase, and hapten conjugates such as digoxigenin or dinitrophenyl, etc. Other detectable markers include chemiluminescent and chromogenic molecules, optical or electron density markers, etc. The probes can also be labeled with semiconductor nanocrystals such as quantum dots (i.e., Qdots), described in U.S. Pat. No. 6,207,392. Qdots are commercially available from Quantum Dot Corporation.

Additional examples of reagents which are useful for detection include, but are not limited to, radiolabeled probes, fluorophore-labeled probes, quantum dot-labeled probes, chromophore-labeled probes, enzyme-labeled probes, affinity ligand-labeled probes, electromagnetic spin labeled probes, heavy atom labeled probes, probes labeled with nanoparticle light scattering labels or other nanoparticles or spherical shells, and probes labeled with any other signal generating label known to those of skill in the art. Non-limiting examples of label moieties useful for detection in the invention include, without limitation, suitable enzymes such as horseradish peroxidase, alkaline phosphatase, β-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue™, Texas Red, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6$^{th}$ Edition of the Molecular Probes Handbook by Richard P. Hoagland; a luminescent material such as luminol; light scattering or plasmon resonant materials such as gold or silver particles or quantum dots; or radioactive material include $^{14}C$, $^{123}I$, $^{124}I$, $^{125}I$, $^{131}I$, Tc99m, $^{35}S$ or $^3H$.

Examples of labels include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Genotyping using a microarray can be performed using any of a variety of methods, means and variations thereof for carrying out array-genotyping analysis.

Furthermore, backbone labels are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

In another embodiment, the dendrimer structure is linked to a plurality of biologically active agents as described herein above, and said plurality of biologically active agents include targeting peptides. Thus the dendrimer of the invention is linked to one or more peptides selected from an adenovirus core peptide, a synthetic peptide, an influenza virus HA2 peptide, a simian immunodeficiency virus gp32 peptide, an SV40 T-Ag peptide, a VP22 peptide, a Tat peptide, a Rev peptide, a DNA condensing peptide, DNA protection peptide, endosomal targeting peptide, membrane fusion peptide, nuclear localization signaling peptide, a protein transduction domain peptide or a combination thereof.

In yet another aspect of the invention, the dendrimer is linked to nucleic acid vectors (e.g., plasmid or viral vectors or linear nucleic acid sequences), which are delivered into a cell or subject. Such vectors are known in the art or disclosed herein. Thus in such an embodiment, the dendrimer structures are used in method of effecting transfection or genetic modification of a cell. One central aspect of the dendrimer structures are anisotropic and multivalent.

Protein Production

In some aspects, the nucleic acid matrixes are directed to producing proteins in a cell-free system. Such matrixes simplify protein expression, because virtually all proteins, including toxic proteins or even multiple proteins, can now be expressed easily and efficiently from a protein-producing matrix ("P-gel") without any living organisms/cells. In addition, mutations of any gene can be studied directly at the protein level without transformation and selection. Further, a cell-free system provides an easier route to purifying final protein products. Protein expression efficiency is expected to be inordinately high and the cost to be extremely low due to the reusability of both enzymes and P-gels. The cost of protein production will be further reduced by eliminating the need to feed live cells, maintain reactors, and perform post-expression purifications.

In aspect of the invention, a nucleic acid matrix is a P-gel matrix, which is constructed of two categories of nucleic acid molecules. First, nucleic acids are selected for providing structural support or for forming a networked matrix three-dimensional structure ("building blocks" or "monomers" or "cross-linkers"). In addition, the matrix comprises linear nucleic acids that encode a protein of interest. Of course, the matrix can be designed to provide protein-encoding nucleic acids that encode one or more proteins. Therefore, a particular matrix can encode a single or a plurality of proteins.

In some embodiments, the P-gel matrixes can be comprised entirely of DNA or RNA or a combination of RNA and DNA, which combinations can comprise each type of nucleic acid as a building block or protein-encoding nucleic acid. Various macromolecules necessary for protein expression/translation are known in the art, such as rabbit reticulocyte, wheat germ and bacterial extracts. Supra. As such the matrix can alternatively provide DNA, RNA or a combination of both, whereby the appropriate macromolecules are selected to provide either "coupled" transcription (of DNA) followed by translation into protein, or translation (of RNA) into protein.

Furthermore, by designing matrixes or P-gels with varying concentrations of building block nucleic acids, protein expressing nucleic acids, as well as different ratios of RNA to DNA encoding a protein, various ranges for protein production are obtained.

In one embodiment, the building block monomer nucleic acids comprise X-shaped nucleic acid that provide a networked matrix, which network also comprises linear nucleic acids that encode at least one or more desired protein. In addition, the building blocks can comprise X-, Y-, dumbell-, T-, dendrimer-shapes or a combination thereof. Furthermore, the P-gel can be constructed of X- and Y-shape nucleic acids in a predetermined ratio to provide a particular P-gel geometry, whereby linear nucleic acids are also integrated into the resulting network matrix. In yet another embodiment, said building block monomers are DNA, or PNA. In addition, the linear nucleic acid is DNA, RNA, TNA, PNA or a combination thereof (including any two thereof).

In yet another embodiment, the P-gel is comprised entirely of DNA. In a further embodiment, a P-gel monomer has a molecular weight selected from about 50 kDa to about 500 MDa. In various embodiments, the molecular weight is 50, 60, 70, 80, 90, 100, 200, 300, 400, 500, 600, 800, 900, 1000 kDa. In other embodiments, the molecular weight is 1, 5, 10, 50, 100, 150, 200, 250, 300, 350, 400, 450, 500 or 550 MDa. In one preferred embodiment, a P-gel is a hydrogel.

In addition, the P-gel is hydradable whereby the dry form swells in volume (e.g., by addition of water) by about 100, 200, 300, 400, 500, 600, 700, 800, 900, 1000, 1100, 1200, 1300, 1400, or 1500%.

Furthermore, the P-gel is comprised by nucleic acids having tensile strength selected that is about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65%.

One aspect of the invention is directed to a nucleic acid matrix is comprises of nucleic acid molecules, branched and linear, and produces proteins in a cell-free environment. In one embodiment, the matrix forms a gel and is comprised entirely from DNA (linear genes as monomers and branched, X-shape DNA as crosslinkers). Proteins are produced directly from the gel via in vitro transcription coupled with translation (TNT). Post-expression purification is no longer a challenge since the system is cell-free and since the major components are expressed proteins. Also, both the gels and the TNT enzymes can be recycled and reused many times, further reducing costs. Maintenance of cells is no longer needed either. In one embodiment, the gel is hydrogel thus hydradable with water.

In another embodiment, the protein yield for the matrix is 7.9 mg from 1 cm$^3$. In other embodiments, the yield is about 3, 4, 5, 6, 7, 8, 9, 10, 11, 12, 13, 14, 15, 16, 17, 18, 19, 20, 21, 22, 23, 24 or 25 mg from 1 cm$^3$ of the gel.

Furthermore, in one embodiment, the cross-linker nucleic acid is DNA and further is X-DNA. In some embodiments, an X-DNA is about 8, 9, 10, 11, 12, 13, 14, 15, 16, 17, 18, 19, 20, 21, 22, 23, 24, 25, 26, 27, 28, 29, or 30 nm in length. In yet a further embodiment an X-DNA is about 10 to 20 nm in length. A further embodiment is directed to an X-DNA that is 14 nm in length.

In yet another aspect, the gel is molded into a matrix forming a hollow structure with one closed end and one open end, or two closed ends, wherein the structure provides surface area internally and externally from which proteins can be transcribed. The concentration of genes a network format such as in a nucleic acid hydrogel provide higher concentrations of genes that kinetically increase the rate of transcription. In addition, the networked scaffolds of nucleic acids provide anchoring sites for more enzymatic activities and turnovers. Moreover, the hollow tube structure provides a concentrated solution of the necessary macromolecules necessary for translation or transcription-coupled translation thus enhancing expression yields for a particular gel or gels substantially.

In one embodiment, the hollow "close ended" networked matrix enhances the protein yield 1, 2, 3, 4, 5, 6, 7, 8, 9, or 10 fold as compared to an open matrix.

In various embodiments of the protein yielding matrixes or P-gels comprise nucleic acid building blocks that are DNA, RNA, PNA, TNA or a combination thereof. In one embodiment, the nucleic acid is entirely DNA, entirely RNA or a combination of RNA and DNA. In a further embodiment, the cross-linker DNA is selected from branched nucleic acids that are X-, Y-, T-, dumbbell- or dendrimer-shape and the protein-encoding nucleic acid is linear or circular.

In another aspect of the invention, the matrix constructed of nucleic acids of the present invention is further linked to at least one (or more) copolymer or additional compound, which are known in the art or described herein above. The nucleic acid molecules are capable of undergoing various enzymatic reactions, including DNA polymerase, RNA reverse transcriptase, terminal transferase, DNA ligase, RNA ligase, exonuclease, ribonuclease, endonuclease, polynucleotide kinase, DNA methylase, and DNA ubiquitinase. Therefore, the nucleic acid molecules can be readily modified or linked to said copolymer(s) or additional compound(s).

In some embodiments, the protein yielding matrixes yield protein at a rate of 10, 15, 20, 25, 30, 35, 40, 45 ng protein per 1 ng DNA or 1 ng RNA.

Post-Translational Modifications

A yet another aspect of the invention is directed to nucleic-acid based protein-yielding matrixes where the resulting protein is post-translationally modified. Reviewing the glycosylation process of proteins in cells, glycosylation in most eukaryotes occurs commonly in the ER, i.e., yeast, insect, plant and mammalian cells share the features of N-linked oligosaccharide processing in the ER. Though the resultant glycoproteins in the ER have a near identical carbohydrate structure, with only the initial glycosylation in the ER, glycoproteins with a therapeutic efficacy cannot be fully produced. Therefore, in various embodiments a hydrogel can comprise the macromolecules necessary for post-translational modification of proteins produced in the cell-free protein synthesis system of the invention.

In certain embodiments a protein-expressing matrix (e.g., hydrogel) comprises one or more enzymes that modify one or more proteins expressed in or from the matrix, which modifications include but are not limited to phosphorylation, glycosylation, methylation, ubiquitination, biotinylation, alkylation, acetylation, glutamylation, glycylation, isoprenylation, lipoylation, phosphoantetheinylation, sulfation, citrullination, deamidation or isomerization.

The production of premature glycoprotein, which does not undergo the complete post-translational modification, may be caused by the deficiency of the terminal glycosylation machinery such as the Golgi apparatus. In other words, oligosaccharide processing by different cell types may diverge in the Golgi apparatus. The initial step in O-glycosylation by mammalian cells is the covalent attachment of N-acetylgalactosamine to serine or threonine. No O-glycosylation sequence has been identified analogous to the Asn-X-Ser/Thr template required for N-glycosylation. In further contrast to N-glycosylation, no preformed, lipid-coupled oligosaccharide precursor is involved in the initiation of mammalian O-glycosylation. Sugar nucleotides serve as the substrates for the first and all subsequent steps in O-linked processing. Following the covalent attachment of N-acetylgalactosamine to serine or threonine, several different processing pathways are possible for mammalian O-linked oligosaccharides in the Golgi. The oligosaccharide structures of glycoproteins can have a profound effect on properties critical to the human therapeutic use, including plasma clearance rate, antigenicity, immunogenicity, specific activity, solubility, resistance to thermal inactivation, and resistance to protease attack. Therefore, for a cell-free protein synthesis to be applied to the large-scale production of glycoprotein and for a rapid insight into the role of protein glycosylation to understand the relationship among stability, conformation, function of protein and glycosylation, an efficient cell-free completely post-translationally modified protein synthesis system in which protein is completely post-translationally modified can be implemented utilizing the protein-yielding matrixes described herein.

For the production of proteins having the complete and correct structure, the present invention includes the combination of a cell-free protein synthesis system and co- and post-translational modification machinery containing organelles, separated from cells, relevant to co- and post-translational modification. This cell-free completely post-translationally modified protein synthesis method is a new approach that has not been attempted by anyone. This method is suitable especially to large-scale production of efficacious and useful proteins. Additionally, this method can be applied directly to post-translational modification processes, required to produce a biologically active protein besides glycosylation.

As mentioned above, since the addition of only the ER cannot produce the completely post-translationally modified proteins, the addition of co- and post-translational modification machinery involved in terminal glycosylation is necessary. The addition of co- and post-translational modification machinery containing signal recognition particle, ER, Golgi apparatus, plasma membrane, and the like to the cell-free protein synthesis reaction mixture stimulates the production of completely post-translationally modified protein. A complete incubation mixture (containing the components of cell-free protein synthesis and co- and post-translational modification machinery) gives the completely post-translationally modified proteins. The events of the co- and post-translational modification process can be faithfully reproduced in vitro.

Cell sources for the preparation of the extract or lysate for the cell-free protein synthesis system and those for the co- and post-translational modification machinery may be the same or different. In the case of using the same cell, the extract or lysate for the cell-free protein synthesis system and the co- and post-translational modification machinery may be prepared separately or together. Examples for methods of preparing such extracts are known in the art, as described in U.S. Pat. No. 6,780,607, which is incorporated by reference herein in its entirety.

The co- and post-translational modification machinery may be prepared from tissues and cultured cell lines. In glycosylation it is favorable to genetically engineer a cell source for the enhancement of the expression level of glycosylation related enzymes and/or for the enrichment of the pool of sugar nucleotides which serve as sugar donors in glycosylation. This type of genetic manipulation can be carried out by those skilled in the art; therefore, the detailed explanation is omitted in this specification.

As an example for obtaining the cell extract in the cell-free protein synthesis method, the preparation of nuclease-treated RRL and a crude homogenate from Chinese hamster ovary (CHO) cells, as well as the preparations of ER containing signal recognition particle, Golgi apparatus, and plasma membrane from a crude homogenate are described in detail in U.S. Pat. No. 6,780,607. Of course, such extracts can be obtained from any available mammalian cell(s).

A glycoprotein produced by the cell-free protein synthesis utilizing one or more matrixes of the invention, may be further modified through carbohydrate-adding reaction and/or carbohydrate-deleting reaction and/or carbohydrate-substituting reaction with enzymes relevant to the modification of side chains, e.g., glycosyltransferase, glycosidase, transglycosidase and so on. As such the addition, deletion, or substitution of carbohydrate side chains is effected. Furthermore, in another embodiment, one or more protein-yielding matrixes, in conjunction with the necessary macromolecules, can produce proteins with carbohydrate side chains not known in the general glycoprotein structures or produce novel glycoprotein structures synthesized artificially, and thus resulting in development of new glycoproteins. For example, in the carbohydrate-adding reaction resultant itself or the erythropoietin (EPO) separated from it, sialic acid is further attached to the terminal chain thereof by transglycosidase which is one of carbohydrate chain addition enzymes, and the efficacy of glycoprotein increases with the addition of sialic acid to the terminal chain thereof.

Therefore, in some embodiments, the protein-yielding matrixes can be applied to the production of proteins of therapeutic, commercial or research value. This includes proteins such as growth hormones, granulocyte colony stimulating factor, interleukin, interferon, thrombopoietin, tissue plasminogen activator and humanized monoclonal antibody. Additionally, in certain embodiments, kits are provided comprising nucleic acid matrixes for protein production of completely post-translationally modified protein as well as the necessary extracts discussed above that are necessary for post-translational modification thus enabling a research tool in the form of a co- and post-translational modification analyze protein functionality.

Recyclability

In other aspects of the invention, the protein yielding matrixes can be re-used at least 3 times and can last 7 days before the gel micropads are degraded by nucleases (from lysates). However, by linking the nucleic acid based matrices of the invention with at least one copolymer or at least one additional compound, matrices are constructed that are mechanically stronger gels. In one embodiment, doping with gold nanoparticles (AuNP) is utilized to make stronger gels, where gold is attached either onto the DNA strands by direct crosslinking AuNP with DNA or between DNA strands by suspending AuNP in the gel. FIG. 10 shows a schematic drawing of crosslinking AuNP onto DNA, representing a gel that was constructed. In addition, nuclease activity can be significantly reduced by adding compounds known in the art (such as DNase, Exo Nuclease III, etc.), or achieved by either conventional protein fractions or by passing through Ab-affinity columns to further purify extracts utilized for in vitro protein expression.

In another aspect of the invention, the nucleic acid matrices can be further stabilized against degradation by modifications of the nucleic acid backbone. Such modifications are described herein or known in the art, such as those disclosed in U.S. Patent Publication Nos. 2005/32068, 2004/161844, 2001/49436, and U.S. Pat. Nos. 5,610,289; 5,965,721; 6,201,103 (teaching Peptide Nucleic Acid comprising modified backbone), or U.S. Pat. No. 6,025,482, the disclosure of each of which is incorporated herein by reference.

In yet another aspect, the matrix is further stabilized by linking nucleic acids of the matrix to a copolymer, which are known in the art or described herein above. In one embodiment, a branched DNA-polystyrene hybrid molecule is constructed. Therefore, some embodiments, a particular gel A P-gel is constructed either entirely from a DNA-copolymer hybrid molecule or from a mixture of X-DNA and DNA-polystyrene. Thereby, providing a hybrid DNA P-gel whose backbone consists of a nuclease-resistant polystyrene group. Additional copolymers that can be linked to nucleic acids are disclosed. Supra.

As such, the matrices are significantly strengthened and become amenable to recycling. Thus, in one embodiment the protein yielding matrices can be re-used 1, 2, 3, 4, 5, 6, 7, 8, 9, 10, 11, 12, 13, 14, or 15 times.

Delivery of Biologically Active Agents

Another central aspect is directed to a matrix composed of nucleic acids described herein, so as to provide a structure for delivery of one or more biologically active agents. In one embodiment, the matrix can deliver cells, along with one or more biologically active agents. In another embodiment, the matrix can provide a scaffold for three-dimensional cell growth or tissue regeneration, either in vitro or in vivo. In yet another embodiment, the matrix providing a platform for cell growth or tissue generation concomitantly delivers one or more biologically active agents contained therein and released therefrom.

In one embodiment, the matrix is comprised of branched nucleic acids that are DNA. In another embodiment, the DNA is X-shape, Y-shape, T-shape, dumbbell-shape or dendrimer shape, or a combination thereof. In yet another embodiment, matrix comprises branched DNA and linear DNA or RNA. In yet another embodiment, the matrix comprises branched nucleic acids that include DNA and RNA. In yet a further embodiment, the matrix can comprise at least one copolymer known in the art or disclosed herein above. As such, the copolymer is linked to one or more building block nucleic acids of the matrix. Additional embodiments are directed to linking components or chemical moieties to the matrix, by cross-linking such additional components to the nucleic acids or copolymers of the matrix. Additional components in this context have been disclosed herein, and include small molecules, nanoparticles, nanofilaments, metals, or peptides. In one embodiment, the additional component is a nanoparticle that is a metal, more preferably, gold, silver or copper.

Examples of biologically active agents that can be incorporated into a matrix(es) include but are not limited to bioactive agents delivered alone or in combination with another compound and/or cell. Nonlimiting examples of bioactive agents include interferon, interleukin, erythropoietin, granulocyte-colony stimulating factor (GCSF), stem cell factor (SCI:), leptin (OB protein), interferon (alpha, beta, gamma), ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone morphogenetic protein 2 (BMP2), BRAK, C-10, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, antimicrobials amoxicillin, ampicillin, cephalosporins, erythromycin, tetracyclines, penicillins, trimethprim-sulfamethoxazole, quinolones, amoxicillin, clavulanatf, azithromycin, clarithromycin, anti-cancer drugs aliteretinoin, altertamine, anastrozole, azathioprine, bicalutamide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, anti-virus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetylsalicylic acid, acetaminophen, analgesic, anti-tumor preparation, anti-cancer preparation, anti-proliferative preparation or pro-apoptotic preparation.

In some aspects the matrixes of the present invention encapsulate a vector exclusively, or along with cells and/or other biologically active agents disclosed herein. Examples of vectors include adenoviral vectors, adenoviral associated vectors, retroviral vectors, and/or plasmid vectors.

In other aspects of the invention the nucleic acid vectors are deposited in the matrix of the invention and are delivered to a target cell or tissue. In other aspects, such vectors can encode a therapeutic protein or antisense mRNA. In yet other aspects of the invention, one or more vectors each encoding a different therapeutic capable agent delivered to cells or tissue via the device of the invention. Therefore, the device of the invention will controllably release vectors to effectuate gene delivery, such as in gene therapy. Gene delivery may be either endogenously or exogenously controlled. Examples of endogenous control include promoters which are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

In an alternative aspect of the invention, the device can deliver the small molecule drug, such as those in the preceding paragraph, where the device is utilized to deliver the vector and the inducible agent (e.g., small molecule drug), the vector alone or some combination thereof.

Vectors include derivatives of SV-40, adenovirus, retrovirus-derived DNA sequences and shuttle vectors derived from combinations of functional mammalian vectors and functional plasmids and phage DNA. Eukaryotic expression vectors are well known, e.g. such as those described by P J Southern and P Berg, J Mol Appl Genet 1:327-341 (1982); Subramini et al., Mol. Cell. Biol. 1:854-864 (1981), Kaufmann and Sharp, J. Mol. Biol. 159:601-621 (1982); Scahill et al., PNAS USA 80:4654-4659 (1983) and Urlaub and Chasin PNAS USA 77:4216-4220 (1980), which are hereby incorporated by reference. The vector used in one or methods disclosed herein may be a viral vector, preferably a retroviral vector. Replication deficient adenoviruses are preferred. For example, a "single gene vector" in which the structural genes of a retrovirus are replaced by a single gene of interest, under the control of the viral regulatory sequences contained in the long terminal repeat, may be used, e.g. Moloney murine leukemia virus (MoMuIV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, BioTechniques 6(7):608-614 (1988), which is hereby incorporated by reference.

Recombinant retroviral vectors into which multiple genes may be introduced may also be used with the matrixes or methods of the invention. As described by Eglitis and Andersen, above, vectors with internal promoters containing a cDNA under the regulation of an independent promoter, e.g. SAX vector derived from N2 vector with a selectable marker (noe.sup.R) into which the cDNA for human adenosine deaminase (hADA) has been inserted with its own regulatory sequences, the early promoter from SV40 virus (SV40) may be designed and used in accordance with methods disclosed herein or as known in the art.

In some aspects of the invention, the vectors comprising recombinant nucleic acid molecules are first introduced (e.g., transfected) into cells, which cells are deposited in the matrixes of the invention. For example, the vectors comprising the recombinant nucleic acid molecule are incorporated, i.e. infected, into the BM-MNCs by plating ~5e5 BM-MNCs over vector-producing cells for 18-24 hours, as described by Eglitis and Andersen BioTechniques 6(7):608-614 (1988), which is hereby incorporated by reference, and subsequently said cells are deposited into the reservoir portion of the device.

In some aspects of the invention the nucleic acid molecule encodes proteins such as growth factors, including but not limited to, VEGF-A, VEGF-C PlGF, KDR, EGF, HGF, FGF, angiopoietin-1, and cytokines. In additional preferred embodiments, the nucleic acid molecule encodes endothelial nitric oxide synthases eNOS and iNOS, G-CSF, GM-CSF, VEGF, aFGF, SCF (c-kit ligand), bFGF, TNF, heme oxygenase, AKT (serine-threonine kinase), HIF.alpha. (hypoxia inducible factor), Del-1 (developmental embryonic locus-1), NOS (nitric oxide synthase), BMP's (bone morphogenic proteins), SERCA2a (sarcoplasmic reticulum calcium ATPase), .beta.sub.2-adrenergic receptor, SDF-1, MCP-1, other chemokines, interleukins and combinations thereof.

In additional aspects of the invention, the matrixes of the invention comprise genes which may be delivered in the autologous BM-MNCs using one or more methods disclosed herein include but are not limited to nucleic acid molecules encoding factor VIII/von Willebrand, factor IX and insulin, NO creating genes such as eNOS and iNOS, plaque fighting genes thrombus deterrent genes, for example. Therefore, in such an example, the matrix of the invention contains cells that secrete the therapeutic agent from the pores of the matrix, wherefrom the therapeutic agent exits from the matrix into the surrounding cells (e.g., in vitro or in vivo). It will be appreciated that the preceding growth factors can also be delivered in the form of synthesized or recombinant proteins.

In mammalian host cells, a number of viral-based expression systems can be utilized. In cases where an adenovirus is used as an expression vector, the nucleotide sequence of interest (e.g., encoding a therapeutic capable agent) can be ligated to an adenovirus transcription or translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the AQP1 gene product in infected hosts. (See e.g., Logan & Shenk, Proc. Natl. Acad. Sci. USA 8 1:3655-3659 (1984)).

Specific initiation signals can also be required for efficient translation of inserted therapeutic nucleotide sequences. These signals include the ATG initiation codon and adjacent sequences. In cases where an entire therapeutic gene or cDNA, including its own initiation codon and adjacent sequences, is inserted into the appropriate expression vector, no additional translational control signals can be needed. However, in cases where only a portion of the therapeutic coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See e.g., Bittner et al., Methods in Enzymol, 153:516-544 (1987)).

Cell and Tissue Culture

Although the preceding description relates to therapeutic applications, the invention is also applicable to non-therapeutic applications such as cell culturing and tissue engineering, by providing a three-dimensional scaffold and/or delivery of biologically active agents (e.g., cell growth factors, angiogenic factors. Thus agents that can be controllably released by embodiments of the invention include therapeutic agents, cell culture agents and tissue engineering agents.

As such one aspect of the invention is directed to matrixes or methods, where the matrix is utilized to encapsulate a cell. In one embodiment, the matrix can be utilized to propagate and culture cells in vitro. Further, in vitro applications include tissue generation or regeneration, by utilizing the matrix either as a structural scaffold or as both a scaffold and source of growth promoting factors. In another embodiment, the matrix is implanted into a target site in a subject. The term "implanted" is used to mean any means of delivery known in the art and is not necessarily limited to invasive procedures (e.g., topical, or skin-based applications).

In one embodiment, the matrix is utilized in a cell culture to release a particular agent in a controlled manner to monitor the effects of such an agent on cells or tissue cultures. For example, the device of the invention can be utilized in a method of screening different agents to determine the mechanisms, by which such compounds induce cell differentiation, e.g., such as in studying effects on stem cells. Methods of utilizing cell and tissue culture are known in the art, such as disclosed in U.S. Pat. No. 7,008,634 (using cell growth substrates with tethered cell growth effector molecules); U.S. Pat. No. 6,972,195 (culturing potentially regenerative cells and functional tissue organs in vitro); U.S. Pat. No. 6,982,168 or 6,962,980 (using cell culture to assay compounds for treating cancer); U.S. Pat. No. 6,902,881 (culturing techniques to identify substances that mediate cell differentiation); U.S. Pat. No. 6,855,504 (culturing techniques for toxicology screening); or U.S. Pat. No. 6,846,625 (identifying validated target drug development using cell culture techniques), the disclosure of each of which is herein incorporated by reference. The matrixes of the invention are readily adaptable to such cell culturing techniques as would be evident to one of ordinary skill in the art.

In some aspects of the invention, the matrix encapsulates cells and a biologically active agent, whereby the matrix provides a three-dimensional scaffold on which cells grow/differentiate, either in vitro or in vivo. Furthermore, the matrix nucleic acids can be linked to additional copolymers to provide a substrate surface defining a tissue contacting surface, whereby the surface is disposed with polypeptides or peptides which are cell/tissue growth potentiating. The matrix can release biologically active agents that are also cell/tissue growth potentiating, where such polypeptides/peptides include PDGF, EGF, FGF, TGF, NGF, CNTF, GDNF, VEGF and type I collagen peptides, or functionally active fragments and/or combinations thereof.

The nucleic acid matrixes or matrixes either without or further linked with additional polymers may be used for a variety of tissue engineering applications including, inter alia, to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part.

In some embodiments, the matrixes may also more specifically be used as sutures, scaffolds and wound dressings. The type of nucleic acid polymer or copolymer used may affect the resulting chemical and physical structure of the polymeric biomaterial.

In an another embodiment, a matrix is placed in the or on a wound area, whereby the matrix controllably releases a desired therapeutic agent that promotes wound healing, exclusive of or in addition to providing a scaffold for cell regrowth/regeneration necessary for improved or faster healing. For example, the therapeutic agent can comprise cell growth or angiogenic factors, described herein, as one of several potential agents.

Target Sites for Delivery or Implantation

It will be appreciated that the matrixes of the invention can be implanted using methods known in the art, including invasive, surgical, minimally invasive and non-surgical procedures. Depending on the subject, target sites, and agent(s) to be delivered the microfabrication techniques disclosed herein, can be adapted to make the delivery scaffold of the invention of appropriate size and shape. The matrix described herein is suitable for use in various locations in the body. For example, they can be implanted on the surface of the skin, under the skin, or in or near internal tissues or organs. The devices in some embodiments are located in or near a gastrointestinal tract, airway tissue or organ, cardiovascular tissue or organ, or neuronal tissue or organ. Other examples of target sites for implantation include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in an animal.

In certain embodiments, the gels, or scaffolds of the invention can be encased in a nonbiodegradable material, which materials are known in the art. For example, if a matrix structure of the invention is attached to a temporary implant, the matrix can be encased in a nonbiodegradable casing. Suitable materials for casings include but are not limited to poly(dimethylsiloxane), silicone elastomers, polyurethane, poly(tetrafluoroethylene), polyethylene, polysulfone, poly(methyl methacrylate), poly(2-hydroxyethyl methacrylate), polyacrylonitrile, polyamides, polypropylene, poly(vinyl chloride), poly(ethylene-co-(vinyl acetate)), polystyrene, poly(vinyl pyrrolidine), yellow wax, petrolatum cholesterol, stearyl alcohol, white wax, white petrolatum, methylparaben, propylparaben, sodium lauryl sulfate, propylene glycol, glycerogelatins, geling agents such as carbomer 934, cellulose derivatives, natural gums, penetration enhancers such as dimethyl sulfoxide, ethanol propylen glycol, glycerin, urea, glycerogelatins, coloring agents, lactose, stearic acid, starch glycolate, sugar, gelatin, fixed vegetable oils and fats, glycerin, propylene glycol, alcohol, ethyl oleate, isopropyl myristate, dimethyl acetamide, and mixtures or aqueous or oil based dispersions of these.

Selection of implantation sites for the matrixes (gels or scaffolds) are within the skill of one of skill in the art. For example, suitable sites for implantation in the eye include the anterior chamber, posterior chamber, vitreous cavity, suprachoroidal space, subconjunctiva, episcleral, intracorneal, epicorneal and sclera. Suitable sites extrinsic to the vitreous comprise the suprachoroidal space, the pars plana and the like. The suprachoroid is a potential space lying between the inner scleral wall and the apposing choroid. Matrixes implanted in a suprachoroid may deliver drugs to the choroid and to the anatomically apposed retina, depending upon the diffusion of the drug from the implant, the concentration of drug comprised in the implant and the like. Additional methods and procedures for implanting a device of the invention in various tissue/organ sites are known in the art, such as disclosed in U.S. Pat. No. 7,013,177; 7,008,667; 7,006,870; 6,965,798; 6,963,771; 6,585,763; 6,572,605; or 6,419,709, the disclosure of each of which is herein incorporated by reference.

In another embodiment the matrix provides a means for topical delivery, such as to skin. For example, the matrix or gel can be encased in a nondegradable casing (e.g., plastics or bandage or patch) providing an aperature or surface for contacting the target site (i.e., skin). Subsequently, the gel can release in a time controlled manner the desired drug to the target site.

One aspect of the invention is directed to utilization of the matrixes or scaffolds of the invention in wound healing. In general, the body is able to regenerate injured tissue to produce new tissue having properties similar to the original tissue. For example, small cuts heal without forming permanent scars, and clean fractures in bone are healed by the formation of new bone that binds the two fragments of bone together. However, connective tissue cells and other organ cells are anchorage dependent—they require a scaffold to exhibit normal physiological behavior. Where tissue damage is extensive or large gaps are present, cells migrating into the wound may not find proper anchorage and may produce scar tissue to bridge the gap between healthy tissue at the edges of the wound. Scar tissue does not have the same mechanical and biological properties as the original tissue. For example, scar tissue in skin is not as pliable as the original tissue. Scar tissue in bone is not as strong as uninjured bone and often provides a weak point where it is easier to break the bone again. Some tissues, such as articular cartilage, do not naturally regenerate, and healing only proceeds by the formation of scar tissue. In another embodiment, the matrix provides a scaffold for wound healing (e.g., burns, cuts, deep tissue trauma), which scaffold can be encased in a nondegradable or degradable casing, or applied without any such casing, to a selected target site. The scaffold can concomitantly release a desired drug compound while also providing a scaffold/support for cell growth and tissue (e.g., skin) regeneration.

Drugs of Use in the Invention

The methods and compositions of the invention include the study and use of drugs, e.g., insulin sensitizers, and include performing association studies for determining genotypic and/or phenotypic traits associated with responsiveness to drugs, e.g., insulin sensitizers, screening individuals for predisposition to response to drugs, e.g., insulin sensitizers, e.g., adverse response, and/or administering or not administering drugs, e.g., insulin sensitizers to the individual based on such screening. This section describes certain drugs of use in embodiments of the invention. Further useful drugs for the invention are described in section IVC, Association studies and methods for classes of drugs.

Insulin Sensitizers

One class of drugs included in certain embodiments of the invention is an insulin sensitizer. The term "insulin sensitizer," or "insulin sensitizing agent," as used herein, refers to any agent capable of enhancing either secretion of or, more typically, tissue sensitivity to, insulin. Non-exclusive examples of insulin sensitizers include metformin, sulfonylureas, alpha glucosidase inhibitors and PPAR modulators, including thiazolidinediones. Further examples of insulin sensitizers are described below.

The thiazolidinediones are examples of PPAR modulators, which are one class of insulin sensitizers. The term "PPAR modulator," as used herein, refers to peroxisome proliferator-activated receptor agonists, partial agonists, and antagonists. The modulator may, selectively or preferentially, affect PPAR alpha, PPAR gamma, or both receptors. Typically, the modulator increases insulin sensitivity. According to one aspect, the modulator is a PPAR gamma agonist. One PPAR gamma agonist used in embodiments of the invention is 5-[{6-(2-fluorobenzyl)oxy-2-naphthyl}methyl]-2,4-thiazolidinedione; (MCC-555 or "netoglitazone").

Insulin Sensitizers—PPAR Modulators

One class of insulin sensitizers of the invention is PPAR modulators, and in particular PPAR-gamma modulators, e.g., PPAR-gamma agonists. PPAR modulators include the PPAR-alpha, PPAR-delta (also called PPAR-beta), and PPAR-gamma agonists. Especially useful are the thiazolidinediones (TZDs), which were developed in the 70's and 80s by screening newly synthesized compounds for their ability to lower blood glucose in diabetic rodents. Three molecules from this class, troglitazone, rosiglitazone, and pioglitazone, were ultimately approved for the treatment of patients with Type II diabetes. Although these compounds were developed without an understanding of their molecular mechanism of action, by the early 90s evidence began to accumulate linking the thiazolidinediones to the nuclear receptor PPAR-gamma. It was ultimately demonstrated that these molecules were high affinity ligands of PPAR-gamma and that they increased transcriptional activity of the receptor. Without wishing to be bound by theory, multiple lines of evidence now indicate that the antidiabetic activities of the thiazolidinediones are mediated by their direct interaction with the receptor and the subsequent modulation of PPAR-gamma target gene expression.

Thiazolidinediones of use in the methods of the invention include: (1) rosiglitazone; (2) pioglitazone; (3) troglitazone; (4) netoglitazone (also known as MCC-555 or isaglitazone or neoglitazone); and (5) 5-BTZD.

Other PPAR modulators of use in the invention include modulators that have recently been the subject of clinical trials: (1) Muraglitazar (PPAR gamma and alpha agonist, Bristol-Myers/Merck); (2) Galida tesaglitazar (PPAR gamma and alpha agonist, AstraZeneca); (3) 677954 (PPAR gamma, alpha, and delta agonist, GlaxoSmithKline); (4) MBX-102 (PPAR gamma partial agonist/antagonist, Metabolex); (5) T 131 (PPAR gamma selective modulator, Tularik/Amgen); (6) LY818 (PPAR gamma and alpha partial agonist, Eli Lilly/Ligand); (7) LY929 (PPAR gamma and alpha agonist, Eli Lilly/Ligand); and (8) PLX204 (PPAR gamma, alpha, and delta agonist, Plexxikon). See, e.g., BioCentury, Jun. 14, 2004. Further PPAR modulators include LY 519818, L-783483, L-165461, and L-165041.

Additionally, the non-thiazolidinediones that act as insulin-sensitizing agents include, but are not limited to: (1) JT-501 (JTT 501, PNU-1827, PNU-716-MET-0096, or PNU 182716: 4-(4-(2-(5-methyl-2phenyl-oxazol-4-yl)ethoxy)

benzyl)isoxazolidine-3,5-dione; (2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl) or N-(2-benzoylphenyl)-O-(2-(5-methyl-2-phenyl-4-oxazolyl)ethyl)-L-tyrosine, or (S)-2-(2-benzoylphenylamino)-3-(4-12-(5-methyl-2-phenyl-2-oxazo-4-yl)ethoxyphenyl) propionic acid, or GW2570 or GI-262570).

Other agents have also been shown to have PPAR modulator activity such as PPAR-gamma, SPPAR-gamma, and/or PPAR-alpha/delta agonist activity. Examples are: (1) AD 5075 (5-(4-(2-hydroxy-2-(5-methyl-2-phenyloxazol-4-yl) ethoxy)benzyl)-thiazolidine-2,4-dione); (2) R 119702 (or CI 1037 or CS 011); (3) CLX-0940 (peroxisome proliferator-activated receptor alpha agonist/peroxisome proliferator-activated receptor gamma agonist); (4) LR-90 (2,5,5-tris(4-chlorophenyl)-1,3-dioxane-2-carboxylic acid, PPAR alpha/gamma agonist); (5) CLX-0921 (PPAR gamma agonist); (6) CGP-52608 (PPAR agonist); (7) GW-409890 (PPAR agonist); (8) GW-7845 (2((S)-1-carboxy-2-(4-(2-(5-methyl-2-phenyl-oxazol-4-yl)-ethoxy)-phenyl)-ethyamino)-benzoic acid methyl ester, PPAR agonist); (9) L-764406 (2-benzenesulphonylmethyl-3-chloroquinoxaline, PPAR agonist); (10) LG-101280 (PPAR agonist); (11) LM-4156 (PPAR agonist); (12) Risarestat (CT-112, (+)-5-(3-ethoxy-4-(pentyloxy)phenyl-2,4-thiazolidinedione aldose reductase inhibitor); (13) YM 440 (PPAR agonist); (14) AR-H049020 (PPAR agonist); (15) GW 0072 ((+)-(2S,5S)-4-(4-(5-((dibenzy carbomoyl)methyl)-2-heptlyl-4-oxothiazolidin-3-yl butyl)benzoic acid); (16) GW 409544 (GW-544 or GW-409544); (17) NN 2344 (DRF 2593); (18) NN 622 (DRF 2725); (19) AR-H039242 (AZ-242); (20) GW 9820 (fibrate); (21) GW 1929 (N-(2-benzoylphenyl)-O-(2-(methyl-2-pyridinylamino)ethyl)-L-tyrosine, known as GW 2331, PPAR agonist); (22) SB 219994 ((S)-4-(2-(2-benzoxazolylmethylamino)ethoxy)-alpha-(2,2,2-trifluoroethoxy)benzen epropanoic acid or 3-(4-(2-(N-(2-benzoxazolyl)-N-methylamino)ethoxy)phenyl)-2 (S)-(2,2,2-trifluoroethoxy)propionic acid or benzenepropanoic acid, 4-(2-(2-benzoxazolylmethylamino) ethoxy)-alpha-(2,2,2-trifluoroethox-y)-, (alpha S)-, PPAR alpha/gamma agonist); (23) L-796449 (PPAR alpha/gamma agonist); (24) Fenofibrate (propanoic acid, 2-[4-(4-chlorobenzoyl)phenoxy]-2-methyl-, 1-methylethyl ester, known as TRICOR, LIPCOR, LIPANTIL, LIPIDIL MICRO PPAR alpha agonist); (25) GW-9578 (PPAR alpha agonist); (26) GW-2433 (PPAR alpha/gamma agonist); (27) GW-0207 (PPAR gamma agonist); (28) LG-100641 (PPAR gamma agonist); (29) LY-300512 (PPAR gamma agonist); (30) NID525-209 (NID-525); (31) VDO-52 (VDO-52); (32) LG 100754 (peroxisome proliferator-activated receptor agonist); (33) LY-510929 (peroxisome proliferator-activated receptor agonist); (34) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and (35) GW-1536 (PPAR alpha/gamma agonist).

In some aspects of the invention, radioisotopes can be delivered via the implantable device of the invention. For example, it is well known in the art that various methods of radionuclide therapy can be used for the treatment of cancer and other pathological conditions, as described, e.g., in Harbert, "Nuclear Medicine Therapy", New York, Thieme Medical Publishers, 1987, pp. 1-340. A clinician experienced in these procedures will readily be able to adapt the implantable device described herein to such procedures to mitigate or treat disease amenable to radioisotope therapy thereof.

In some aspects the radio isotopes include but are not limited to isotopes and salts of isotopes with short half life: such as Y-90, P-32, I-131, Au 198. Therefore in one aspect of the invention, the implantable device can be utilized to deliver radioisotopes.

It is also well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press, Oxford, 1986), in Immunoconjugates. Antibody Conjugates in Radioimaging and Therapy of Cancer (C.-W. Vogel, ed., 3-300, Oxford University Press, New York, 1987), in Dillman, R. O. (CRC Critical Reviews in Oncology/Hematology 1:357, CRC Press, Inc., 1984), in Pastan et al. (Cell 47:641, 1986), in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in Goldenberg, U.S. Pat. Nos. 4,331,647, 4,348,376, 4,361,544, 4,468,457, 4,444,744, 4,460,459, 4,460,561 and 4,624,846, and in Rowland, U.S. Pat. No. 4,046,722, Rodwell et al., U.S. Pat. No. 4,671,958, and Shih et al., U.S. Pat. No. 4,699,784, the disclosures of all of which are incorporated herein in their entireties by reference.

Other thiazolidinedione and non-thiazolidinedione insulin sensitizers of use in the invention are described in, e.g., Leff and Reed (2002) Curr. Med. Chem.—Imun., Endoc., & Metab. Agents 2:33-47; Reginato et al. (1998) J. Biol. Chem., 278 32679-32654; Way et al. (2001) J. Biol. Chem. 276 25651-25653; Shiraki et al. (2005) JBC Papers in Press, published on Feb. 4, 2005, as Manuscript M500901200, and U.S. Pat. Nos. 4,703,052; 6,008,237; 5,594,016; 6,838,442; 6,329,423; 5,965,589; 6,677,363; 4,572,912; 4,287,200; 4,340,605; 4,438,141; 4,444,779; 4,572,912; 4,687,777; 4,725,610; 5,232,925; 5,002,953; 5,194,443; 5,260,445; 6,300,363; 6,034,110; and 6,541,493; U.S. Patent Application Publications 2002/0042441; 2004/0198774 and 2003/0045553; EP Patent Nos. 0139421 and 0332332; and PCT Publication Nos. WO 95/35314; WO 00/31055; WO 01/3640, all of which are incorporated by reference herein in their entirety.

Netoglitazone

One thiazolidinedione PPAR modulator for use in the methods of the invention is netoglitazone (5-[{6-(2-fluorobenzyl)oxy-2-naphthyl}methyl]-2,4-thiazolidinedione; MCC-555). Structures and methods of preparation of netoglitazone and various forms of netoglitazone of use in the invention are described in, e.g., U.S. Pat. Nos. 5,594,016; 6,541,493; 6,541,493; 6,838,442; U.S. Patent application No. 2004/0198774 and 2003045553; PCT Publication Nos. WO 00/31055; WO 01/36401; WO 03/018010, and WO 00/73252; Japanese Patent Unexamined Publication (KOKAI) Nos. (Hei) 6-247945/1994 and (Hei) 10-139768/1998; Japanese Patents 2001172179 and 2003040877; and Reginato et al. (1998) J. Biol. Chem. 273: 32679-32684; all of which are incorporated by reference herein in their entirety.

It has been reported that netoglitazone is more efficacious than pioglitazone and troglitazone in lowering plasma glucose, insulin, and triglyceride levels and that it is about threefold more potent than rosiglitazone. The activity of netoglitazone appears to be context-specific, as in some cell types it behaves as a full agonist of PPAR-gamma and as a partial agonist or antagonist in others. In addition, it appears to modulate PPAR-alpha and delta as well. See, e.g., U.S. patent application Publication No. 2004/0198774.

Forms of Drugs

Some compounds useful in the invention, including the TZD PPAR modulators such as netoglitazone, may have one or more asymmetric carbon atoms in their structure. In addition, stereochemically pure isomeric forms of the compounds as well as their racemates can also be delivered using one or more matrix disclosed herein. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Some compounds useful in the invention may have various individual isomers, such as trans and cis, and various alpha and beta attachments (below and above the plane of the drawing). In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. Unless otherwise noted the scope of the bioactive agents, that can be included in the matrix(es) disclosed herein, is intended to cover all such isomers or stereoisomers per se, as well as mixtures of cis and trans isomers, mixtures of diastereomers and racemic mixtures of enantiomers (optical isomers) as well.

In addition, compounds to be delivered by or included in the matrixes of the invention may be prepared in various polymorphic forms. For example, insulin sensitizers of use in the invention can occur in polymorphic forms, and any or all of the polymorphic forms of these insulin sensitizers are contemplated for use in the invention. Polymorphism in drugs may alter the stability, solubility and dissolution rate of the drug and result in different therapeutic efficacy of the different polymorphic forms of a given drug. The term polymorphism is intended to include different physical forms, crystal forms, and crystalline/liquid crystalline/non-crystalline (amorphous) forms. Polymorphism of compounds of therapeutic use has is significant, as evidenced by the observations that many antibiotics, antibacterials, tranquilizers etc., exhibit polymorphism and some/one of the polymorphic forms of a given drug may exhibit superior bioavailability and consequently show much higher activity compared to other polymorphs. For example, Sertraline, Frentizole, Ranitidine, Sulfathiazole, and Indomethacine are some of the pharmaceuticals that exhibit polymorphism.

Some embodiments of the invention include the use of netoglitazone in one of its polymorphic forms. Netoglitazone can be prepared in various polymorphic forms. Any polymorphic forms of netoglitazone known in the art may be used in the methods of the invention, either separately or in combination. Thus, the methods of the invention include association studies using any or all of the polymorphic forms of netoglitazone, as well as screening and treatment using any or all of the polymorphic forms of netoglitazone, compositions and kits based on these forms, and the like.

Polymorphic forms of netoglitazone include the A, B, C, D, E and amorphous crystal forms described in PCT Published Application No. WO 01/36401 and in U.S. Pat. No. 6,541, 493; for example, the E form is described in PCT Published Application No. WO 01/36401.

Some of the compounds described herein may exist with different points of attachment of hydrogen coupled with double bond shifts, referred to as tautomers. An example is a carbonyl (e.g. a ketone) and its enol form, often known as keto-enol tautomers. The individual tautomers as well as mixtures thereof are encompassed within the invention.

Prodrugs are compounds that are converted to the claimed compounds as they are being administered to a patient or after they have been administered to a patient. The prodrugs are compounds of this invention, and the active metabolites of the prodrugs are also compounds of the invention.

Other agents useful in the methods of the invention include, but are not limited to:

1. Biguanides, which decrease liver glucose production and increases the uptake of glucose. Examples include metformin such as: (1) 1,1-dimethylbiguanide (e.g., Metformin-DepoMed, Metformin-Biovail Corporation, or METFORMIN GR (metformin gastric retention polymer)); and (2) metformin hydrochloride (N,N-dimethylimidodicarbonimidic diamide monohydrochloride, also known as LA 6023, BMS 207 150, GLUCOPHAGE, or GLUCOPHAGE XR.

2. Alpha-glucosidase inhibitors, which inhibit alpha-glucosidase, and thereby delay the digestion of carbohydrates. The undigested carbohydrates are subsequently broken down in the gut, reducing the post-prandial glucose peak. Examples include, but are not limited to: (1) acarbose (D-glucose, O-4, 6-dideoxy-4-(((1S-(1alpha,4alpha,5beta,6alpha))-4,5,6-trihydroxy-3-(hydroxymethyl)-2-cyc-lohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE); (2) Miglitol (3,4,5-piperidinetriol, 1-(2-hydroxyethyl)-2-(hydroxymethyl)-, (2R(2alpha,3beta, 4alpha,5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL); (3) CKD-711 (0-4-deoxy-4-((2,3-epoxy-3-hydroxymethyl-4,5, 6-trihydro-xycyclohexane-1-yl)amino)-alpha-b-glucopyranosyl-(1-4)-alpha-D-glucopyran-osyl-(1-4)-D-glucopyranose); (4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542); (5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and (6) Voglibose (3,4-dideoxy-4-((2-hydroxy-1-(hydroxymethyl)ethyl) amino)-2-C-(hydroxymethyl)-D-epi-inositol or D-epi-lnositol, 3,4-dideoxy-4- -((2-hydroxy-1-(hydroxymethyl)ethyl) amino)-2-C-(hydroxymethyl)-, also known as A 71100, AO 128, BASEN, GLUSTAT, VOGLISTAT.

3. Insulins include regular or short-acting, intermediate-acting, and long-acting insulins, injectable, non-injectable or inhaled insulin, transderamal insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to: (1) Biota; (2) LP 100; (3) (SP-5-21)-oxobis(1-pyrrolidinecarbodithioato-S,S') vanadium, (4) insulin as part (human insulin (28B-L-aspartic acid) or B28-Asp-insulin, also known as insulin X14, INA-X14, NOVORAPID, NOVOMIX, or NOVOLOG); (5) insulin detemir (Human 29B-(N-6-(1-oxotetradecyl)-L-lysine)-(1A-21A), (1B-29B)-Insulin or NN 304); (6) insulin lispro ("28B-L-lysine-29B-L-proline human insulin, or Lys (B28), Pro (B29) human insulin analog, also known as lys-pro insulin, LY 275585, HUMALOG, HUMALOG MIX 75/25, or HUMALOG MIX 50/50); (7) insulin glargine (human (A21-glycine, B31-arginine, B32-arginine) insulin HOE 901, also known as LANTUS, OPTISULIN); (8) Insulin Zinc Suspension, extended (Ultralente), also known as HUMULIN U or ULTRALENTE; (9) Insulin Zinc suspension (Lente), a 70% crystalline and 30% amorphous insulin suspension, also known as LENTE ILETIN II, HUMULIN L, or NOVOLIN L; (10) HUMULIN 50/50 (50% isophane insulin and 50% insulin injection); (11) HUMULIN 70/30 (70% isophane insulin NPH and 30% insulin injection), also known as NOVOLIN 70/30, NOVOLIN 70/30 PenFill, NOVOLIN 70/30 Prefilled; (12) insulin isophane suspension such as NPH ILETIN II, NOVOLIN N, NOVOLIN N PenFill, NOVOLIN N Prefilled, HUMULIN N; (13) regular insulin injection such as ILETIN II Regular, NOVOLIN R, VELOSULIN BR, NOVOLIN R PenFill, NOVOLIN R Prefilled, HUMULIN R, or Regular U-500 (Concentrated); (14) ARIAD; (15) LY 197535; (16) L-783281; and (17) TE-17411.

4. Insulin secretion modulators such as (1) glucagon-like peptide-1 (GLP-1) and its mimetics; (2) glucose-insulinotropic peptide (GIP) and its mimetics; (3) exendin and its mimetics; (4) dipeptyl protease (DPP or DPPIV) inhibitors such as (4a) DPP-728 or LAF 237 (2-pyrrolidinecarbonitrile, 1-(((2-((5-cyano- -2-pyridinyl)amino)ethyl)amino)acetyl), known as NVP-DPP-728, DPP-728A, LAF-237); (4b) P 3298 or P32/98 (di-(3N-((2S,3S)-2-amino-3-methyl-pentanoyl-)-1, 3-thiazolidine) fumarate); (4c) TSL 225 (tryptophyl-1,2,3,4-tetrahydroisoquinoline-3-carboxyli-c acid); (4d) Valine pyrrolidide (valpyr); (4e) 1-aminoalkylisoquinolinone-4-carboxylates and analogues thereof; (4f) SDZ 272-070 (1-(L-Valyl) pyrrolidine); (4g) TMC-2A, TMC-2B, or TMC-2C; (4h) Dipeptide nitriles (2-cyanopyrrolodides); (4i) CD26 inhibitors; and (4j) SDZ 274-444; (5) glucagon antagonists such as AY-279955; and (6) amylin agonists which include, but are not limited to, pramlintide (AC-137, Symlin, triproamylin or pramlintide acetate).

5. Insulin secretagogues, which increase insulin production by stimulating pancreatic beta cells, such as: (1) asmitiglinide ((2 (S)-cis)-octahydro-gamma-oxo-alpha-(phenylmet-hyl)-2H-isoindole-2-butanoic acid, calcium salt, also known as mituglimide calcium hydrate, KAD 1229, or S 21403); (2) Ro 34563; (3) nateglinide (trans-N-((4-(1-methylethyl)cyclohexyl)carbonyl)-D-phenylalanine, also known as A 4166, AY 4166, YM 026, FOX 988, DJN 608, SDZ DJN608, STARLIX, STARSIS, FASTIC, TRAZEC); (4) JTT 608 (trans-4-methyl-gamma-oxocyclohexanebutanoic acid); (5) sulfonylureas such as: (5a) chlorpropamide (1-[(p-chlorophenyl)sulfonyl]-3-propylurea, also known as DIABINESE); (5b) tolazamide (TOLINASE or TOLANASE); (5c) tolbutamide (ORINASE or RASTINON); (5d) glyburide (1-[[p-[2-(5-chloro-o-anisamido)ethyl]phenyl]sulfon-yl]-3-cyclohexylurea, also known as Glibenclamide, DIABETA, MICRONASE, GLYNASE PresTab, or DAONIL); (5e) glipizide (1-cyclohexyl-3-[[p-[2-(5-ethylpyrazinecarboxamido)e-thyl]phenyl]sulfonyl]urea, also known as GLUCOTROL, GLUCOTROL XL, MINODIAB, or GLIBENESE); (5f) glimepiride (1H-pyrrole-1-carboxamide, 3-ethyl-2,5-dihydro-4-m-ethyl-N-[2-[4-[[[[(4-methylcyclohexyl)amino]carbonyl]amino]sulfonyl]phenyl-]ethyl]-2-oxo-, trans-, also known as Hoe-490 or AMARYL); (5g) acetohexamide (DYMELOR); (5h) gliclazide (DIAMICRON); (5i) glipentide (STATICUM); (5j) gliquidone (GLURENORM); and (5k) glisolamide (DIABENOR); (6) K+ channel blockers including, but not limited to, meglitinides such as (6a) Repaglinide ((S)-2-ethoxy-4-(2-((3-methyl-1-(2-(1-piperidinyl) phenyl)butyl)amino)-2-oxoethyl)benzoic acid, also known as AGEE 623, AGEE 623 ZW, NN 623, PRANDIN, or NovoNorm); (6b) imidazolines; and (6c) α-2 adrenoceptor antagonists; (7) pituitary adenylate cyclase activating polypeptide (PAcAP); (8) vasoactive intestinal peptide (VIP); (9) amino acid analogs; and (10) glucokinase activators.

Growth Factors such as: (1) insulin-like growth factors (IGF-1, IGF-2); (2) small molecule neurotrophins; (3) somatostatin; (4) growth hormone-releasing peptide (GHRP); (5) growth hormone-releasing factor (GHRF); and (6) human growth hormone fragments. Immunomodulators such as: (1) vaccines; (2) T-cell inhibitors; (3) monoclonal antibodies; (4) interleukin-1 (IL-1) antagonists; and (5) BDNF. Glucose resorption inhibitors such as those described in U.S. patent application No. 2003/0045553. Other antidiabetic agents: (1) rHu-Glucagon; (2) DHEA analogs; (3) carnitine palmitoyl transferase (CPT) inhibitors; (4) islet neurogenesis; (5) pancreatic p amyloid inhibitors; and (6) UCP (uncoupling protein)-2 and UCP-3 modulators.

In one aspect the matrix structures of the invention can be utilized to elicit an immune response in a subject. Therefore, in one embodiment, the matrix releases an antigen or immunogen in a time controlled manner so as to elicit an immune response in a subject. Such an immune response can impart protective immunity or "vaccinate" an animal against the desired antigen or immunogen. In an alternative, embodiment, the antigen or immunogen can be linked to a portion of the nucleic acid matrix (or gel or scaffold), or to the nucleic acid matrix-copolymer structure.

Additional agents of use in the invention include any agents known in the art for treatment of disorder of blood glucose regulations and/or their complications. Such agents include, but are not limited to, cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPAR.alpha. agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol; PPARdelta agonists such as those disclosed in WO97/97/28149; antiobesity compounds such as fenfluramine, dexfenfluramine, phentiramine, sulbitramine, orlistat, neuropeptide Y5 inhibitors, and, β3 adrenergic receptor agonist; and ileal bile acid transporter inhibitors.

Classes of Drugs

Drugs may be classed into mechanistic classes, structural classes, classes based on pharmacological effect, and other classes of drugs that are based on the chemical or biological nature of the drugs, or that are empirically based.

Mechanistic classifications are based on the mechanism of action of drugs, e.g., receptor targets or other targets of the drugs. For example, drugs that primarily act on the autonomic nervous system may be classed as cholinoreceptor-activating drugs, or cholinesterase-inhibiting drugs, or cholinoreceptor-blocking drugs, or adrenoceptor-activating drugs, or adrenoceptor-blocking drugs.

However, as is known in the art, often drugs do not have a known target or a precisely defined mechanism, and may be classed according to similarities in other aspects the drugs, such as similarities of the chemical structure that are thought to be important to the action of the drugs. Such similarities include structural components, optical isomerism, crystal structure, and the like.

Drugs may also be classed based on their major pharmacological action, e.g., lipid-lowering drugs, antidepressants, anxiolytics, and the like. The second drug may be placed in the same class as the first drug by in vitro and/or in vivo studies; in some embodiments, action through the same or similar mechanism may be predicted from structural analysis.

In some embodiments, drugs are classified based on their effects in one or more in vitro, cellular, tissue, organ, or animal models. Such effects may be molecular, supramolecular, cellular, tissue, organ, or whole-organism effects, or combinations thereof. In some embodiments, drugs are classified based on their effects in one or more animal models together with associations between genotypes and response in the animal models. For example, drug A may cause response M in a mammal, e.g., a rat, mouse, or primate, of genotype X (e.g., genotype at one or more SNPs), and may cause response N in a primate of genotype Y. If drug B is found to cause response M in a mammal of genotype X and response N in a mammal of genotype Y, then drug B is considered to be in the same class as drug A. It will be appreciated that such classification may be greatly refined based on the number of genetic variations included in the genotype, the number of responses measured, and the like. The animal model allows a much wider range of drugs to be tested, as well as more invasive parameters to be measured as indications of response, and can allow a much more extensive database to be established in a relatively short time, compared to human testing.

In other embodiments, expression profiles for a drug in a model system may be used to classify the drug. For example, all, most, or some of the known drugs of a class of drugs that has an effect in humans (e.g., statins that lower the risk of heart disease) may be tested in an animal model. Animals administered the drug may show consistent profiles of gene expression in response to the drug (e.g., increases in expression of a gene or set of genes related to antiinflammatory activity). Other drugs of other classes may be tested in animal models. The expression profiles associated with the drugs in a particular class may be correlated. A new drug may be assigned to a drug class based on its expression profile in one or more animal models. The associations of one or more drugs in that class between one or more genetic variations and a response to the drug(s) may be used to modulate the use of the new drug, for example, in research (e.g., clinical trials) and/or in the clinical setting.

In some embodiments, a new drug in a class of drugs is first tested in a model, e.g. an animal model, in which other drugs in the class of drugs have been tested, and in which a genotype for the animal is used to predict responses to the new drug. The results of the animal studies can be used to refine predictions for the association between genetic variations and response to a new drug in humans. Animal models may be developed or existing animal models may be used. The animal model can be for a particular physiological, biochemical, or metabolic state, e.g., a disease or pathological state. Healthy or superhealthy states may also be modeled (e.g., decelerated aging).

Drugs may be further put into classes, or into subclasses of the same class, by classifications based on their mode administration (e.g., intravascular, intramuscular, subcutaneous, ocular, inhalation, oral, sublingual, suppository, skin, via pump, and the like), formulation type (e.g., rapid acting, sustained release, enterically coated, etc.), mode of uptake and delivery to site of action, metabolism (e.g., drugs metabolized through Phase I reactions such as oxidation via hepatic microsomal P450 system and subclasses thereof, through oxidation via nonmicrosomal mechanisms and subclasses thereof, through reduction, through hydrolysis and subclasses thereof drugs metabolized through Phase II reactions such as glucoronidation, acetylation, mercapturic acid formation, sulfate conjugation, N-, O-, and S-methylation, trans-sulfuration; and combinations thereof), metabolic products and/or byproducts and their structure and/or function, pharmacokinetics, pharmacodynamics, elimination, and the like It will be appreciated that these classifications are exemplary only, and that any means of classifying drugs that allows a non-random predictability of the effects of drugs in the class may be used. Further systems of drug classification and specific drugs within each class may be found in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutica Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Any suitable class of drugs for which genotyping and association studies are possible for at least one member of the class may be the subject of the described methods and compositions. Classes include the insulin sensitizers as described herein, e.g., PPAR modulators. Thus, in some embodiments, the invention provides a method for predicting an individual's responsiveness to an insulin sensitizer, e.g., a PPAR modulator based on the individual's genotype and the results of association studies between genotype and responsiveness to another insulin sensitizer, e.g., PPAR modulator. In some embodiments, the prediction of an individual's responsiveness to an insulin sensitizer, e.g., PPAR modulator is used to include or exclude the individual in a clinical trial. In some embodiments, the prediction of an individual's responsiveness to an insulin sensitizer, e.g., PPAR modulator is used to modulate the individual's administration of another insulin sensitizer, e.g., PPAR modulator. In some embodiments such modulation occurs in a clinical trial. In some embodiments, the prediction of an individual's responsiveness to an insulin sensitizer, e.g., PPAR modulator is used to determine that the individual should be treated with a drug other than an insulin sensitizer, or in some embodiments a PPAR modulator.

Mechanistic Classes of Drugs

One non-exclusive exemplary classes of drugs for which genotyping and association studies with one member may be used to predict effects of another member include, mechanistic classes of drugs used in the treatment of diabetes (including PPAR modulators). This class of drugs also illustrates how drugs can also be subclassed by, e.g., mode of administration. For example, insulin and insulin analogs may be formulated for administration by injection, nasal spray, transdermal, oral or inhalation routes. Each type of formulation can have unique profiles of responses and associated genetic variations. An example of classifications of such drugs by mechanism, together with representative members of the mechanistic classes, is given in Table 4.

TABLE 4

Classes of Drugs for Treatment of Diabetes

| Class | Mechanism of Action | Examples |
|---|---|---|
| Peroxisome Proliferator-Activated Receptor (PPAR) Agonists | Target PPAR-gamma or PPAR-gamma and -alpha (see below). PPAR are nuclear receptors that help regulate glucose and lipid metabolism. Activation of PPAR-gamma improves insulin sensitivity and thus improves glycemic control. | Rosiglitazone, Pioglitazone, Balaglitazone, see also others described herein |
| Dual-Action Peroxisome Proliferator-Activated Receptor Agonists | Act on both PPAR-gamma and PPAR-alpha. PPAR-alpha activation has effects on cellular uptake of fatty acids and their oxidation, and on lipoprotein metabolism. May also act to reduce inflammatory response in vascular endothelial cells. | TAK-559, Muraglitazar, Tesaglitazar, Netoglitazone, see also others described herein |
| Biguanidines | Complete mechanism is not known. Reduces gluconeogenesis in the liver by inhibiting glucose-6-phosphatase. | Metformin, Metformin GR |
| Sulfonylureas | Induce insulin secretion by binding to cellular receptors that cause membrane depolarization and insulin exocytosis. | Glimepride, Glyburide/glibenclamide, Glipizide, Gliclazide. Tobutamide |
| Insulin and Insulin Analogs (Injectable, Inhaled, Oral, Transdermal, Intranasal) | Supplements endogenous insulin. Insulin analogs have a variety of amino acid changes and have altered onset of action and duration of action, as well as other properties, compared to native insulin. Inhaled insulin is absorbed through the alveoli. Spray oral insulin is absorbed by the buccal mucosa and intranasal through the nasal mucosa. Transdermal insulin is absorbed through the skin. | Insulin lispro, Insulin aspart, Insulin glargine, Exubera, AERx Insulin Diabetes Management System, HIM-2, Oaralin, Insulin detemir, Insulin glulisine |
| Meglitinides | Are thought to bind to a nonsulfonylurea beta cell receptor and act to cause insulin secretion by mechanism similar to sulfonylureas | Repaglinide, Nateglinide, Mitiglinide |
| Alpha-Glucosidase Inhibitors | Inhibit carbohydrate digestion. Act at brush border of intestinal epithelium. | Acarbose, Miglitol, Voglibose |
| Glucagon-Like Peptide(GLP)-1 Analogs | Diabetic patients may lack native GLP-1, and analogs act as substitutes. GLP-1 is an intestinal peptide hormone that induces glucose-dependent insulin secretion, controls gastric emptying, inhibits appetite, and modulates secretion of glucagon and somatostatin. | Exenatide, Exenatide LAR, Liraglutide, ZP 10, BN51077, |
| Dipeptidyl Peptidase (DPP)-IV Inhibitors | Inhibit DPP-IV, a ubiquitous enzyme that cleaves and inactivates GLP-1, thus inhibition of DPP-IV increases GLP-1 activity | LAF-237, p-32/98, MK-431, P3298, NVP LAF 237, |
| Pancreatic Lipase Inhibitors | Inhibits lipases, thus inhibiting uptake of dietary fat. This causes weight loss, improves insulin sensitivity and lowers hyperglycemia. | Orlistat |
| Amylin Analogs | Act to augment amylin, which acts with insulin by slowing glucose absorption from the gut and slows after-meal glucose release from liver. | Pramlintide |
| Dopamine D2 receptor agonists | Thought to act to alleviate abnormal daily variations in central neuroendocrine activity that can contribute to metabolic and immune system disordered. | Bromocriptine |
| Immuno-suppressants | Suppress autoimmune response thought to be implicated in Type I and possibly Type II diabetes. Example: Humanized monoclonal antibody that recognizes and inhibits the alpha subunit of IL-2 receptors; humanized Mab that binds to T cell CD3 receptor to block function of T-effector cells that attack the body and cause autoimmune disease | Daclizumab, NBI 6024, TRX-TolerRx, OKT3-gamma-1-ala-ala |
| Insulin-like growth factor-1 agonists | Recombinant protein complex of insulin-like growth factor-1 and binding protein-3; regulates the delivery of somatomedin to target tissues. Reduces insulitis severity and beta cell destruction | Somatomedin-1 binding protein 3 |
| Insulin sensitizers | Insulin sensitizers, generally orally active | S15261, Dexlipotam, CLX 0901, R 483, TAK 654 |
| Growth hormone releasing factor agonists | Mimic the action of native GHRF | TH9507, SOM 230 |
| Glucagon antagonists | Inhibit glucagon action, stimulating insulin production and secretion, resulting in lower postprandial glucose levels | Liraglutide, NN 2501 |
| Diabetes type 1 vaccine | Prevents destruction of pancreatic beta cells that occurs in type 1 diabetes | Q-Vax, Damyd vaccine |
| Sodium-glucose co-transporter inhibitor | Selectively inhibits the sodium glucose co-transporter, which mediates renal reabsorption and intestinal absorption of glucose to maintain appropriate blood glucose levels. | T 1095 |
| Glycogen phosphorylase inhibitors | Inhibit glycogen phosphorylase, thus slowing release of glucose | Ingliforib |
| Undefined mechanisms | Drugs that act in ways beneficial to those with Type I or Type II Diabetes Mellitus, e.g., by reducing blood glucose and triglyceride levels, whose mechanisms have not been elucidated. | FK 614, INGAP Peptide, R 1439 |
| Antisense oligonucleotides | Bind to RNA and cause its destruction, thereby decreasing protein production from corresponding gene. | ISIS 113715 |
| Insulinotropin agonists | Stimulate insulin release | CJC 1131 |
| Gluconeogenesis inhibitors | Inhibit gluconeogenesis, thus modulating blood glucose levels | CS 917 |
| Hydroxysteroid dehydrogenase inhibitors | Inhibit hydroxysteroid dehydrogenase, which are responsible for excess glucocorticoid production and hence, visceral obesity | BVT 3498 |
| Beta 3 adrenoceptor agonist | Agonist for beta 3 adrenoceptor, decreases blood glucose and suppresses weight gain | YM 178, Solabegron, N5984, |
| Nitric oxide antagonist | Decreases effects of NO | NOX 700 |

TABLE 4-continued

Classes of Drugs for Treatment of Diabetes

| Class | Mechanism of Action | Examples |
|---|---|---|
| Carnitine palmitoyl-transferase inhibitor | Inhibits carnitine palmitoyltransferase | ST 1326 |

In other embodiments, mechanistic classes of drugs used in the treatment of abnormal cholesterol and/or triglyceride levels in the blood are used in conjunction with a method or composition of the invention. Broad mechanistic classes include the statins, fibrates, cholesterol absorption inhibitors, nicotinic acid derivatives, bile acid sequestrants, cholesteryl ester transfer protein inhibitors, reverse lipid transport pathway activators, antioxidants/vascular protectants, acyl-CoA cholesterol acyltransferase inhibitors, peroxisome proliferator activated receptor agonists, microsomal triglyceride protein inhibitors, squalene synthase inhibitors, lipoprotein lipase activators, lipoprotein (a) antagonists, and bile acid reabsorption inhibitors. An example of classification of such drugs by mechanism, together with representative members of the mechanistic classes, is given in Table 5.

TABLE 5

Classes of Drugs for Treatment of Abnormal Cholesterol and/or Triglyceride Levels in the Blood

| Class | Mechanism of Action | Examples |
|---|---|---|
| Statins | Competitive inhibitors of HMG-CoA reductase | Atorvastatin, Simvastatin, Pravastatin, Fluvastatin, Rosuvastatin, Lovastatin, Pitavastatin, Cerivastatin (withdrawn), |
| Fibrates | PPARα activators | Fenofibrate, Bezafibrate, Gemfibrozil, clofibrate, ciprofibrate |
| Cholesterol Absorption Inhibitors | May inhibit NCP1L1 in gut | Ezetimibe |
| Nicotinic Acid Derivatives | Inhibits cholesterol and triglyceride synthesis, exact mechanism unknown | Niacin |
| Bile Acid Sequestrants | Interrupt the enterohepatic circulation of bile acids | Colesevelam, Cholestyramine, Colestimide, Colestipol |
| Cholesteryl Ester Transfer Protein Inhibitors | Inhibit cholesteryl ester transfer protein, a plasma protein that mediates the exchange of cholesteryl esters from antiatherogenic HDL to proatherogenic apolipoprotein B-containing lipoproteins | JTT-705, CETi-1, Torcetrapib |
| Reverse Lipid Transport Pathway Activators | Stimulate reverse lipid transport, a four-step process from removing excess cholesterol and other lipids from the walls of arteries and other tissues | ETC-216, ETC-588, ETC-642, ETC-1001, ESP-1552, ESP-24232 |
| Antioxidants/ Vascular Protectants | Inhibit vascular inflammation and reduce cholesterol levels; block oxidant signals that switch on vascular cellular adhesion molecule (VCAM)-1 | AGI-1067, Probucol (withdrawn) |
| Acyl-CoA Cholesterol Acyltransferase (ACAT) Inhibitors | Inhibit ACAT, which catalyzes cholesterol esterification, regulates intracellular free cholesterol, and promotes cholesterol absorption and assemble of VLDL | Eflucimibe, Pactimibe, Avasimibe (withdrawn), SMP-797 |
| Peroxisome Proliferator Activated Receptor Agonists | Activate PPARs, e.g., PPARα, γ, and possibly δ, which have a variety of gene regulatory functions | Tesaglitazar, GW-50516, GW-590735, LY-929, LY-518674, LY-465608, LY-818 |
| Microsomal Triglyceride Transfer Protein (MTTP) Inhibitors | Inhibit MTTP, which catalyze the transport of triglycerides, cholesteryl ester, and phosphatidylcholine between membranes; required for the synthesis of ApoB. | Implitapide, CP-346086 |
| Squalene Synthase Inhibitors | Interfere with cholesterol synthesis by halting the action of liver enzymes; may also slow or stop the proliferation of several cell types that contribute to atherosclerotic plaque formation | TAK-475, ER-119884 |
| Lipoprotein Lipase Activators | Directly activate lipoprotein lipase, which promotes the breakdown of the fat portion of lipoproteins | Ibrolipim (NO-1886) |
| Liproprotein(a) Antagonists | Not yet established | Gembacene |
| Bile Acid Reabsorption Inhibitors | Inhibit intestinal epithelial uptake of bile acids. | AZD-7806, BARI-1453, S-8921 |

In other embodiments, mechanistic classes of drugs used in the treatment of depression are used in conjunction with a method or composition of the invention. Current or emerging antidepressant drugs act by a variety of mechanisms, e.g., selective serotonin reuptake inhibitors (SSRIs), serotonergic/noradrenergic agents, serotonin/noradrenergic/dopaminergic agents, tricyclic antidepressants, monoamine oxidase inhibitors (MAOIs), noradrenergic/dopaminergic agents, serotonin antagonists, serotonin agonists, substance P antagonists, and beta3 adrenoreceptor agonists. An example of classification of such drugs by mechanism, together with representative members of the mechanistic classes, is given in Table 6.

TABLE 6

Classes of Drugs for Treatment of depression

| Class | Mechanism of Action | Examples |
|---|---|---|
| Selective Serotonin Reuptake Inhibitor (SSRI) | Block presynaptic reuptake of serotonin. Exert little effect on norepinephrine or dopamine reuptake. Level of serotonin in the synaptic cleft is increased. | Escitalopram, Sertraline, Citalopram, Paroxetine, Paroxetin, controlled release, Fluoxetine, Fluoxetine weekly, Fluvoxamine, olanzapine/fluoxetine combination |
| Serotonergic/ noradrenergic agents | Inhibit both serotonin reuptake and norepinephrine reuptake. Different drugs in this class can inhibit each receptor to different degrees. Do not affect histamine, acetylcholine, and adrenergic receptors. | Venlafaxine; Reboxetine, Milnacipran, Mirtazapine, Nefazodone, Duloxetine |

TABLE 6-continued

Classes of Drugs for Treatment of depression

| Class | Mechanism of Action | Examples |
|---|---|---|
| Serotonergic/ noradrenergic/ dopaminergic agents | Several different mechanisms. Block norepinephrine, serotonin, and/or dopamine reuptake. Some have addictive potential due to dopamine reuptake inhibition. | Bupropion, Maprotiline, Mianserin, Trazodone, Dexmethylphenidate, Methyphenidate, Amineptine |
| Tricyclic Antidepressants | Block synaptic reuptake of serotonin and norepinephrine. Have little effect on dopamine. Strong blockers of muscarinic, histaminergic H1, and alpha-1-adrenergic receptors. | Amitriptyline, Amoxapine, Clomipramine, Desipramine, Doxepin, Imipramine, Nortriptyline, Protriptyline, Trimipramine |
| Irreversible Monoamine Oxidase Inhibitors | Monoamine oxidase (MAO) metabolizes monoamines such as serotonin and norepinephrine. MAO inhibitors inhibit MAO, thus increasing levels of serotonin and norepinephrine. | Isocarboxazid, Phenelzine, Tranylcypromine, Transdermal Selegiline |
| Reversible Monoamine Oxidase Inhibitors | See above. Short acting, reversible inhibitor, inhibits deamination of serotonin, norepinephrine, and dopamine. | Moclobemide |
| Serotonergic/ noradrenergic/ dopaminergic reuptake inhibitors | Act to block all of serotonin, norepinephrine, and dopamine reuptake. May have addictive potential due to dopamine reuptake inhibition. | DOV-216303, DOV-21947 |
| Noradrenergic/ dopaminergic agents | Block reuptake of norepinephrine and dopamine | GW-353162 |
| Serotonin Antagonists | Selective antagonist of one serotonin receptor (the 5-HT$_1$ receptor) | Agomelatine |
| Serotonin Agonists | Partial agonist of the 5-HT$_{1A}$ receptor. | Eptapirone, Vilazodone, OPC-14523, MKC-242, Gepirone ER |
| Substance P Antagonists | Modify levels of substance P, which is released during acute stress. | Aprepitant, TAK-637, CP-122721, E6006, R-763OPC-GW-597599 SR-58611 |
| Beta$_3$ Adrenoreceptor Agonists | Indirectly inhibit norepinephrine reuptake. Also being investigated for treatment of obesity and diabetes because they stimulate lipolysis and thermogenesis. | |

In other embodiments, mechanistic classes of drugs used in the treatment of multiple sclerosis are used in conjunction with a method or composition of the invention. These drugs can be classed as, e.g., recombinant interferons, altered peptide ligands, chemotherapeutic agents, immunosuppressants, corticosteroids, monoclonal antibodies, chemokine receptor antagonists, AMPA receptor antagonists, recombinant human glial growth factors, T-cell receptor vaccines, and oral immunomodulators. An example of classification of such drugs by mechanism, together with representative members of the mechanistic classes, is given in Table 7.

TABLE 7

Classes of Drugs for Treatment of Multiple Sclerosis

| Class | Mechanism of Action | Examples |
|---|---|---|
| Recombinant interferons | IFN-beta has numerous effects on the immune system. Exact mechanism of action in MS not known | Interferon-beta-1b, Interferon-beta-1a |

TABLE 7-continued

Classes of Drugs for Treatment of Multiple Sclerosis

| Class | Mechanism of Action | Examples |
|---|---|---|
| Altered peptide ligands | Ligands either templated on sequence of myelin basic protein, or containing randomly arranged amino acids (e.g., ala, lys, glu, tyr) whose structure resembles myelin basic protein, which is thought to be an antigen that plays a role in MS. Bind to the T-cell receptor but do not activate the T-cell because are not presented by an antigen-presenting cell. | Glatiramer acetate, MBP-8298, Tiplimotide, AG-284 |
| Chemotherapeutic agents | Immunosuppressive. MS is thought to be an autoimmune disease, so chemotherapeutics that suppress immunity improve MS | Mitoxantrone, Methotrexate, Cyclophosphamide |
| Immunosuppressants | Act via a variety of mechanisms to dampen immune response. | Azathioprine, Teriflunomide, Oral Cladribine |
| Corticosteroids | Induce T-cell death and may up-regulate expression of adhesion molecules in endothelial cells lining the walls of cerebral vessels, as well as decreasing CNS inflammation. | Methylprednisolone |
| Monoclonal Antibodies | Bind to specific targets in the autoimmune cascade that produces MS, e.g., bind to activated T-cells | Natalizumab, Daclizumab, Altemtuzumab, BMS-188667, E-6040, Rituximab, M1 MAbs, ABT 874, T-0047 |
| Chemokine Receptor Antagonists | Prevent chemokines from binding to specific chemokine receptors involved in the attraction of immune cells into the CNS of multiple sclerosis patients, and inhibiting immune cell migration into the CNS | BX-471, MLN-3897, MLN-1202 |
| AMPA Receptor Antagonists | AMPA receptors bind glutamate, an excitatory neurotransmitter, which is released in excessive quantities in MS. AMPA antagonists suppresses the damage caused by the glutamate | E-2007 |
| Recombinant Human Glial Growth Factor (GGF) | GGF is associated with the promotion and survival of oligodendrocytes, which myelinate neurons of the CNS. rhGGF may help myelinate oligodendrocytes and protect the myelin sheath. | Recombinant Human GGF2 |
| T-cell Receptor Vaccine | Mimic the part of the receptor in T cells that attack myelin sheath, which activates regulatory T cells to decrease pathogenic T-cells. | NeuroVax |
| Oral Immunomodulators | Various effects on the immune response that can modulate the process of MS | Simvastatin, FTY-720, Oral Glatiramer Acetate, FTY-720, Pirfenidone, Laquinimod |

In other embodiments, mechanistic classes of drugs used in the treatment of Parkinson's disease are used in conjunction with a method or composition of the invention. These classes include dopamine precursors, dopamine agonists, COMT inhibitors, MAO-B inhibitors, antiglutametergic agents, anticholinergic agents, mixed dopaminergic agents, adenosine A2a antagonists, alpha-2 adrenergic antagonists, antiapoptotic agents, growth factor stimulators, and cell replacements.

An example of classification of such drugs by mechanism, together with representative members of the mechanistic classes, is given in Table 8.

TABLE 8

Classes of Drugs for Treatment of Parkinson's Disease

| Class | Mechanism of Action | Examples |
|---|---|---|
| Dopamine Precursors | Act as precursors in the synthesis of dopamine, the neurotransmitter that is depleted in Parkinson's Disease. Usually administered in combination with an inhibitor of the carboxylase enzyme that metabolizes levodopa. Some (e.g., Duodopa) are given by infusion, e.g., intraduodenal infusion | Levodopa, Levodopa-carbidopa, Levodopa-benserazide, Etilevodopa, Duodopa |
| Dopamine Agonists | Mimic natural dopamine by directly stimulating striatal dopamine receptors. May be subclassed by which of the five known dopamine receptor subtypes the drug activates; generally most effective are those that activate receptors the in the D2 receptor family (specifically D2 and D3 receptors). Some are formulated for more controlled release or transdermal delivery. | Bromocriptine, Cabergoline, Lisuride, Pergolide, Pramipexole, Ropinirole, Talipexole, Apomorphine, Dihydroergocryptine, Lisuride, Piribedil, Talipexole, Rotigotin CDS, Sumanirole, SLV-308 |
| COMT Inhibitors | Inhibits COMT, the second major enzyme that metabolized levodopa. | Entacapone, Tolcapone, Entacapone-Levodopa-Carbidopa fixed combination, |
| MAO-B Inhibitors | MAO-B metabolizes dopamine, and inhibitors of MAO-B thus prolong dopamine's half-life | Selegiline, Rasagiline, Safinamide |
| Anti-glutamatergic Agents | Block glutamate release. Reduce levodopa-induced dyskinesia | Amantadine, Budipine, Talampanel, Zonisamide |
| Anticholinergic Agents | Thought to inhibit excessive cholinergic activity that accompanies dopamine deficiency | Trihexyphenidyl, Benztropine, Biperiden |
| Mixed Dopaminergic Agents | Act on several neurotransmitter systems, both dopaminergic and nondopaminergic. | NS-2330, Sarizotan |
| Adenosine A2a antagonists | Adenosine A2 antagonize dopamine receptors and are found in conjunction with dopamine receptors. Antagonists of these receptors may enhance the activity of dopamine receptors. | Istradefylline |
| Alpha-2 Adrenergic Antagonists | Not known. | Yohimbine, Idazoxan, Fipamezole |
| Antiapoptotic Agents | Can slow the death of cells associated with the neuro-degenerative process of Parkinson's disease. | CEP-1347, TCH-346 |
| Growth Factor Stimulators | Promote the survival and growth of dopaminergic cells. | GPI-1485, Glial-cell-line-derived Neurotrophic Factor, SR-57667, PYM-50028 |
| Cell Replacement Therapy | Replace damaged neurons with health neurons. | Spheramine |

The above classifications are exemplary only. It will be appreciated that a drug class need not be restricted to drugs used in the treatment of a single disease, but that a given mechanistic class may have members useful in the treatment of a number of diseases. For a example, MAO-B inhibitors are useful in the treatment of both Parkinson's disease and depression; as another example, statins are useful in the treatment of dyslipidemias but are also being found to have more general use in diseases where inflammation plays a major role, e.g., multiple sclerosis and other diseases.

Further classifications of drugs by mechanism are known in the art; often these classifications may be further classified by structure. Non-exclusive examples of drug classes useful in the methods and compositions of the invention, and representative members of these classes, include:

Sedative-Hypnotic Drugs, which include drugs that bind to the GABAA receptor such as the benzodiazepines (including alprazolam, chlordiazepoxide, clorazepate, clonazepam, diazepam, estazolam, flurazepam, halazepam, lorazepam, midazolam, oxazepam, quazepam, temazepam, triazolam), the barbiturates (such as amobarbital, pentobarbital, phenobarbital, secobarbita), and non-benzodiazepines (such as zolpidem and zaleplon), as well as the benzodiazepine antagonists (such as flumazenil). Other sedative-hypnotic drugs appear to work through non-GABA-ergic mechanisms such as through interaction with serotonin and dopaminergic receptors, and include buspirone, isapirone, gepirone, and tandospirone. Older drugs work through mechanisms that are not clearly elucidated, and include chloral hydrate, ethchlorvynol, meprobamate, and paraldehyde.

In some embodiments, sedative-hypnotic drugs that interact with the GABA receptor, such as benzodiazepines and non-benzodiazepines, are further classified as to which subunit or subunits of the GABAA receptor that they interact with, e.g., the $\alpha$ (which is further classified into six subtypes, including $\alpha$-1, 2, 3, and 5), $\beta$ (further classified as four different types), $\gamma$ (three different types), $\delta$, $\epsilon$, $\pi$, $\rho$, etc. Such a classification can allow further refinement of associations between genetic variation and responsiveness to a given sedative-hypnotic that interacts with a particular subclass, and predictions for a new sedative-hypnotic that interacts with the same subclass of receptors.

Opioid analgesics and antagonists act on the opioid receptor. The majority of currently available opioid analgesics act primarily at the $\mu$ opioid receptor. However, interactions also occur with the $\delta$ and $\kappa$ receptors. Similar to the sedative-hypnotics, in some embodiments opioid analgesics are further classed as to subtypes of receptors at which they primarily interact, thus allowing further refinement of the association between drug response and genetic variation, and higher predictability for a new drug, based on which receptor(s) it interacts with. Opioid analgesics include alfentanil, buprenorphine, butorphanol, codeine, dezocine, fentanyl, hydromorphone, levomethadyl acetate, levorphanol, meperidine, methadone, morphine sulfate, nalbuphine, oxycodone, oxymorphone, pentazocine, propoxyphene, remifentanil, sufentanil, tramadol; analgesic combinations such as codeine/acetaminophen, codeine/aspirin, hydrocodone/acetaminophen, hydrocodone/ibuprofen, oxycodone/acetaminophen, oxycodone/aspirin, propoxyphene/aspirin or acetaminophen. Opioid antagonists include nalmefene, naloxone, naltrexone. Antitussives include codeine, dextromethorphan.

Nonsteroidal anti-inflammatory drugs act primarily through inhibition of the synthesis of prostaglandins, e.g., through inhibition of COX-1, COX-2, or both. Older NSAIDS (e.g., salicylates) tend to be non-selective as to the type of COX inhibited, whereas newer drugs are quite selective (e.g., the COX-2 inhibitors). Non-selective COX inhibitors include aspirin, acetylsalicylic acid, choline salicylate, diclofenac, etodolac, fenoprofen, flurbiprofen, ibuprofen, indomethacin, ketoprofen, ketorolac, magnesium salicylate, meclofenamate, mefenamic acid, nabumetone, naproxen, oxaprozin, phenylbutazone, piroxicam, salsalate, salicylsalicylic acid, sodium salicylate, sodium thiosalicylate, sulindac, tenoxicam, tiaproven, azapropazone, carprofen, and tolmetin. Selective COX-2 inhibitors include celecoxib, etoricoxib, meloxicam, rofecoxib, and valdecoxib.

Histamine agonists and antagonists are classified according to receptor subtype. H1 agonists or partial agonists include 2-(m-fluorophenyl)-histamine and antagonists include chlorpheniramine, scopolamine, mepyramine, terfenadine, astemizole, and triprolidine; further antagonists (which may be further classified by their chemical structures) include the ethanolamines carbinoxamine, dimenhydrinate, diphenhydramine, and doxylamine; the ethylaminediamines pyrilamine and tripelennamine; the piperazine derivatives dydroxyzine, cyclizine, fexofenadine and meclizine; the alkylamines brompheniramine and chlorpheniramine; and miscellaneous antagonists cyproheptadine, loratadine, cetrizine. H2 agonists include dimaprit, impromidine, and amthamine; and antagonists (useful in the treatment of gastric acid secretion) include cimetidine, ranitidine, nizatidine, and famotidine; H3 agonists include R-alpha-methylhistamine, imetit, and immepip and antagonists include thioperamide, iodophenpropit, and clobenpropit; and H4 agonists include clobenpropit, imetit, and clozapine and antagonists include thioperamide. Available preparations include the H1 blockers azelastine, brompheniramine, buclizine, carbinoxamine, cetrizine, chlorpheniramine, clemastine, cyclizine, cyproheptadine, desloratidine, dimenhydrinate, diphenhydramine, emedastine, fexofenadine, hydroxyzine, ketotifen, levocabastine, loratadine, meclizine, olopatadine, phenindamine, and promoathazine.

Drugs used in asthma include sympatheticomimetics (used as "relievers," or bronchodilators) such as albuterol, albuterol/lpratropium, bitolterol, ephedrine, epinephrine, formoterol, isoetharine, isoproterenol, levalbuterol, metaproterenol, pirbuterol, salmeterol, salmeterol/fluticasone, terbutaline; aerosol corticosteroids (used as "controllers," or antiinflammatory agents) such as beclomethasone, budesonide, flunisolide, fluticasone, fluticasone/salmeterol, triamcinolone; leukotriene inhibitors such as montelukast, zafirlukast, zileuton; cormolyn sodium and nedocromil sodium; methylxanthines such as aminophylline, theophyllinem dyphylline, oxtriphylline, pentoxifylline; antimuscarinic drugs such as ipratropium; and antibodies such as omalizumab.

Erectile dysfunction drugs include cGMP enhancers such as sildenafil (Viagra), tadalafil, vardenafil, and alprostadil, and dopamine releasers such as apomorphine Drugs used in the treatment of gastrointestinal disease act by a number of mechanisms. Drugs that counteract acidity (antacids) include aluminum hydroxide gel, calcium carbonate, combination aluminum hydroxide and magnesium hydroxide preparation. Drugs that act as proton pump inhibitors include esomeprazole, lansoprazole, pantoprazole, and rabeprazole. H2 histamine blockers include cimetidine, famotidine, nizatidine, ranitidine. Anticholinergic drugs include atropine, belladonna alkaloids tincture, dicyclomine, glycopyrrolate, I hyoscyamine, methscopolamine, propantheline, scopolamine, tridihexethyl. Mucosal protective agents include misoprostol, sucralfate. Digestive enzymes include pancrelipase. Drugs for motility disorders and antiemetics include alosetron, cisapride, dolasetron, dronabinol, granisetron, metoclopramide, ondansetron, prochlorperazine, tegaserod. Antiinflammatory drugs used in gastrointestinal disease include balsalazide, budesonide, hydrocortisone, mesalamine, methylprednisone, olsalazine, sulfasalazine, infliximab. Antidiarrheal drugs include bismuth subsalicylate, difenoxin, diphenoxylate, kaolin/pectin, loperamide. Laxative drugs include bisacodyl, cascara sagrada, castor oil, docusate, glycerin liquid, lactulose, magnesium hydroxide [milk of magnesia, Epson Salt], methylcellulose, mineral oil, polycarbophpil, polyethylene glycol electrolyte solution, psyllium, sienna. Drugs that dissolve gallstones include monoctanoin, ursodiol.

Cholinoceptor-activating drugs, which act by activating muscarinic and/or nicotinic receptors include esters of choline (e.g., acetylcholine, metacholine, carbamic acid, carbachol, and bethanechol) and alkaloids (e.g., muscarine, pilocarpine, lobeline, and nicotine); cholinesterase-inhibiting drugs which typically act on the active site of cholinesterase include alcohols bearing a quaternary ammonium group (e.g., edrophonium), carbamates and related agents (e.g., neostigmine, physostigmine, pyridostigmine, ambenonium, and demercarium), and organic derivatives of phosphoric acid (e.g., echothiophate, soman, parthion, malathion); cholinoreceptor-blocking drugs typically act as antagonists to nicotinic receptors (further classified as ganglion-blockers, such as hexamethonium, mecmylamine, teteraethylammonium, and trimethaphan; and neuromuscular junction blockers, see skeletal muscle relaxants) or antagonists to muscarinic receptors (e.g. atropine, propantheline, glycopyrrolate, pirenzepine, dicyclomine, tropicamide, ipatropium, banztropine, gallamine, methooctramine, AF-DX 116, telenzipine, trihexyphenidyl, darifenacin, scopolamine, homatropine, cyclopentolate, anisotropine, clidinium, isopropamide, mepenzolate, methscopolamine, oxyphenonium, propantheline, oxybutynin, oxyphencyclimine, propiverine, tolterodine, tridihexethyl), which can be further subclassed as to which muscarinic receptor is the primary site of the effect, e.g., M1, M2, M3, M4, or M5, allowing greater predictability for an association between a genetic variation and a response for a new drug based on its primary site of effect. Available preparations of antimuscarinic drugs include but are not limited to atropine; beladonna alkaloids, extract, or tincture; clidinium; cyclopentolate; dicyclomine; flavoxate; glycopyrrolate; homatropine; 1-hysocyamine; ipratropium; mepenzolate; methantheline; methscopolamine; oxybtynin; prpantehline; scopolamine; tolterodine; tridihexethyl; tropicamide. Available preparations of ganglion blockers include mecamylamine and trimethaphan. Available cholinesterase regenerators include pralidoxime.

Adrenoceptor-activating drugs and other sympathomimetic drugs may be classified according to the receptor or receptors that they activate, e.g., alpha-one type (including subtypes A, B, D), alpha-two type (including subtypes A, B, and C), beta type (including subtypes 1, 2, and 3), and dopamine type (including subtypes 1, 2, 3, 4, and 5. Exemplary drugs include epinephrine, norepinephrine, phenylephrine, methoxamine, milodrine, ephedrine, xylometazoline, amphetamine, methamphetamine, phenmetrazine, methylphenidate, phenylpropanolamine, methylnorepinephrine, dobutamine, clonidine, BHT920, oxymetazoline, isoproterenol, procaterol, terbutaline, metaproterenol, albuterol, ritodrine, BRL37344, dopamine, fenoldopam, bromocriptine, quinpirol, dexmedetomidine, tyramine, cocaine (dopamine reuptake inhibitor), apraclonidine, brimonidine, ritodrine, terbutaline, and modafinil. Available preparations include amphetamine, apraclonidine, brimonidine, dexmedetomidine, dexmthylphenidate, dextroamphetamine, dipivefrin, dobutamine, dopamine, ephedrine, epinephrine, fenoldopam, hydroxyamphetamine, isoproterenol, mephentermine, metaraminol, methamphetamine, methoxamine, methylphenidate, midodrine, modafinil, naphazoline, norepinephrine, oxymetzoline, pemoine, phendimetrazine, phenylephrine, pseudoephedrine, tetrahydrozoline, and xylometaoline.

Adrenoceptor antagonist drugs may be classified by receptor Type In the same manner as adrenoceptor agonists, and include tolazoline, dibenamine, prazosin, terazosin, doxazosin, phenoxybenzamine, phentolamine, rauwoscine, yohimbine, labetalol, carvedilol, metoprololol, acebutolol, alprenolol, atenolol, betaxolol, celiprolol, esmolol, propanolol, carteolol, penbutolol, pindolol, timolol, butoxamine, ergotamine, dihydroergotamine, tamulosin, alfuzosin, indoramin, urapidil, bisoprolol, nadolol, sotalol, oxpenolol, bopindolol, medroxalol, and bucindolol. Available preparations include: alpha blockers doxazosin, phenoxybenzamine, phentolamine, prazosin, tamsulosin, terazosin, and tolazoline; and beta blockers acebutolol, atenolol, betaxolol, bisoprolol, carteolol, carvedilol, esmolol, labetolol, levobunolol, metiproanolol, nadolol, penbutolol, pinolol, propanolol, sotalol, timolol; and synthesis inhibitor metyrosine.

Antihypertensive agents include drugs that work by a variety of mechanisms and thus overlap with other classifications. Agents can include diuretics such as thiazide diuretics, and potassium sparing diurietcs; drugs that act on the central nervous system such as methyldopa and clonidine; ganglion-blocking drugs, suprea; adrenergic neuron-blocking agents such as gunethidine, gunadrel, bethanidine, debrisoquin, and reserpine; adrenoceptor antagonists such as propanolol, metoprolol, nadolol, carteolol, atenolol, betaxolol, bisoprolol, pindolol, acebutolol, and penbutolol, labetalol, carvedilol, esmolol, pazosin, phentolamine and phenoxybenzamine; vasodilators such as hydralzaine, minoxidil, sodium nitroprusside, diazoxide, fenoldopam, and calcium channel blockers (e.g., verapamil, diltiazem, amlopidine, felopidine, isradipine, nicardipine, nifedipine, and nisoldipine); ACE-inhibitors such as captropril, enalapril, lisinopril, benazepril, fosinopril, moexipril, perindopril, quinapril, ramipril, and trandolapril; angiotensin receptor blocking agents such as losartan, valsartan, candesartan, eprosartan, irbesartan, and telmisartan. Preparations available include: beta adrenoceptor blockers acebutolol, atenolol, betaxolol, bisoprolol, carteolol, carvedilol, exmolol, labetalol, metoprolol, nadolol, penbutolol, pindolol, propanolol, timolol; centrally acting sympathoplegic drugs clonidine, gunabenz, guanfacine, methyldopa; postganglionic sympathetic nerve terminal blockers gunadrel, guanethidine, and reserpine; alpha one selective adrenoceptor blockers doxazosin, prazosin, terazosin; ganglion-blocking agent mecamylamine; vasodilators diazoxide, fenoldopam, hydralazine, minoxidil, nitroprusside; calcium channel blockers amlodipine, diltiazem, felodipine, isradipine, nicardipine, nisoldipine, nifedipine, verapamil; ACE inhibitors benazepril, captopril, enalapril, fosinopril, lisinopril, moexipril, perindopril, quinapril, ramipril, and trandolapril; and angiotensin receptor blockers candesartan, eprosartan, irbeartan, losartan, olmisartan, telmisartan, and valsartan.

Vasodilators used in angina pectoris include nitric oxide releasing drugs such as nitric and nitrous acid esters of polyalcohols such as nitroglycerin, isorbide dinitrate, amyl nitrite, and isosorbide mononitrate; calcium channel blockers such as amlodipine, felodipine, isradipine, nicardipine, nifedipine, nimodipine, nisoldipine, nitrendipine, bepridil, diltiazem, and verapamil; and beta-adrenoceptor-blocking drugs (see above). Available preparations include: nitrates and nitrites amyl nitrite, isosorbide dinitrate, isosorbide mononitrate, nitroglycerin; calcium channel blockers amlodipine bepridil, diltiazem, felodipine, isradipine, nicardipine, nifedipine, nimodipine, nisoldipine, and verapamil; and beta blockers acebutolol, atenolol, betaxolol, bisoprolol, carteolol, carvedilol, esmolol, labetolol, levobunolol, metiproanolol, nadolol, penbutolol, pinolol, propanolol, sotalol, timolol.

Drugs used in heart failure include cardiac glycosides such as digoxin; phosphodiesterase inhibitors such as inmrinone and milrinone; beta adrenoceptor stimulant such as those described; diuretics as discussed below; ACE inhibitors such as those discussed above; drugs that inhibit both ACE and neutral endopeptidase such as omaprtrilat; vasodilators such as synthetic brain natriuretic peptide (nesiritide) and bosentan; beta adrenoceptor blockers such as those described above. Available preparations include: digitalis digoxin; digitalis antibody digoxin immune Fab; sympathomimetics dobutamine and dopamine; ACE inhibitors captopril, enalapril, fosinopril, lisinopril, quinapril, ramipril, and trandolapril; angiotensin receptor blockers candesartan, wprosartan, irbesartan, losartan, olmesartan, telmisartan, and valsartan; beta blockers bisoprolol, carvedilol, and metoprolol.

Cardiac arrhythmia drugs include drugs that act by blocking sodium channels such as quinidine, amiodaron, disoprymide, flecainide, lidocaine, mexiletine, morcizine, procainamide, propafeneone, and tocainide; beta-adrenoceptor-blocking drugs such as propanolol, esmolol, and sotalol; drugs that prolong the effective refractory period by prolonging the action potential such as amiodarone, bretylium, sotalol, dofetilide, and ibutilide; calcium channel blockers such as verapamil, diltizem, and bepridil; and miscellaneous agents such as adenosine, digitalis, magnesium, and potassium. Available preparations include: the sodium channel blockers disopryamide, flecainide, lidocaine, miexiletine, moricizine, procainamide, propafenone, quinidine sulfate, quinidine gluconate, and quinidine polygalacturonate; the beta blockers acebutolol, esmolol, and propranolol; the action potential-prolonging agents amiodarone, bretylium, dofetilide, ibutilide, and sotalol; the calcium channel blockers bepridil, diltiazem, and verapamil; and adenosine and magnesium sulfate.

Diuretic agents include drugs that act as carbonic anhydrase inhibitors such as acetazoloamide, dichlorphenamide, methazolamide; loop diuretics such as furosemide, bumetanide, torsemide, ethacrynic acid, and mercurial diuretics; drugs that inhibit NaCl transport in the distal convoluted tubule and, in some cases, also act as carbonic anhydrase inhibitors, such as bendroflumethiazide, benzthiazide, chlorothiazide, chlorthalidone, hydrochlorothiazide, hydroflumethiazide, indapamide, methyclothiazide, metolazone, polythiazide, quinethazone, and trichlormethazide; potassium-sparing diuretics such as spironolactone, triamterene, eplerenone, and amiloride; osmotic diuretics such as mannitol; antidiuretic hormone agonists such as vasopressin and desmopressin; antidiuretic hormone antagonists such aslithium and demeclocycline. Available preparations include actetazolamide, amiloride, bendroflumethiazide, benzthiazide, brinzolamide, bumetanide, chlorothiazide, chlorthalidone, demeclocycline, dichlorphenamide, dorzolamide, eplerenone, ethacrynic acid, furosemide, hydrochlorothiazide, hydroflumethiazide, indapamide, mannitol, methazolamide, methyclothiazide, metolazone, polythiazide, quinethazone, apironolactone, torsemide, triamterene, and trichlormethazide.

Serotonin and drugs that affect serotonin include serotonin agonists such as fenfluramine and dexfenfluramine, buspirone, sumatriptan, cisapride, tegaserod; seratonin antagonists p-chlorophenylalanine and p-chloroamphetamine, and reserpine; and the serotonin receptor antagonists phenoxybenzamine, cyproheptadine, ketanserin, ritanserin, and ondansetron; serotonin reuptake inhibitors are described elsewhere herein. Serotonin receptor agonists include almotriptan, eletriptan, frovatriptan, naratriptan, rizatriptan, sumatriptan, and zolmitriptan.

Ergot alkaloids are useful in the treatment of, e.g., migraine headache, and act on a variety of targets, including alpha adrenoreceptors, serotonin receptors, and dopamine receptors. They include bromocriptine, cabergoline, pergolide, ergonovine, ergotamine, lysergic acid diethylamide, and methysergide. Available preparations include dihydroergotamine, ergonovine, ergotamine, ergotamine tartrate, and methylergonovine.

Vasoactive Peptides include aprepitant, bosentan.

Eicosanoids include prostaglandins, thomboxanes, and leukotrienes. Eicosanoid modulator drugs include alprostadil, bimatoprost, carboprost tromethamine, dinoprostone, epoprostenol, latanoprost, misoprostol, monteleukast, travaprost, treprostinil, unoprostone, zafirleukast, zileuton. Further eicosanoid modulators are discussed elsewhere herein as nonsteroidal antiinflammatory drugs (NSAIDs)

Drugs for the treatment of acute alcohol withdrawal include diazepam, lorazepam, oxazepam, thiamine; drugs for prevention of alcohol abuse include disulfiram, naltrexone; and drugs for the treatment of acute methanol or ethylene glycol poisoning include ethanol, fomepizole.

Antiseizure drugs include carbamazepine, clonazepam, clorazepate dipotassium, diazepam, ethosuximide, ethotoin, felbamate, fosphenyloin, gabapentin, lamotrigine, levetiracetam, lorazepam, mephenyloin, mephobarbital, oxycarbazepine, pentobarbital sodium, phenobarbital, phenyloin, primidone, tiagabine, topiramate, trimethadione, valproic acid.

General anesthetics include desflurane, dexmedetomidine, diazepam, droperidol, enflurane, etomidate, halothane, isoflurane, ketamine, lorazepam, methohexital, methoxyflurane, midazolam, nitrous oxide, propofol, sevoflurane, thiopental.

Local anesthetics include articaine, benzocaine, bupivacaine, butamben picrate, chloroprocaine, cocaine, dibucaine, dyclonine, levobupivacaine, lidocaine, lidocaine and etidocaine eutectic mixture, mepivacaine, pramoxine, prilocalne, procaine, proparacaine, ropivacaine, tetracaine.

Skeletal muscle relaxants include neuromuscular blocking drugs such as atracurium, cisatracurium, doxacurium, metocurine, mivacurium, pancuronium, pipecuronium, rocuronium, succinylcholine, tubocurarine, vecuronium; muscle relaxants (spasmolytics) such as baclofen, botulinum toxin type A, botulinum toxin type B, carisoprodol, chorphenesin, chlorzoxazone, cyclobenzaprine, dantrolene, diazepam, gabapentin, metaxalone, methocarbamol, orphenadrine, riluzole, and tizanidine.

Antipsychotic agents include aripiprazole, chlorpromazine, clozapine, fluphenazine, fluphenazine esters, haloperidol, haloperidol ester, loxapine, mesoridazine, molindone, olanzapine, perphenazine, pimozide, prochlorperazine, promazine, quetiapine, risperidone, thioridazine, thiothixene, trifluoperazine, triflupromazine, ziprasidone; mood stabilizers include carbamazepine, divalproex, lithium carbonate, and valproic acid.

Agents used in anemias include hematopoietic growth factors such as darbopoetin alfa, deferoxamine, epoetin alfa (erythropoetin, epo), filgrastim (G-CSF), folic acid, iron, oprelvekin (interleukin 11), pegfilgrastim, sargramostim (GM-CSF), vitamin B12.

Disease-modifying antirheumatic drugs include anakinra, adalimumab, auranofin, aurothioglucose, etanercept, gold sodium thiomalate, hydroxychloroquine, infliximab, leflunomide, methotrexate, penicillamine, sulfasalazine. Drugs used in gout include allopurinol, colchicine, probenecid, sulfinpyrazone.

Drugs used in disorders of coagulation include abciximab, alteplase recombinant, aminocaproic acid, anisindione, antihemophilic factor [factor VIII, AHF], anti-inhibitor coagulant complex, antithrombin III, aprotinin, argatroban, bivalirudin, cilostazol, clopidogrel, coagulation factor VIIa recombinant, dalteparin, danaparoid, dipyridamole, enoxaparin, eptifibatide, Factor VIIa, Factor VIII, Factor IX, fondaparinux, heparin sodium, lepirudin, phytonadione [K1], protamine, reteplase, streptokinase, tenecteplase, ticlopidine, tinzaparin, tirofiban, tranexamic acid, urokinase, warfarin.

Hypothalamic and pituitary hormones include bromocriptine, cabergoline, cetrorelix, chorionic gonadotropin [hCG], corticorelin ovine, corticotropin, cosyntropin, desmopressin, follitropin alfa, follitropen beta [FSH], ganirelix, gonadorelin acetate [GnRH], gonadorelin hydrochloride [GnRH], goserelin acetate, histrelin, leuprolide, menotropins [hMG], nafarelin, octreotide, oxytocin, pergolide, protirelin, sermorelin, somatrem, somatropin, thyrotropin alpha, triptorelin, urofollitropin, vasopressin.

Thyroid and antithyroid drugs include the thyroid agents: levothyroxine [T4], liothyronine [T3], liotrix [a 4:1 ratio of T4:T3], thyroid desiccated [USP]; and the antithyroid agents: diatrizoate sodium, iodide, iopanoic acid, ipodate sodium, methimazole, potassium iodide, propylthiouracil [PTU], thyrotropin; recombinant human TSH.

Adrenocorticosteroids and adrenocortical antagonists include the glucocorticoids for oral and parenteral use: betamethasone, betamethasone sodium phosphate, cortisone, dexamethasone, dexamethasone acetate, dexamethasone sodium phosphate, hydrocortisone [cortisol], hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, triamcinolone diacetate, triamcinolone hexacetonide. Another class of adrenocorticoids are the mineralocorticoids, e.g., fludrocortisone acetate. The adrenal steroid antagonists include aminoglutethimide, ketoconazole, mitotane.

Gonadal hormones and inhibitors include the estrogens:: conjugated estrogens, dienestrol, diethylstilbestrol diphosphate, esterified estrogens, estradiol cypionate in oil, estradiol, estradiol transdermal, estradiol valerate in oil, estrone aqueous suspension, estropipate, ethinyl estradiol; the progestins: hydroxyprogesterone caproate, levonorgestrel, medroxyprogesterone acetate, megestrol acetate, norethindrone acetate, norgestrel, progesterone; the androgens and the anabolic steroids: methyltestosterone, nandrolone decanoate, oxandrolone, oxymetholone, stanozolol, testolactone, testosterone aqueous, testosterone cypionate in oil, testosterone enanthate in oil, testosterone propionate in oil, testosterone transdermal system, testosterone pellets. Drugs may further be classed as antagonists and inhibitors of gonadal hormones: anastrozole, bicalutamide, clomiphene, danazol, dutasteride, exemestane, finasteride, flutamide, fulvestrant, letrozole mifepristone, nilutamide, raloxifene, tamoxifen, and toremifene.

Agents that affect bone mineral homeostasis include Vitamin E, its metabolites and analogs: calcifediol, calcitriol, cholecalciferol [D3], dihydrotachysterol [DHT], doxercalciferol, ergocalciferol [D2], and paricalcitol; calcium: calcium acetate [25% calcium], calcium carbonate [40% calcium], calcium chloride [27% calcium], calcium citrate [21% calcium], calcium glubionate [6.5% calcium]; calcium gluceptate [8% calcium], calcium gluconate [9% calcium], calcium lactate [13% calcium], and tricalcium phosphate [39% calcium]; phosphate and phosphate binders such as phosphate and sevelamer; and other drugs such as alendronate, calcitonin-salmon, etidronate, gallium nitrate, pamidronate, plicamycin, risedronate, sodium fluoride, teriparatide, tiludronate, zoledronic acid.

Beta-lactam antibiotics and other inhibitors of cell wall synthesis include the penicillins, such as amoxicillin, amoxicillin/potassium clavulanate, ampicillin, ampicillin/sulbactam sodium, carbenicillin, dicloxacillin, mezlocillin, nafcillin, oxacillin, penicillin G benzathine, penicillin G procaine, penicillin V, piperacillin, pipercillin and tazobactam sodium, ticarcillin, and ticarcillin/clavulanate potassium; the cephalosporins and other beta-lactam drugs, such as the narrow spectrum (first generation) cephalosporins, e.g., cefadroxil, cefazolin, cephalexin, cephalothin, cephapirin, and cephradine; the second generation (intermediate spectrum) cephalosporins, e.g., cefaclor, cefamandole, cefinetazole, cefonicid, cefotetan, cefoxitin, cefprozil, cefuroxime, and loracarbef; the broad spectrum (third- and fourth-generation cephalosporins, e.g., cefdinir, cefditoren, cefepime, cefixime, cefoperazone, cefotaxime, cefpodoxime proxetil, ceftazidime, ceftibuten, ceftizoxime, and ceftriaxone. Further classes include the carbapenem and monobactam, e.g., aztreonam, ertapenem, imipenem/cilastatin, and meropenem; and other drugs such as cycloserine (seromycin pulvules), fosfomycin, vancomycin.

Other antibiotics include chloramphenicol, the tetracyclines, e.g., demeclocycline, doxycycline, methacycline, minocycline, oxtetracycline, and tetracycline; the macrolides, e.g., azithromycin, clarithromycin, erythromycin; the ketolides, e.g., telithromycin; the lincomycins, e.g., clindamycin; the streptogramins, e.g., quinupristin and dalfopristin; and the oxazolidones, e.g., linezolid.

Aminoglycosides and spectinomycin antibiotics include amikacin, gentamicin, kanamycin, neomycin, netilmicin, paromomycin, spectinomycin, streptomycin, and tobramycin.

Sulfonamides, trimethoprim, and quinolone antibiotics include the general-purpose sulfonamides, e.g., sulfadiazine, sulfamethizole, sulfamethoxazole, sulfanilamide, and sulfisoxazole; the sulfonamides for special applications, e.g., mafenide, silver sulfadiazine, sulfacetamide sodium. Trimethoprims include trimethoprim, trimethoprim-sulfamethoxazole [co-trimoxazole, TMP-SMZ]; the quinolones and fluoroquinolones include cinoxacin, ciprofloxacin, enoxacin, gatifloxacin, levofloxacin, lomefloxacin, moxifloxacin, nalidixic acid, norfloxacin, ofloxacin, sparfloxacin, and trovafloxacin.

Antimycobacterial drugs include drugs used in tuberculosis, e.g., aminosalicylate sodium, capreomycin, cycloserine, ethambutol, ethionamide, isoniazid, pyrazinamide, rifabutin, rifampin, rifapentine, and streptomycin; and drugs used in leprosy, e.g., clofazimine, dapsone.

Antifungal agents include amphotericin B, butaconazole, butenafine, caspofungin, clotrimazole, econazole, fluconazole, flucytosine, griseofulvin, itraconazole, ketoconazole, miconazole, naftifine, natamycin, nystatin, oxiconazole, sulconazole, terbinafine, terconazole, tioconazole, tolnaftate, and voriconazole.

Antiviral agents include abacavir, acyclovir, adefovir, amantadine, amprenavir, cidofovir, delavirdine, didanosine, efavirenz, enfuvirtide, famciclovir, fomivirsen, foscamet, ganciclovir, idoxuridine, imiquimod, indinavir, interferon alfa-2a, interferon alpha-2b, interferon-2b, interferon alfa-n3, interferon alfacon-1, lamivudine, lopinavir/ritonavir, nelfinavir, nevirapine, oseltamivir, palivizumab, peginterferon alfa-2a, peginterferon alfa-2b, penciclovir, ribavirin, rimantadine, ritonavir, saquinavir, stavudine, tenofovir, trifluridine, valacyclovir, valgancyclovir, zalcitabine, zanamivir, and zidovudine.

Further antimicrobial agents, disinfectants, antiseptics, and sterilants include the miscellaneous antimicrobial agents, e.g., methenamine hippurate, methenamine mandelate, metronidazole, mupirocin, nitrofurantoin, polymyxin B; and the disinfectants, antiseptics, and sterilants, e.g., benzalkonium, benzoyl peroxide, chlorhexidine gluconate, glutaraldehyde, hexachlorophene, iodine aqueous, iodine tincture, nitrofurazone, oxychlorosene sodium, providone-iodine, sliver nitrate, and thimerosal.

Antiprotozoal drugs include albendazole, atovaquone, atovaquone-proguanil, chloroquine, clindamycin, doxycycline, dehydroemetine, eflomithine, halofantrine, iodoquinol, mefloquine, melarsoprol, metronidazole, nifurtimox, nitazoxanide, paromomycin, pentamidine, primaquine, pyrimethamine, quinidine gluconate, quinine, sodium stibogluconate, sulfadoxine and pyrimethamine, and suramin.

Anthelmintic drugs include albendazole, bithionol, diethylcarbamazine, ivermectin, levamisole, mebendazole, metrifonate, niclosamide, oxamniquine, oxantel pamoate, piperazine, praziquantel, pyrantel pamoate, suramin, thiabendazole.

Immunopharmacological agents include abciximab, adalimumab, alefacept, alemtuzumab, anti-thymocyte globulin, azathioprine, basiliximab, BCG, cyclophosphamide, cyclosporine, daclizumab, etanercept, gemtuzumab, glatiramer, ibritumomab tiuxetan, immune globulin intravenous, infliximab, interferon alfa-2a, interferon alfa 2b, interferon beta-1a, interferon beta-1b, interferon gamma-1b, interleukin-2, IL-2, aldesleukin, leflunomide, levamisole, lymphocyte immune globulin, methylprednisolone sodium succinate, muromonab-CD3 [OKT3], mycophenolate mofetil, pegademase bovine, peginterferon alfa-2a, peginterferon alfa-2b, prednisone, RHo(D) immune globulin micro-dose, rituximab, sirolimus, tacrolimus [FK506], thalidomide, and trastuzumab.

Heavy metal chelators include deferoxamine, dimercaprol, edetate calcium [calcium EDTA], penicillamine, succimer, and unithiol.

b. Structural Classes of Drugs

In another example of drug classification embodiments, a drug may be classified according to its structural class or family; certain drugs may fall into more than one structural class or family. Thus, in some embodiments, drugs are classified according to structure. Drugs that have a common action may have different structures, and often one of the best predictors of a drugs likely action is its structure. By way of example only, certain classes of drugs may be further organized by chemical structure classes presented herein. One non-limiting example is antibiotics. Table 9, below, presents non-limiting examples of antibiotics further classified by illustrative chemical structure classes.

TABLE 9

Structural Classes of Antibiotic Drugs

| Structure Class | Examples of Antibiotics within Structure Class |
|---|---|
| Amino Acid Derivatives | Azaserine, Bestatin, Cycloserine, 6-diazo-5-oxo-L-norleucine |
| Aminoglycosides | Armastatin, Amikacin, Gentamicin, Hygromicin, Kanamycin, Streptomycin |
| Benzochinoides | Herbimycin |
| Carbapenems | Imipenem, Meropenem |
| Coumarin-glycosides | Novobiocin |

TABLE 9-continued

Structural Classes of Antibiotic Drugs

| Structure Class | Examples of Antibiotics within Structure Class |
| --- | --- |
| Fatty Acid Derivatives | Cerulenin |
| Glucosamines | 1-deoxynojirimycin |
| Glycopeptides | Bleomycin, Vancomycin |
| Imidazoles | Metroidazole |
| Penicillins | Benzylpenicillin, Benzathine penicillin, Amoxycillin, Piperacillin |
| Macrolides | Amphotericin B, Azithromycin, Erythromycin |
| Nucleosides | Cordycepin, Formycin A, Tubercidin |
| Peptides | Cyclosporin A, Echinomycin, Gramicidin |
| Peptidyl Nucleosides | Blasticidin, Nikkomycin |
| Phenicoles | Chloramphenicol, Thiamphenicol |
| Polyethers | Lasalocid A, Salinomycin |
| Quinolones | 8-quinolinol, Cinoxacin, Ofloxacin |
| Steroids | Fusidic Acid |
| Sulphonamides | Sulfamethazine, Sulfadiazine, Trimethoprim |
| Tetracyclins | Oxytetracyclin, Minocycline, Duramycin |

In some embodiments, drugs are classed as optical isomers, where a class is two or more optical isomers, or racemate, of a compound of the same chemical formula. Thus, the invention includes methods and compositions for screening individuals for a genetic variation and/or phenotypic variation that predicts responsiveness to a first drug, and using this association to determine whether or not to modulate the treatment of an individual with a second drug, where the first and second drugs are optical isomers. In some embodiments, the first drug is a racemate and the second drug is a stereoisomer that is a component of the racemate. In some embodiments the first drug is a stereoisomer and the second drug is a racemate that includes the stereoisomer. In some embodiments the first drug is a first stereoisomer and the second drug is a second stereoisomer of a compound.

In some embodiments, drugs are classed as different crystal structures of the same formula. Thus, the invention includes methods and compositions for screening individuals for a genetic variation and/or phenotypic variation that predicts responsiveness to a first drug, and using this association to determine whether or not to modulate the treatment of an individual with a second drug, where the first and second drugs are members of a class of drugs of the same chemical formula but different crystal structures.

In some embodiments, drugs are classed by structural components common to the members of the class. Thus, the invention includes methods and compositions for screening individuals for a genetic variation and/or phenotypic variation that predicts responsiveness to a first drug, and using this association to determine whether or not to modulate the treatment of an individual with a second drug, where the first and second drugs are members of a class of drugs that contain the same structural component. By way of example only, a drug may be structurally classified as an acyclic ureide; acylureide; aldehyde; amino acid analog; aminoalkyl ether (clemastine, doxylamine); aminoglycoside; anthracycline; azalide; azole; barbituate; benzodiazapene; carbamate (e.g., felbamate, meprobamate, emylcamate, phenprobamate); carbapenam; carbohydrate; carboxamide (e.g., carbamazepine, oxcarbazepine); carotenoid (e.g., lutein, zeaxanthin); cephalosporin; cryptophycin; cyclodextrin; diphenylpropylamine; expanded porphyrin (e.g., rubyrins, sapphyrins); fatty acid; glycopeptide; higher alcohol; hydantoins (e.g., phenyloin); hydroxylated anthroquinone; lincosamide; lipid; lipid related compound; macrolide; mustard; nitrofuran; nitroimidazole; non-natural nucleotide; non-natural nucleoside; oligonucleotide; organometallic compound; oxazolidinedione; penicillin; phenothiazine derivative (alimemazine, promethazine); phenylpiperidine; phthalocyanine; piperazine derivative (e.g., cetrizine, meclozine); platinum complex (e.g., cis-platin); polyene; polyketide; polypeptide; porphyrin; prostaglandin (e.g., misoprostol, enprostil); purine; pyrazolone; pyrimidine; pyrrolidine (levetiracetam); quinolone; quinone; retinoid (e.g., isotretinoin, tretinoin); salicylate; sphingolipid; steroid (e.g., prednisone, triamcinolone, hydrocortisone); substituted alkylamine (e.g., talastine, chlorphenamine); substituted ethylene diamine (mepyramine, thonzylamine); succinimide (ethosuximide, phensuximide, mesuximide); sulfa; sulfonamide (sulfathiazole, mafenide); sulfone; taxane; tetracycline (e.g., chlortetracycline, oxytetracline); texaphyrin (e.g., Xcytrin, Antrin); thiazide; thiazolidinedione; tocopherol, tocotrienol, triazine (e.g., lamotrigine); urea; xanthine (theobromine, aminophylline); and zwitterion.

EXAMPLES

Example 1

X-DNA Gel

In one aspect of the invention, the branched nucleic acids are designed comprising sequences depicted in Table 3. Without further purification, oligonucleotides (Integrated DNA technologies) were dissolved in an annealing buffer (10 mM Tris, pH=8.0, 1 mM ethylenediaminetetraacetic acid (EDTA), and 50 mM NaCl) with a final concentration of 50 mM. X-DNA was constructed by mixing four oligonucleotide components (with the same molar ratio) in sterile Milli-Q water with a final concentration of 20 mM for each oligonucleotide. Hybridizations were performed according to the following procedures: (i) Denaturation at 95° C. for 2 min. (ii) Cooling at 65° C. and incubation for 2 min. (iii) Annealing at 60° C. for 5 min. and (iv) Further annealing at 60° C. for 0.5 min with a continuous temperature decrease at a rate of 1° C. per min. The annealing steps were repeated a total of 40 times. The final annealed products were stored at 4° C. The X01 to X04 were four corresponding single oligonucleotides that formed an X-DNA. For constructing an X-DNA gel, each individual X-DNA was ligated specifically to other X-DNA in the ligation solution which contained ligase buffer, 5.04 mmol X-DNA monomer, and 30 Weiss units of T4 DNA ligase (Promega, Madison, Wis.). The mixture was gently shaken at low speed overnight at room temperature. A cylindrically shaped plastic mold was used to construct the cylinder shaped X-DNA gel.

AFM (Nanoscope III, Digital Instruments) was carried out in air using the tapping mode with rectangular cantilevers with tetrahedral tips (Olympus). Mica was chosen as a solid substrate and used immediately after cleavage in a clean atmosphere. For the sample preparation, surface modification was accomplished by a deposit of silane in distilled and deionized water (DDI water). Briefly, the fresh mica was placed in a container filled with 10 mL 3-aminopropyltriethoxysilane (APTES) solution (2% w/w) for 15 min, and then the APTES-derivatized mica was thoroughly washed with DDI water several times and dried with a gentle stream of nitrogen gas. A piece of DNA gel was loaded on the mica for 7 min, and then washed with DDI water several times and dried. For SEM imaging, strips cut from the dried DNA gel were placed into the top of the SEM holder with carbon tape and metal-coated with Au/Pd to obtain high resolution images.

Mechanical Properties.

The mechanical property measurements were performed on a Dynamic Mechanical Analyzer (DMA 2980, TA Instruments, Inc). The hydrogel was clamped between a parallel-plate compression clamp with a diameter of 1.0 cm. This test was conducted on a cylindrical shaped DNA gel with 7.0 mm in diameter and 3.0 mm in height. For tensile testing, DNA hydrogels were approximately 3.0 mm thick cast in a cylindrical mold (approximately 5 mm×5 mm).

In Vitro Degradation Assays.

A dry gel was weighed first and then transferred to a microcentrifuge tube filled with PBS, pH 7.4. The tube was slowly shaken at 37° C. Supernatants of a gel sample were removed, immediately followed by a measuring of the weight of the sample. Fresh PBS buffer solution was added to the sample and then returned to the 37° C. shaker.

Biocompatiblity

A 96-well microtiter plate was seeded with Chinese Hamster Ovarian (CHO) cells and 200 µL of growth medium in each well. The cells were incubated at 37° C. with 5% $CO_2$. The DNA gel was placed into the 96-well plate containing CHO cells one day after the cells were plated. Cell viability was evaluated 24 hours later by using CellTiter 96® AQueous Non-Radioactive Cell Proliferation Assay kits (Promega).

Fabrication of Micropatterned DNA Gel.

A DNA gel in a micro-meter scale "CORNELL" shape was made by casting it in a PDMS mold that was fabricated by photolithography (FIG. 1). The line width was 100 µm, the height 20 µm, and the size of each letter was 500×400 µm2. DNA pre-gel solution (2 µL) was dropped on an APTES modified glass slide, and a PDMS mold was put on the solution. After curing for 2 hours, the PDMS mold was peeled off. To visualize the DNA gel micro-patterns, the molded gel was stained with the DNA specific dye SYBR I, and the fluorescence image was captured by a fluorescence microscope.

A swollen, millimeter-scale DNA hydrogel is shown in FIG. 1B. To show that the hydrogel indeed contained DNA molecules, a DNA specific dye (SYBR I, Green: Ex/Em, 494 nm/520 nm) was used to stain the gel. After staining, the DNA hydrogel gave out an extremely intense green fluorescence (FIG. 1B, inset), indicating that the hydrogel was composed of DNA molecules. Similar results were also obtained with a different fluorescent, DNA-specific dye (EtBr, Red: Ex/Em, 518 nm/605 nm).

Importantly, these DNA gels can be formed into pre-selected and different shapes at macroscopic scale. FIGS. 1C and 1D demonstrate DNA hydrogels with rectangular, round, triangular, cross, star, and even "CORNELL" shapes with millimeter size (i.e., macroscopic). In addition, DNA hydrogels can also be molded into complicated shapes at microscopic scale. A micrometer-sized DNA hydrogel in the shape of "CORNELL" was fabricated using traditional photolithography combined with DNA-ligase-inked poly(dimethylsiloxane) (PDMS) printing (FIG. 1D). Interestingly, these DNA hydrogels repeatedly returned to their original shapes even after successive drying and hydrating without collapsing to films or powders (FIG. 1C).

Different swelling profiles of DNA hydrogels can be achieved by adjusting the initial concentration and the types of DNA monomers (Tables 1-Table 3): The higher the initial concentration of the DNA monomers, the higher the degree of swelling of each hydrogel. More specifically, the Y-DNA based hydrogel (Y-DNA gel), swelled more than 400% at the highest initial concentration of DNA monomers (0.2 mM); while at the lowest initial concentration (0.03 mM), it swelled only about 100%. Besides the initial concentrations, the different types of DNA monomers also influenced the degree of swelling. X-DNA based hydrogel (X-DNA gel) showed a higher swelling degree than both the Y-DNA gel and T-DNA gel; these trends in the degree of swelling among X-, Y-, and T-DNA gels were true for all the concentrations tested.

Figure 4A:
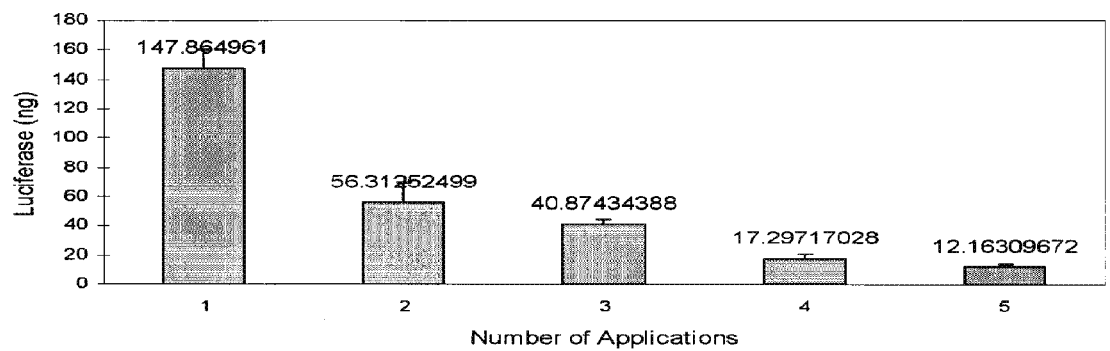
FIG. 4. (A) Reusable test for the protein producing DNA hydrogel with a *renilla* luciferase reporter gene. (B) Degradation profile for the protein producing X-DNA hydrogel in PBS solution (pH 7.4). Each point was obtained from 75 gel pads and new PBS solution was added into the DNA hydrogel samples every day after the supernatant was removed from the solution. At lease three experiments were repeatedly conducted to get an average of the values for points in the plot.
Figure 4B:
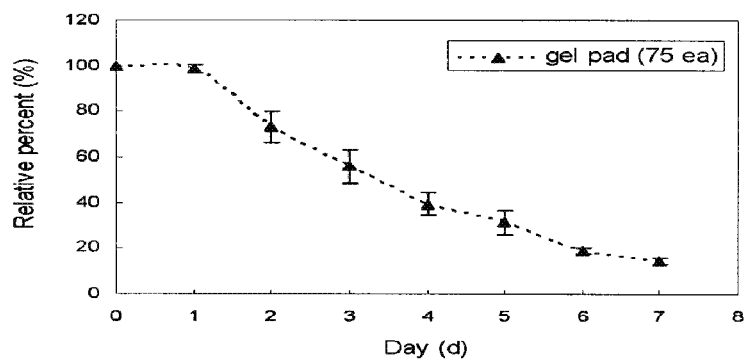
Figures 6A, 6B:
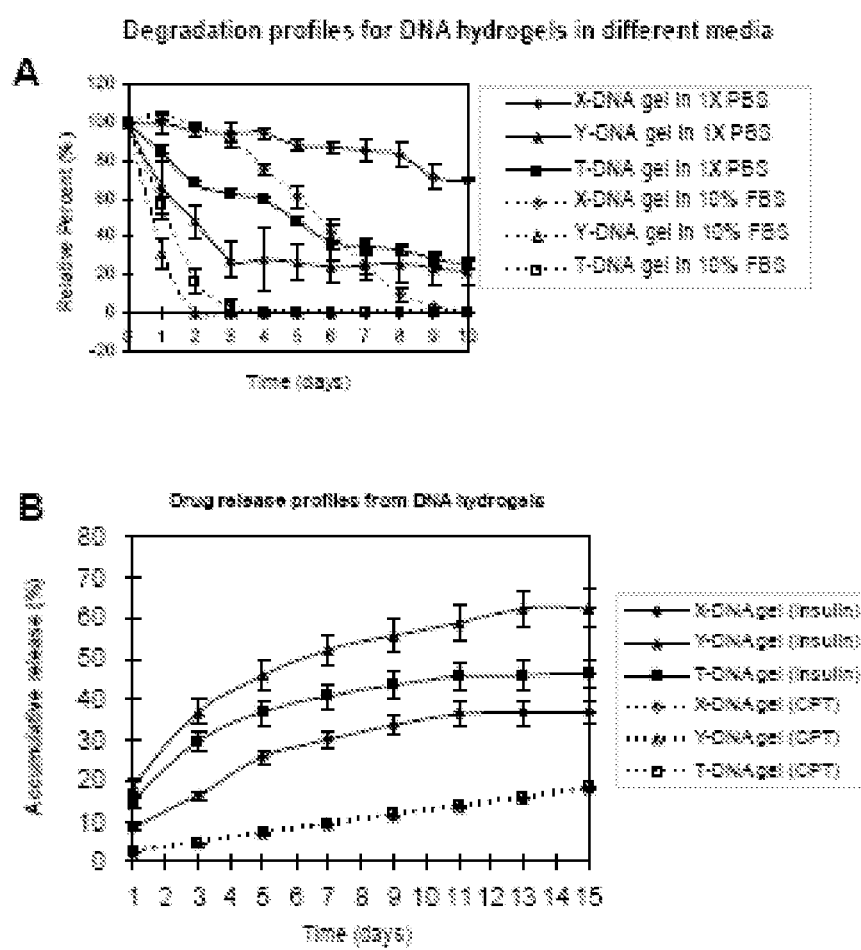
FIG. 6. DNA hydrogel degradation profiles. (A) shows the "Relative percent" refers to percentage DNA mass loss from the starting gels. (B) Drug Release profiles. CPT (Mw 348.3 Da) and porcine insulin (Mw 5777.6 Da) were encapsulated, which encapsulation occurred in situ (no post-gelation loading needed). Encapsulation was nearly 100% efficient. No burst release was detected, an relatively smooth release curves were obtained. After 12 days about 60%, 40% and 30% of the insulin was released from the Y-, T-, and X-DNA gels, respectively. A DNA monomer solution (150 μl at 23.7 μg/μl with 30 units of T4 DNA ligase) was mixed with 30 μl of the stock solution of the drug (10 mg/ml). The amount of released insulin was determined using Mercodia Porcine Insulin ELISA enzyme immunoassay kits (ALPCO Diagnostics, Salem, N.H.). The amount of released CPT was determined by UV absorbance at 370 nm (Extinction coefficient: $E^{mM}$=19.9 (370 nm), Sigma-Aldrich, Saint Louis, Mo.). (C) Degradation profile for DNA hydrogels. The hydrogels were biodegradable. Dotted lines indicated empty gels, dashed lines and solid lines indicate insulin-loaded gels and CPT-loaded gels, respectively. Symbols: x, triangles, squares indicate X-, Y-, T-DNA gels, respectively. Degradability was adjustable based on the branched DNA monomer (BDM) used and was measured by DNA mass loss. After 14 days over 70% of the X-DNA gels (both empty and loaded) still remained while 50% of insulin-loaded Y-DNA and T-DNA gels remained. Loaded gels were more resistant than empty gels. Different degradation levels were obtained based on the internal structures of the gels (e.g., BDM used, load v. no load, or presence of nucleases).
Figure 6C:
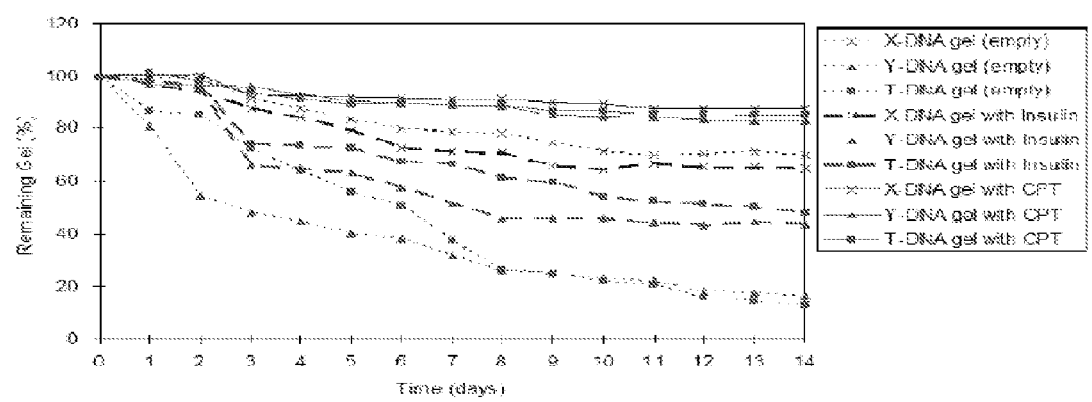
Figure 7A:
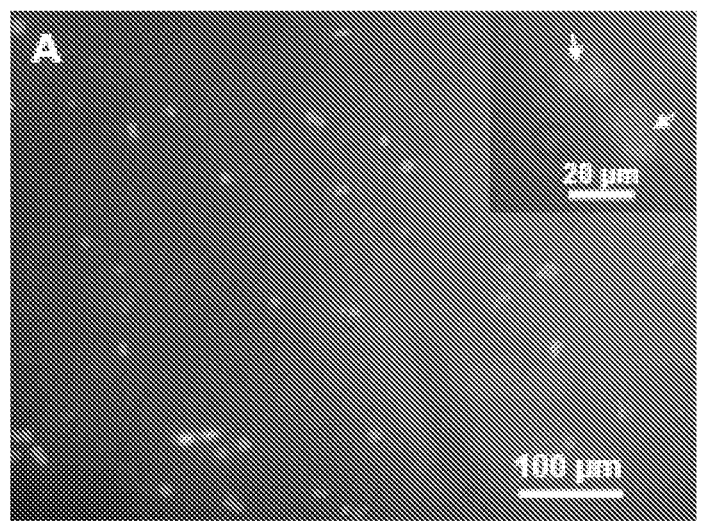
FIG. 7. Cell Encapsulation and Biocompatibility. (A): shows the Fluorescent images of the CHO cells encapsulated into an X-DNA hydrogel CellTracker™ Red CMTPX Probes (Ex/Em=577 nm/602 nm) were used for CHO cell staining, and SYBR I dye (Ex/Em=494 nm/521 nm) was used for DNA hydrogel staining (background). Inset shows mitotic cells (arrows) indicating a cell division. (B): Cytotoxicity of the DNA hydrogels on CHO cells. "Relative percent" indicates the cell survival ratio between samples and the negative control, which was CHO cells without any DNA hydrogels. Cell survival readings were obtained using CellTiter 96 Aqueous Non-Radioactive Cell Proliferation Assay (Promega, Madison, Wis.). Error bars represent standard deviation from at least 3 replicates.
Figure 7B:
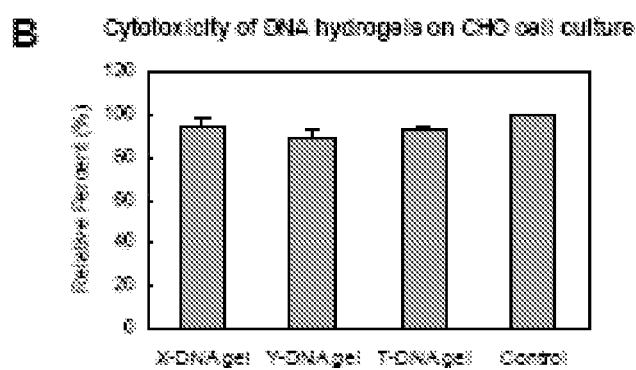
Figure 8A:
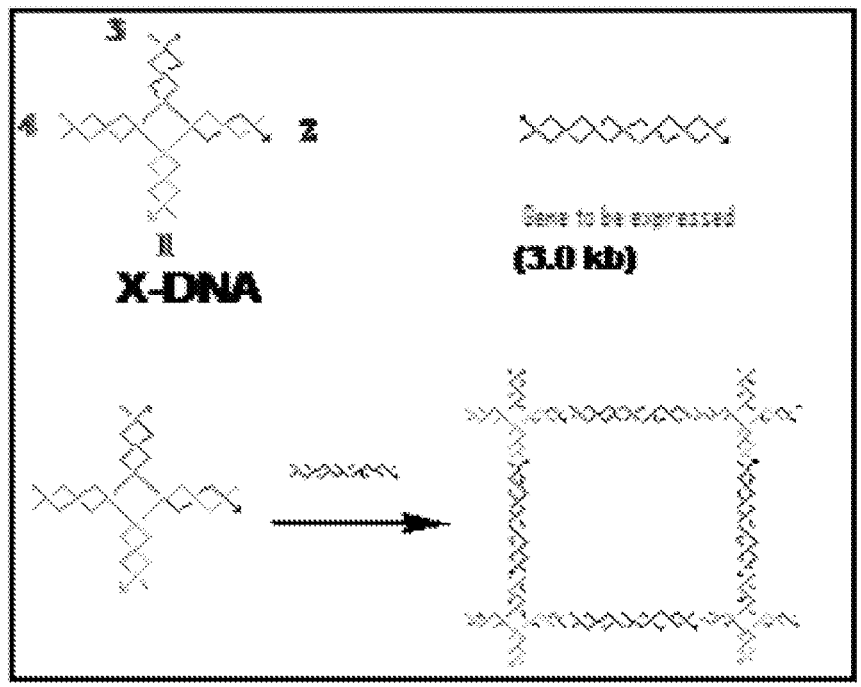
FIG. 8. (A) Shows a scheme for generating a network matrix comprising X-nucleic acids and linear nucleic acids encoding a protein of interest; (B) Shows an exemplary X-DNA (SEQ ID NOs: 53 (i.e., 5' starting with CTGA . . . ), 54 (5' starting with ACCT . . . ), 55 (5' starting with GAAT . . . ) and 56 (5' starting with TCCG . . . ).
Figure 8B:
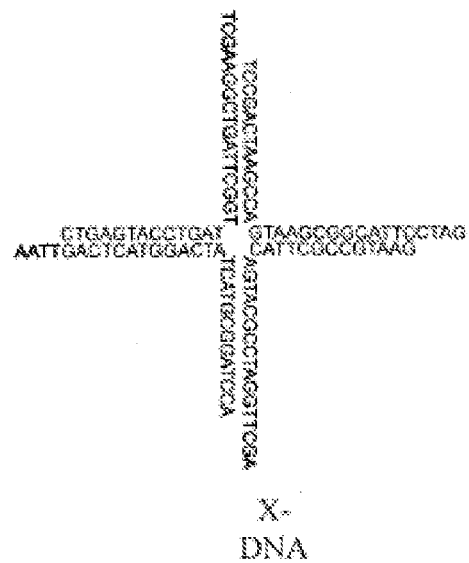
Figure 9:
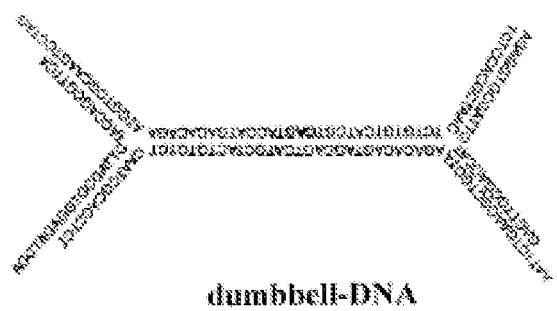
FIG. 9. Shows a dumbbell-shape DNA (SEQ ID NOs: 102, 108 and 112 form Y-shapes that are joined end-to-end).

The morphology and structure of the DNA hydrogel were further studied employing a variety of visualization methods including AFM, FE-SEM, and confocal microscopy (FIG. 4). The surface morphology and the inner structure of each DNA hydrogel in dried and swollen states showed striking differences depending on the types of DNA monomer used. In the dry state, surface morphology revealed a woven pattern for X-DNA gel, a fibrous form for Y-DNA gel, and a scale shape for T-DNA gel (FIGS. 4, A, B, C). In particular, the X-DNA gel in FIG. 4A shows that two flat DNA gel stripes were woven into a knot to form a large sheet with many wrinkles on the surface. On the other hand, the Y-DNA gel in FIG. 4B shows a fibrous form spreading out from many branches, which may have resulted from the shape of Y-DNA building blocks. The T-DNA gel in FIG. 4C shows a bundle of small thin sheets. In the swollen state, inner structures of DNA hydrogels were optically sectioned and exposed using confocal microscopy and SYBR (FIG. 4). Again, the inner structure of a DNA-hydrogel differs drastically with different types of DNA monomers: a large number of various sized pores and channels for the X-DNA gel (FIG. 4D), obvious fibers with fractal-shapes on the periphery for the Y-DNA gel (FIG. 4E), and perpendicularly erected, scale-like structures for the TDNA gel (FIG. 4F).

The more detailed inner structures of the DNA hydrogels were further evaluated using AFM at molecular resolution (FIG. 4G). It was observed that the X-DNA gel had nanoscale holes approximately 12.3±1.4 nm in the network structure. The measured hole's size is very close to the theoretically calculated and designed value (20 bps per arm, and two linked arms are 40 bps which are 13.6 nm), showing that 1) four X-DNA monomers were linked with each other to form the cross-linked, network structure of the X-DNA gel, and 2) the pore sizes can be accurately controlled. In contrast to the highly ordered network internal structure of the X-DNA gel, the Y-DNA gel and T-DNA gel showed randomly oriented structures (data not shown).

The imaging results demonstrate that the original shapes of DNA monomers have significant effect on both surface morphologies and inner structures of the final DNA hydrogels. More importantly, by selecting different shapes of DNA monomers and by adjusting the lengths of branched arms, one can design different DNA hydrogels with desired structures and properties.

Indeed, DNA hydrogels fabricated from different DNA monomers have specific chemical and physical properties. The mechanical properties of DNA hydrogels were tested using a Dynamic Mechanical Analyzer (DMA 2980, TA Instruments). Swollen X-DNA gel with an oriented network structure showed the strongest tensile modulus among all the DNA hydrogels (Table 2), probably due to the fact that the cross-linked DNA molecules strongly resisted deformation. The X-DNA gel showed the lowest tensile strength percentage among all the DNA hydrogels, indicating that the linked DNA molecules are more resistant to returning to their original shape at a given stress in the linear range.

Figures 3A, 3B:
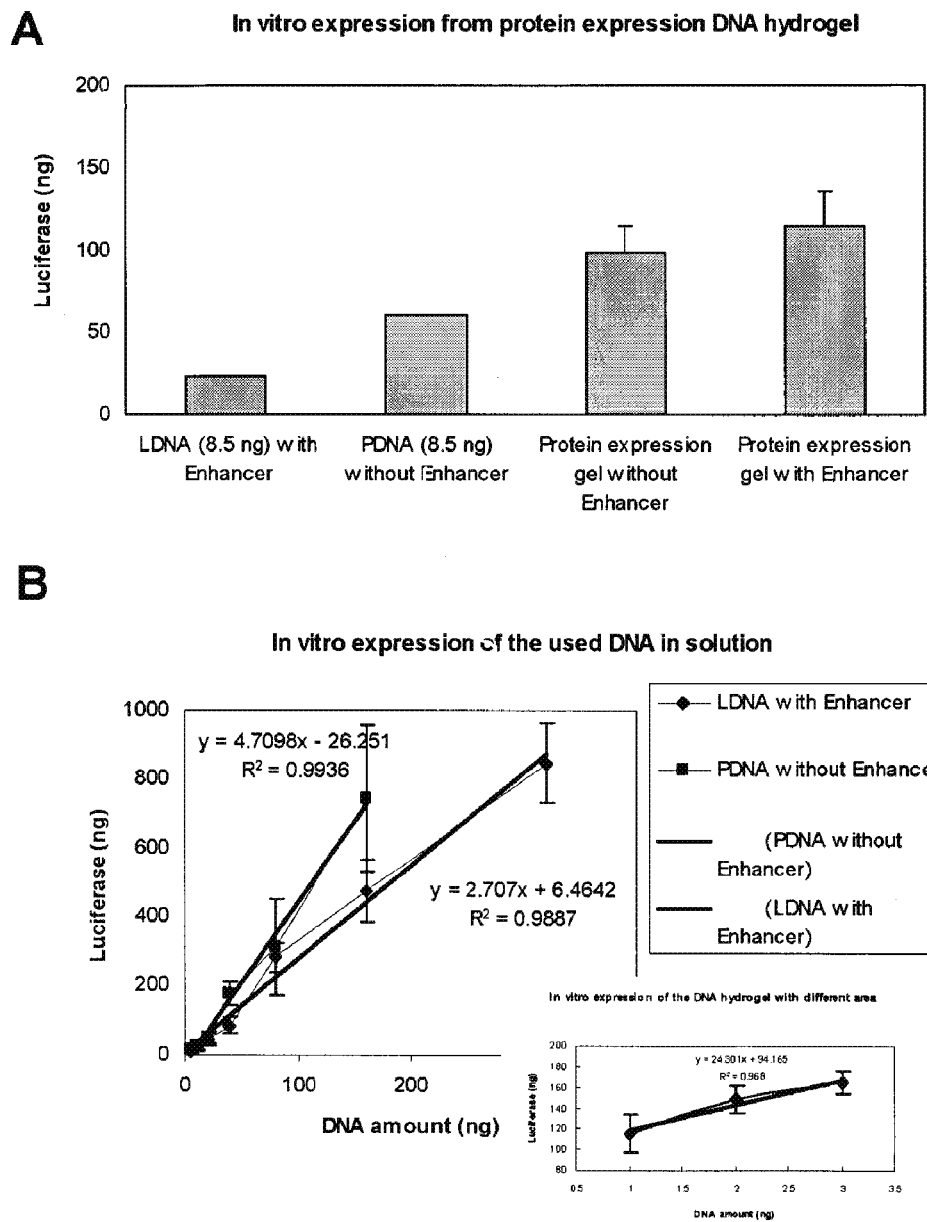
FIG. 3: In vitro expression of the *renilla* luciferase gene from DNA hydrogel pad with 200 μm×400 μm×20 μm. (A) A gene expression efficiency of the protein producing DNA hydrogel was 2 times as much as that of the plasmid DNA (PDNA) in solution. A gene expression efficiency of the DNA hydrogel is 5 times higher than that of linear gene DNA (LDNA) in solution. (B) According to a protein standard curve and an in vitro expression curve, ~150 ng of a luciferase is produced from DNA hydrogel (C) Cell-free, Luciferase expression (Linear DNA in solution vs. Supercoil DNA in solution vs P-gel. (D) Expression and visualization of luciferase using plasmid, linear and P-gel.
Figure 3C:
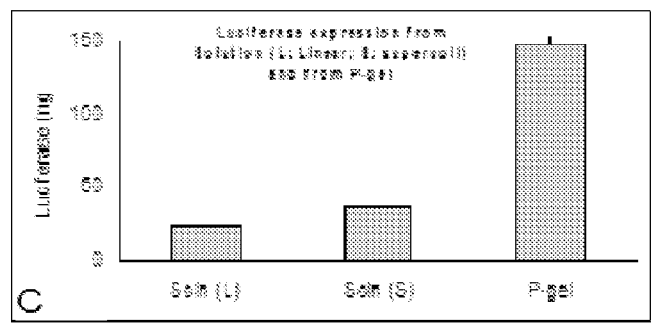
Figure 3D:
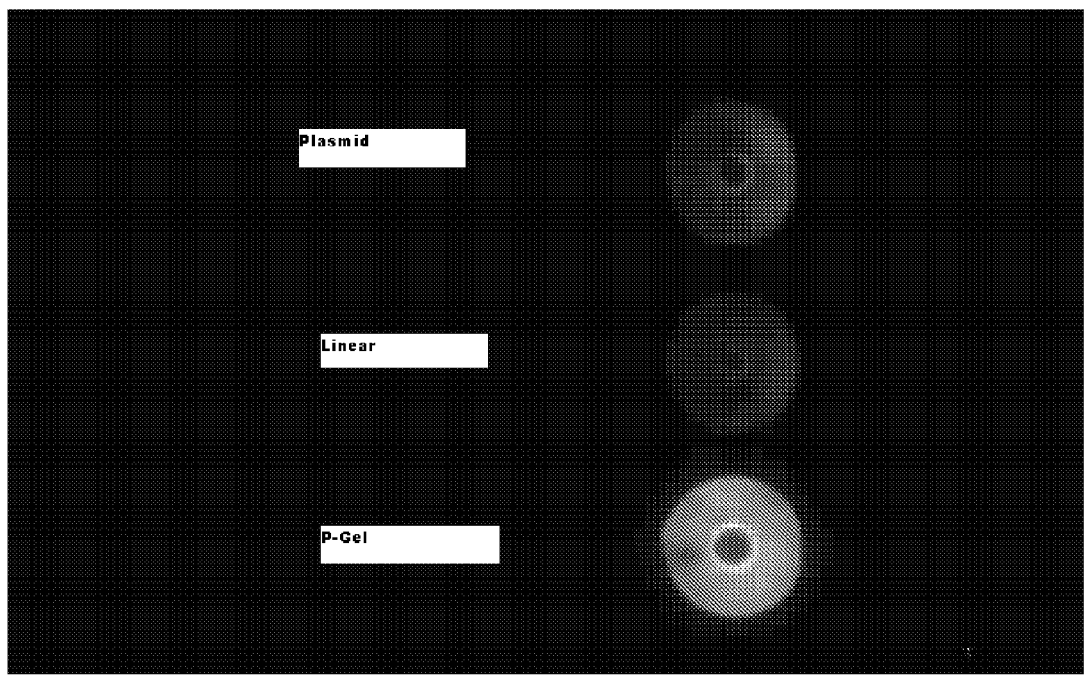

In addition, gel degradability can also be adjusted by selection of different types and/or different concentrations of DNA monomers. Degradation processes of empty DNA hydrogels were evaluated by measuring their daily DNA mass loss in the presence of various media (FIG. 3A). Over 60% of the X-DNA gel still remained in the phosphate buffered saline (PBS, pH 7.4) at room temperature for 10 days while 50% of both the Y-DNA and T-DNA gels were rapidly degraded after 2 days and 5 days, respectively. In 10% serum-supplemented media, X-DNA gel showed the slowest degradation among the other DNA hydrogels. Both Y-DNA and T-DNA gels were completely degraded in the serum within 2 days and 4 days, respectively, but the more than 50% of X-DNA gel still remained after 5 days. These results showed that, as expected, the degradation processes are determined by the internal structures of DNA gels as well as the environment (e.g., in the presence of serum which is abundant in nucleases). The closely packed DNA networks inside the X-DNA gel may have prevented DNA molecules from being easily accessed by nucleases. To validate this notion, we conducted a degradation test at a low temperature (4° C.) when most enzymes were inactive. As expected, all DNA hydrogels showed little degradation even after a month (data not shown). This result also points to another advantage of DNA hydrogels: they are stable and can be stored for a long period of time under a refrigerated condition (4° C.).

In addition, for in vivo animal tests (B57L mice), where 250 ug of blank DNA gels where injected into mice no difference was observed as compared to controls (injection with PBS).

Example 2

Controlled Delivery

Nucleic acid hydrogels were explored for use as a novel, long-term, controlled drug release system (FIG. 3B). Two different model drugs were encapsulated and tested: (S)-(+)-camptothecin (CPT) and porcine insulin. CPT is a small molecule drug (Mw=348.3 Da) with anti-leukemia and anti-tumor activities while insulin is a macromolecule protein drug (Mw=5777.6 Da) with glucose regulation functions. Encapsulation was achieved in situ (no post-gelation loading was needed) and encapsulation efficiencies were extremely high (close to 100%). For the CPT drug, 99.6%, 99.5% and 99.5% efficiencies were obtained using X-, Y-, and T-DNA gels, respectively. For the insulin drug, 90.1%, 95.7%, and 96.6% efficiencies were achieved with X-, Y-, and T-DNA gels, respectively. Furthermore, FIG. 3B shows the controlled release profiles of these two drugs from 0.2 mM DNA hydrogels in PBS at 37° C.

No burst release was detected, and relatively smooth release curves were obtained. In particular, the release of the insulin drug was dependant on the types of DNA monomers. After 12 days, about 60%, 40%, and 30% of insulin were released from the Y-, T-, and XDNA gels, respectively. Differential release rates is attributed to the differing internal structures of the DNA gels. The X-DNA gel was considerably denser than the Y- and TDNA gels whose internal structures were not as tightly organized. On the other hand, CPT released from the DNA hydrogels showed a zero-order release profile for over a month, and there was no difference in the release profiles for the three different monomer DNA hydrogels. The linear and relatively slower release profiles of the CPT drug may have resulted from the smaller size of the drug and its high affinity to both major and minor grooves of the DNA molecules (Yang et al., *J Am Chem Soc* 120, 2979 (1998)).

Of course, it will be apparent to one of skill in the art that a particular matrix of the invention can be designed to deliver a particular drug target to determine release rates notwithstanding nucleic acid affinity characteristics for a candidate drug. For example, larger pore sizes may obviate or diminish any drug-nucleic acid interference characteristics that are present.

Therefore, by designing a matrix comprising different nucleic acid molecules, as well as nucleic acid molecules of different shape, sequence or length, a designer gel can be produced for any target drug, including any bioactive agent, cells, viruses, small molecules, peptides, polypeptides and antibodies, for example. Indeed, DNA hydrogels are soft materials whose mechanical properties can be precisely controlled. (e.g., FIG. 1; Table 9A).

Since the gelation conditions were very mild and since no organic solvent or high temperature was used, the DNA gels can be used for encapsulating live mammalian cells. Chinese Hamster Ovarian (CHO) cells were encapsulated that were pre-stained with CellTracker™ Red CMTPX Probes (Molecular Probes, Carlsbad, Calif.) into 0.2 mM X-DNA gels. X-DNA building blocks were stained with a DNA specific dye (SYBR I, green) before gelation. The fluorescent image of the CHO cells encapsulated into the DNA hydrogel is shown in FIG. 4A. Interestingly, these CHO cells were observed to divide, producing daughter cells even after being entrapped in the DNA hydrogel. The results strongly suggest that the DNA hydrogel could be a promising scaffold for cell transplant, 3D cell culture, and tissue engineering.

To assess the utility of the DNA hydrogel system for cell transplantation and also for in vivo administration of drugs, the biocompatability of DNA hydrogels was also evaluated. Cytotoxicity assays were performed with Chinese Hamster Ovarian (CHO) cells using the conventional CellTiter 96® Aqueous Non-Radioactive Cell Proliferation Assay (Promega, Madison, Wis.). Results revealed that all DNA hydrogels were non-toxic to cultured cells (FIG. 4B).

These novel DNA hydrogels can be formulated into diverse patterns at both millimeter and micrometer scale. By selecting different types of DNA monomers, the surface morphology and the internal structures, including the pore size of the gel, can be easily adjusted, e.g., by selecting different building blocks described above, varying the length, sequence or shape of said building blocks. More importantly, due to the very mild, aqueous conditions and efficient enzyme-catalyzed gelation, a variety of drugs (from small molecules to proteins to even live cells) can be encapsulated within the gel in situ; this unique feature not only totally eliminates the post-gelation drug loading step, but also realizes a close to 100% encapsulation efficiency. In addition, drugs and live cells are well preserved and protected because no organic solvents or harsh manipulations are used. Furthermore, controlled insulin-release has been accomplished for more than one month with no burst effect, and a zero-order release has been achieved for the release of CPT from the gels. These biodegradable, biocompatible, nucleic acid hydrogels are a new class of materials that can be exploited in a variety of biomedical applications including sustained drug delivery, tissue engineering, 3D cell culture, cell transplant therapy, and other biomedical applications.

Example 3

Cell-Free Protein Production

A new DNA hydrogel was constructed utilizing nucleic acids, where linearized plasmid vector containing a gene for *renilla* luciferase was used to cross-link X-shaped DNA (X-DNA), incorporating the gene into the DNA hydrogel. *Renilla* luciferase is a 36 kDa monomeric protein and does not require a post-translational modification for activity. The linearized plasmid vectors were prepared by digesting the vector at a single site using Mlu I restriction enzyme. The X-DNA building blocks were prepared through complimentary hybridization of four different oligonucleotides. The gel electrophoresis result showed a complete linearization of the circular DNA after Mlu I digestion (FIG. 1A). In addition, the complete X-DNA building blocks showed retarded mobility in 3% agarose gel (FIG. 1B): The faint bands below the complete X-DNA building block correspond to incompletely formed X-DNA.

The cross-linking (e.g., ligation) of X-DNA to linearized plasmids was done through ligation of the two using T4 DNA ligases. This led to a formation of a three dimensional DNA hydrogel that showed an increase in volume at over 600% upon hydration. The gel was patterned into micro-sized molds with defined dimensions: 200 μm×200 μm×20 μm, 200 μm×400 μm×20 μm, 400 μm×400 μm×20 μm in length×width×depth. A total of fifteen DNA gel pads were used for each experiment. To further study the structure of the micro-patterned DNA hydroge, a variety of visualization techniques including optical microscopy, differential interference contrast (DIC) microscopy, and tapping mode (Atomic Force Scanning Microscope) AFM were used. The optical microscopic images (FIG. 1C) show the DNA gel pads with 200 μm×400 μm×20 μm. In addition, staining the gel pads with the DNA specific dye, SYBR I, shows that the DNA gel pads were composed entirely of DNA as expected (FIG. 1D). The liquid AFM images show a disorderly internal structure of the swollen DNA gel with pore sizes ranging from approximately 10 nm to 200 nm (FIG. 1E). These images suggest that the linearized plasmid inserts (3.0 kb) exist as heavily coiled DNA with no defined structures.

In vitro expression of *Renilla* luciferase protein from DNA gel pads was conducted using a coupled gene transcription and translation (TNT) kit (Promega). The results showed that a gene expression in DNA gel form had approximately 3 times higher efficiency than a plasmid DNA in solution phase (FIG. 2A). In addition, this result was approximately 5 times higher than the linearized plasmid DNA in solution phase. In comparison with other solid phase in vitro protein expression systems, these results showed up to 25 times more efficient expression. e.g., Ditursi et al. Biotechnol Prog. 2004, 20, 1705-1709; Ghosh, et al. J Biochem Biophys Methods. 2005; 62(1):51-62 (teaching DNA immobilized on beads and immobilized onto microtiter plate wells for coupled transcription/translation cell-free protein expression, respectively). Because the DNA gel pad is composed only of DNA, there were no non-specific bindings that may have caused lower protein expression in other solid phase systems. In other solid phase systems, biotin labeled linearized plasmids were immobilized onto avidin-covered solid beads where T7 RNA polymerase bound non-specifically to the biotin labeled linearized plasmids, disrupting gene expression.

More importantly, the gene incorporated DNA hydrogel was tested for the reusability of the gel for protein expression (FIG. 3A). Reduction of gene expression may have been caused by degradation of the gels by the nucleases from the TNT lysates. To test this hypothesis, a degradation study of the DNA gel pads in the PBS solution (pH 7.4) was performed (FIG. 3B). The gel pads showed no significant degradation after one day. The gel was substantially degraded after 7 days with 30% of the gel remaining. This showed the gel remained intact for at least one day, suggesting gel degradation was not the cause of reduction of protein production with repeated expression In conclusion, a *Renilla* luciferase gene comprising DNA hydrogel yields protein in significant quantity. This DNA hydrogel-based gene expression system showed substantially improved protein expression from previous solid-phase based gene expression systems. This system is reusable, biocompatible, and biodegradable, and can be used for production of protein in in vivo. This system could also be used as a novel protein delivery method where the protein to be delivered must be produced in situ.

Preparation of Thr Linear *Renilla* Luciferase Reporter Gene.

A plasmid DNA, pRL-null, containing *Renilla* luciferase driven by a T7 RNA polymerase promoter was purchased from Promega (Madison, Wis.). The plasmid DNA (pDNA) was amplified in competent *Escherichia coli* and purified by an Eppendorf Perfectprep® Plasmid Mini Kit (Westbury, N.Y.). The amplified and purified pDNA was digested with the restriction enzyme Mlu I (Promega), which cuts the plasmid at a single site before the T7 promoter.

Construction of the DNA Building Block and Protein Producing DNA Hydrogel.

The branched DNA sequences (Table 1) were designed and synthesized using commercially available oligonucleotide synthesis. Without further purification, oligonucleotides (Integrated DNA Technologies, Coralville, Iowa) were dissolved in an annealing buffer (10 mM Tris, pH=8.0, 1 mM ethylenediaminetetraacetic acid (EDTA), and 50 mM NaCl) with a final concentration of 50 mM. X-DNA was constructed by mixing four oligonucleotide components (with the same molar ratio) in sterile Milli-Q water with a final concentration of 20 mM for each oligonucleotide. Hybridizations were performed according to the following procedures: (i) denaturation at 95° C. for 2 min. (ii) cooling at 65° C. and incubation for 2 min. (iii) annealing at 60° C. for 5 min. and (iv) further annealing at 60° C. for 0.5 min with a continuous temperature decrease at a rate of 1° C. per min. The annealing steps were repeated a total of 40 times. The final annealed products were stored at 4° C. The $X_{01}$ to $X_{04}$ were four corresponding single oligonucleotides that formed an X-DNA. To construct the protein producing X-DNA gel, the X-DNA (X-DNA concentration, 13 ug/ul) were ligated to the linearized pRL-null vectors (linear pRL-null vector concentration, 2.21 ug/ul) using T4 DNA ligase (Promega). The mixture was incubated overnight at room temperature.

Fabrication of DNA Gel Micropads.

A micro-meter scale DNA gel pad was prepared by molding the DNA pre-gel solution in a PDMS replica that was fabricated by photolithography. The dimensions of the gel micropads were 20 μm×200 μm×400 μm. A DNA pre-gel solution (1 μl) was dropped onto an APTES modified glass slide, and a PDMS replica was placed on the solution. After curing for 8 hours at room temperature, the PDMS replica was peeled off. The DNA gel micro-patterns were visualized using a fluorescence microscope after staining with the DNA specific dye, SYBR I.

Characterization of Swollen DNA Hydrogels.

AFM was carried out under water in a fluid cell on PicoPlus AFM (Molecular Imaging, Tempe, Ariz.) in MAC mode using type II MAClevers tips (Molecular Imaging, Tempe, Ariz.). Mica was chosen as a solid substrate and used immediately after cleavage in a clean atmosphere. For the sample preparation, surface modification was accomplished by a deposit of silane in MilliQ water. Briefly, the fresh mica was placed in a container filled with 10 ml 3-aminopropyltriethoxysilane (APTES) solution (2% w/w) for 15 min, and then the APTES-derivatized mica was thoroughly washed with MilliQ water several times and dried with a gentle stream of nitrogen gas. A piece of DNA gel was loaded onto the mica for imaging.

In Vitro Degradation Assays.

Swollen gel pads were transferred to a microcentrifuge tube with 300 ul of PBS, pH 7.4. The tube was then incubated at 37° C. with slight agitating over night. After the incubation, the supernatant was removed, immediately followed by a measuring of the UV absorbance at 260 nm. 300 ul of Fresh PBS was added to the sample and then the degradation assay was repeated for 7 days.

In Vitro Transcription and Translation.

A coupled transcription and translation was carried out using the TNT Coupled Transcription/Translation System (Promega, Madison, Wis.) in a volume of 50 µl. For protein producing DNA hydroge, 15 gel pads produced from the micro-fabricated device were added to the expression solution. Incubation was carried out in a water bath at 30° C. for 75 min. All samples were stored at −80° C. before assaying for luciferase activity. The luciferase activity was evaluated by the *Renilla* Luciferase Assay System (Promega, Madison, Wis.) and measured with a luminometer.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed:

1. A composition comprising a three-dimensional scaffold comprising a plurality of nucleic acid molecules, wherein said scaffold has an ultimate elongation of about 35 to about 65%.

2. The composition of claim 1, wherein said composition has a molecular weight of about 50 kDa to about 550 MDa.

3. The composition of claim 1, wherein each of said plurality of nucleic acid molecules has a shape selected from a group consisting of an X-shape, Y-shape, dumbbell-shape, T-shape, and a combination thereof.

4. The composition of claim 3, wherein said nucleic acid molecules are DNA.

5. The composition of claim 3, wherein said composition further comprises linear or circular nucleic acid sequences.

6. The composition of claim 3, wherein said shape is Y shape.

7. The composition of claim 6, wherein a nucleic acid molecule of said plurality of Y-shape nucleic acid molecules is selected from the group of SEQ ID NOs 65-79 and SEQ ID NOs 92-102.

8. The composition of claim 3, wherein said shape is X shape.

9. The composition of claim 8, wherein a nucleic acid molecule of said plurality of X-shape nucleic acid molecules is selected from the group of SEQ ID NOs 65-79 and SEQ ID NOs 92-102.

10. The composition of claim 1, wherein each of said plurality of said nucleic acid molecules has a dumbbell shape.

11. The composition of claim 10, wherein a nucleic acid molecule of said plurality of dumbbell shape nucleic acid molecules is selected from the group of SEQ ID NOs 65-79 and SEQ ID NOs 92-102.

12. The composition of claim 1, wherein each of said plurality of said nucleic acid molecules has a T-shape.

13. The composition of claim 12, wherein a nucleic molecule of said plurality of T-shape nucleic acid molecules is selected from the group of SEQ ID NOs 65-79 and SEQ ID NOs 92-102.

14. The composition of claim 1, wherein said nucleic acid molecules are linked to each other to form a hydrogel.

15. The composition of claim 14, wherein said composition comprises entirely X-shape nucleic acids.

16. The composition of claim 14, wherein composition comprises entirely Y-shape nucleic acids.

17. The composition of claim 14, wherein said nucleic acid molecules are enzymatically linked.

18. The composition of claim 17, wherein said enzyme is selected from a group consisting of DNA polymerase, RNA reverse transcriptase, terminal transferase, DNA ligase, RNA ligase, exonuclease, ribonuclease, endonuclease, polynucleotide kinase, DNA methylase, and DNA ubiquitinase.

19. The composition of claim 17, wherein said enzyme is selected from a group consisting of enzymes that shorten nucleic acids, lengthen nucleic acids, amplify nucleic acids, and label nucleic acids.

20. The composition of claim 16, wherein at least a portion of said hydrogel is linked to at least one additional polymer.

21. The composition of claim 17 or 20, wherein a predetermined geometric pattern provides a plurality of pores.

22. The composition of claim 20, wherein said at least one additional polymer is selected from a group consisting of comprises poly(N-isopropylacrylamide), poly(N-alkylacrylamide), poly(N-n-propylacrylamide), poly(N-isopropylmethacrylamide), peptide, polypeptide, poly(ethylene oxide)-poly(propylene oxide)-poly(ethylene oxide), poly (DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly (epsilon-caprolactone), polyanhydride, poly(bis(p-carboxyphenoxy) propane-sebacic acid), polyorthoester, polyphosphoester, polyphosphazene, polystyrene, polyurethane, poly(amino acid), or a derivative thereof.

23. The composition of claim 21, wherein said pores have a size that is less than 15 nanometers.

24. The composition of claim 21, wherein said pores have a size selected from a group consisting of about 5 nanometers, about 10 nanometers, about 15 nanometers, about 20 nanometers, about 30 nanometers, about 40 nanometers, about 50 nanometers, and about 100 nanometers.

25. The composition of claim 21, wherein said pores have a size selected from a group of ranges consisting of about 0.1 micron to about 5 microns, about 10 microns to about 20 microns, about 20 microns to about 30 microns, about 30 microns to about 40 microns, about 40 microns to about 50 microns, about 50 microns to about 100 microns, and about 100 microns to about 200 microns.

26. The composition of claim 21, wherein said composition provides a three dimensional scaffold for cell growth.

27. The composition of claim 21, wherein said composition provides a three dimensional scaffold for tissue generation.

28. A method of encapsulating one or more compounds in a composition according to claim 1, comprising the steps of:
providing an aqueous solution comprising said one or more compounds;
mixing said aqueous solution with a mixture comprising a plurality of branched nucleic acid molecules and ligase enzyme;
allowing linking of said branched nucleic acid molecules to form said composition according to claim 1;
thereby encapsulating said one or more compounds in said composition according to claim 1.

29. The method of claim 28, wherein each of said branched nucleic acid molecules is of one or more shape.

30. The method of claim 28, wherein method occurs at room temperature.

31. The method of claim 28, wherein said method occurs at neutral pH.

32. The method of claim 29, wherein said one or more shape is selected from Y-shaped, X-shaped, dumbbell-shaped, T-shaped or any combination thereof.

33. The method of claim 32, wherein said composition is comprised substantially of X-shaped branched DNA molecules.

34. The method of claim 32, wherein said composition is comprised substantially of Y-shaped branched DNA molecules.

35. The method of claim 32, wherein said composition is comprised substantially of T-shaped branched DNA molecules.

36. The method of claim 28, wherein said one or more compounds is a therapeutic.

37. A method for delivering a compound comprising the steps of:
providing a composition according to claim 1 comprising branched nucleic acid molecules encapsulating said compound;
administering said composition to a subject, whereby said composition releases said compound in a time controlled manner;
thereby delivering said compound.

38. The method of claim 37, wherein said compound is a drug.

39. The method of claim 37, wherein said compound is a cell.

40. The method of claim 37, wherein said delivery is to a cell, tissue, organ or skin.

41. The method of claim 37, wherein said branched nucleic acid molecules are X-shaped, Y-shaped, T-shaped, or a combination thereof.

42. The method of claim 37, wherein said composition is comprised entirely of X-shaped nucleic acid molecules.

43. The method of claim 37, wherein said composition comprises pores.

44. The method of claim 43, wherein said pores have a size greater than about 15 nanometers.

45. The method of claim 43, wherein said pore size is less than 15 nanometers.

46. The method of claim 39, wherein said composition provides a three dimensional matrix, on which said cells grow.

47. The method of claim 37, comprising an additional step of modifying said composition so that said composition comprises an additional polymer.

48. The method of claim 47, wherein said additional polymer is polystyrene.

49. The method of claim 47, wherein said additional polymer is selected from a group consisting of poly(N-isopropylacrylamide), poly(N-alkylacrylamide), poly(N-n-propylacrylamide), poly(N-isopropylmethacrylamide), peptide, polypeptide, poly(ethylene oxide)-poly(propylene oxide)-poly(ethylene oxide), elastin-like polypeptides, a polyester, polylactide, poly(L-lactic acid), poly(D,L-lactic acid), poly(lactide-co-glycolides), biotinylated poly(ethylene glycol-block-lactic acid), poly(DTEC), dextran-polylactide, poly(alkylcyanoacrylate), poly(epsilon-caprolactone), polyanhydride, poly(bis(p-carboxyphenoxy) propane-sebacic acid), polyorthoester, polyphosphoester, polyphosphazene, polystyrene, polyurethane, poly(amino acid), or a derivative thereof.

* * * * *

UNITED STATES PATENT AND TRADEMARK OFFICE
CERTIFICATE OF CORRECTION

PATENT NO. : 8,486,621 B2  Page 1 of 1
APPLICATION NO. : 11/464184
DATED : July 16, 2013
INVENTOR(S) : Luo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 927 days.

Signed and Sealed this
Tenth Day of March, 2015

Michelle K. Lee
*Deputy Director of the United States Patent and Trademark Office*